United States Patent
Wildum et al.

(10) Patent No.: US 9,249,148 B2
(45) Date of Patent: Feb. 2, 2016

(54) TRIS(HETERO)ARYLPYRAZOLES AND USE THEREOF

(71) Applicant: AICURIS GMBH & CO. KG, Wuppertal (DE)

(72) Inventors: Steffen Wildum, Gevelsberg (DE); Burkhard Klenke, Wuppertal (DE); Astrid Wendt, Wuppertal (DE)

(73) Assignee: AICURIS GMBH & CO. KG, Wuppertal (DE)

( * ) Notice: Subject to any disclaimer, the term of this patent is extended or adjusted under 35 U.S.C. 154(b) by 0 days.

(21) Appl. No.: 14/422,191

(22) PCT Filed: Aug. 16, 2013

(86) PCT No.: PCT/EP2013/067201
§ 371 (c)(1),
(2) Date: Feb. 18, 2015

(87) PCT Pub. No.: WO2014/027112
PCT Pub. Date: Feb. 20, 2014

(65) Prior Publication Data
US 2015/0203500 A1    Jul. 23, 2015

(30) Foreign Application Priority Data

Aug. 17, 2012 (DE) .......................... 10 2012 016 908

(51) Int. Cl.
| | | |
|---|---|---|
| *C07D 403/02* | (2006.01) | |
| *C07D 487/04* | (2006.01) | |
| *A61K 31/4745* | (2006.01) | |
| *C07D 471/04* | (2006.01) | |
| *C07D 401/14* | (2006.01) | |
| *C07D 403/04* | (2006.01) | |

(52) U.S. Cl.
CPC .......... *C07D 487/04* (2013.01); *A61K 31/4745* (2013.01); *C07D 401/14* (2013.01); *C07D 403/04* (2013.01); *C07D 471/04* (2013.01)

(58) Field of Classification Search
CPC ...................................... C07D 471/04
USPC ....................................... 548/364.7
See application file for complete search history.

(56) References Cited

U.S. PATENT DOCUMENTS

| | | | |
|---|---|---|---|
| 6,277,847 | B1 | 8/2001 | Theodoridis et al. |
| 8,314,089 | B2 | 11/2012 | Schohe-Loop et al. |
| 8,399,433 | B2 | 3/2013 | Appari et al. |
| 2011/0136764 | A1 | 6/2011 | Appari et al. |
| 2011/0172207 | A1 | 7/2011 | Schohe-Loop et al. |
| 2013/0005705 | A1 | 1/2013 | Geneste et al. |
| 2013/0203756 | A1 | 8/2013 | Bunda et al. |
| 2013/0210809 | A1 | 8/2013 | Bolea et al. |
| 2013/0231306 | A1 | 9/2013 | Crew et al. |
| 2015/0203500 | A1 | 7/2015 | Wildum et al. |

FOREIGN PATENT DOCUMENTS

| | | | | |
|---|---|---|---|---|
| DE | 10 2008 015032 | * | 9/2009 | .......... C07D 471/04 |
| DE | 102008015032 A1 | | 9/2009 | |
| DE | 102012016908 A1 | | 2/2014 | |
| WO | 2010141406 A2 | | 12/2010 | |
| WO | 2012009009 A2 | | 1/2012 | |
| WO | 2012058133 A1 | | 5/2012 | |
| WO | 2013000994 A1 | | 1/2013 | |
| WO | 2014027112 A1 | | 2/2014 | |
| WO | 2015121413 A1 | | 8/2015 | |

OTHER PUBLICATIONS

International Search Report from PCT/EP2013/067201 dated Oct. 8, 2013.

* cited by examiner

*Primary Examiner* — Nizal Chandrakumar
(74) *Attorney, Agent, or Firm* — Millen White Zelano and Branigan, PC; John Sopp; Anthony Zelano

(57) ABSTRACT

The present invention relates to new tri(hetero)aryl pyrazoles, methods for their preparation, their use for treating and/or preventing diseases as well as their use in the preparation of drugs for treating and/or preventing diseases, in particular retroviral diseases in humans and/or animals.

19 Claims, No Drawings

TRIS(HETERO)ARYLPYRAZOLES AND USE THEREOF

The present invention relates to new tri(hetero)aryl pyrazoles, methods for their preparation, their use for treating and/or preventing diseases as well as their use in the preparation of drugs for treating and/or preventing diseases, in particular retroviral diseases in humans and/or animals.

The human immunodeficiency virus (HIV) causes a chronic persistent, progressive infection. The disease proceeds through various stages from the asymptomatic infection to the full clinical picture of AIDS (Acquired Immunodeficiency Syndrome). AIDS is the final stage of the disease caused by the infection. A characteristic of HIV/AIDS is the long clinical latency period with persistent viremia, which leads in the end stage to failure of the immune defenses.

By introducing the anti-HIV combination therapy, it was possible to bring about long-term slowing of the progression of the disease in the 1990s and thus to substantially extend the life expectancy of HIV-infected patients (Palella et al., N. Engl. J. Med. 1998, 238, 853-860).

The anti-HIV substances currently on the market inhibit either the replication of the HI virus through inhibition of its essential viral enzyme reverse transcriptase (RT; reverse transcriptase inhibitors), of protease (protease inhibitors) or of integrase (integrase inhibitors); or of the entry of HIV into the target cells (so-called entry inhibitors) (see on this the overview in Flexner, Nature Reviews Drug Discovery 2007, 6, 959-966). Three medication classes of RT inhibitors exist: Nucleoside RT inhibitors (NRTI) and nucleotide RT inhibitors (NtRTI) work through competitive inhibition or chain termination in DNA polymerization. On the other hand, non-nucleoside RT inhibitors (NNRTI) bind allosterically to a hydrophobic pocket in the proximity of the active center of the RT and induce a change in the conformation of the enzyme. The currently available protease inhibitors (PI) block the active center of the viral protease and thus prevent newly created particles from maturing into infectious virions. The single currently approved integrase inhibitor Raltegravir binds to the active center of the HIV integrase and prevents the integration of the proviral DNA into the host cell genome. Entry inhibitors (fusions inhibitors and co-receptor antagonists) prevent the HIV infection of cells through interaction with the HIV envelope protein or through blocking the cellular co-receptors CCR5 or CXCR4.

Since monotherapy with the currently available anti-HIV medications leads within a short time to treatment failure through selection of resistant viruses, combination therapy is normally used with several anti-HIV substances from different classes within a so called highly active antiretroviral therapy (generic term HAART) (Carpenter et al., J. Am. Med. Assoc. 2000, 283, 381-390).

Despite the progress in antiretroviral chemotherapy, recent trials show that eradication of HIV and associated curing of the HIV infection cannot be expected with the available medications. The latent virus remains in resting lymphocytes, thus constituting a reservoir for reactivation, and thus new propagation of the virus (Finzi et al., Nature Med. 1999, 5, 512-517; Lewin et al., J Int AIDS Soc. 2011 Jan. 24; 14:4.). As a result, HIV-infected patients depend on a lifelong efficient antiviral therapy. Despite a combination therapy there may be a selection of resistant viruses after some time. Since characteristic resistance mutations accumulate for each therapeutic class, the failure of a therapy often leads to loss of effectiveness of the entire substance class (or medication class). This cross-resistance problem is most characteristic of the NNRTIs class, since here often even a single point mutation in the RT may be sufficient to cause a loss of effectiveness of all NNRTIs (see overview in Kavlick & Mitsuya, Antiretroviral Chemotherapy (Publisher: De Clercq E.), 2001, ASM Press, 279-312). Furthermore, the creation of resistances is usually favoured by poor compliance on the part of patients, caused by an unfavourable side-effects profile and/or a complicated dosage regimen for anti-HIV medication.

In consequence, there is an urgent need for new therapeutic options to fight HIV infection. In so doing, a pre-eminent goal of therapy research on HIV is the identification of new chemical lead structures which either address a new target in the proliferation of HIV and/or are effective against the growing number of resistant clinical HW isolates.

The chemical substance class of pyrazoles has already been described many times for various indications: U.S. Pat. No. 5,624,941 and EP 576357 describe pyrazoles as cannabinoid receptor antagonists; EP 418845, EP 554829 and WO 04/050632 among other things for the treatment of inflammatory and thrombotic diseases; WO 03/037274 as sodium ion channel inhibitors for the treatment of pain; WO 06/015860 as adenosine receptor ligands for the treatment of inflammatory and obstructive respiratory diseases; EP 1762568 as inhibitors of platelet aggregation; WO 07/002559 as modulators of the activity of nuclear receptors; WO 07/020388 and WO 05/080343 as cannabinoid receptor modulators, among other things for the treatment of obesity and psychiatric and neurological disorders; WO 07/009701 and EP 1743637 for the treatment of cardiovascular risk factors; and DE 10 2004 054 666 to fight weeds or to regulate plant growth.

WO 2011/058149 describes tricyclic pyrazole derivatives as PI3k inhibitors for the treatment of autoimmune diseases. WO 2008/074982 describes pyrazole derivatives as CB1 receptor modulators in the treatment of overweight. Pyrazole derivatives as agents against blood platelet aggregation for the treatment of ischemic diseases are described in WO 2004/069824 and WO 2006/004027. Pyrazole derivatives as COX-1 inhibitors are described in WO 2004/050632 and US 2004/0116475. WO 2008/017932 describes various aryl sulfonamides, among them a pyrazole-containing example, as carbonic anhydrase inhibitors.

DE 10 2008 015 033 and DE 10 2008 015 032 describe phenyl-substituted pyrazoles and their use for the treatment and prevention of infections with retroviruses.

One problem to be solved by this invention is to make available new compounds with the same or improved antiviral effectiveness for the treatment of viral infectious diseases in humans and animals, which do not exhibit the above-described disadvantages.

A particular portion of the aforementioned problem of the present invention is to make available new compounds with the same or improved antiviral effect for the treatment of retroviral infectious diseases, preferably of HIV-1 and HIV-2 induced infections in humans and animals, which do not exhibit the above-described disadvantages.

Surprisingly, it was found that the tri(hetero)aryl pyrazoles described in the present invention are antivirally effective. In particular, the tri(hetero)aryl pyrazoles in accordance with the invention are anti-retrovirally effective, preferably against HI viruses, such as HIV-1 and HIV-2.

Subject matter of the invention are compounds of formula

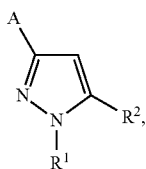
(I)

wherein
A stands for a group of formula

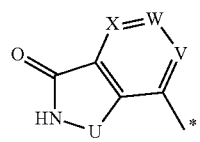

wherein
U stands for nitrogen or carbon,
  whereby nitrogen can be substituted with an alkyl substituent,
  whereby carbon can be substituted with 1 to 2 alkyl substituents, which are selected independently of one another, or with an oxo substituent,
V stands for nitrogen or carbon,
  whereby carbon can be substituted with a substituent selected from the group consisting of halogen, amino, hydroxy, methoxy, methyl and trifluoromethyl,
W stands for nitrogen or carbon,
  whereby carbon can be substituted with a substituent selected from the group consisting of halogen, amino, hydroxy, methoxy, methyl and trifluoromethyl,
X stands for nitrogen or carbon,
  whereby carbon can be substituted with a substituent selected from the group consisting of halogen, amino, hydroxy, methoxy, methyl and trifluoromethyl, and
* is the point of attachment to the carbon atom,
$R^1$ stands for phenyl or pyridyl,
  whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
  alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl, whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N-oxide,
wherein
  alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl, and
$R^2$ stands for phenyl or pyridyl,
  whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
  alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
  whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N-oxide,
wherein
  alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl, and their salts, their solvates or the solvates of their salts.

Further subject matter of the invention are compounds of the above represented formula (I), in which A stands for a group of the formula as represented above, wherein
U stands for nitrogen or carbon,
  whereby nitrogen can be substituted with an alkyl substituent;
  whereby carbon can be substituted with 1 to 2 alkyl substituents, which are selected independently of one another, or with an oxo substituent;
U preferably stands for carbon,
  whereby carbon can be substituted with 1 to 2 alkyl substituents, which are selected independently of one another, or with an oxo substituent;
U further preferred stands for carbon
and their salts, their solvates or the solvates of their salts.

Further subject matter of the invention are compounds of the above represented formula (I) in which A stands for a group of the formula as represented above, wherein
V stands for nitrogen or carbon,
  whereby carbon can be substituted with a substituent selected from the group consisting of halogen, amino, hydroxy, methoxy, methyl and trifluoromethyl;
V preferably stands for nitrogen or carbon,
V further preferred stands for nitrogen
and their salts, their solvates or the solvates of their salts.

Further subject matter of the invention are compounds of the above represented formula (I) in which A stands for a group of the formula as represented above, wherein
W stands for nitrogen or carbon,
  whereby carbon can be substituted with a substituent selected from the group consisting of halogen, amino, hydroxy, methoxy, methyl and trifluoromethyl;
W preferably stands for carbon,
  whereby carbon can be substituted with a substituent methyl
and their salts, their solvates or the solvates of their salts.

Further subject matter of the invention are compounds of the above represented formula (I) in which A stands for a group of the formula as represented above, wherein X stands for nitrogen or carbon,
  whereby carbon can be substituted with a substituent selected from the group consisting of halogen, amino, hydroxy, methoxy, methyl and trifluoromethyl;
X preferably stands for nitrogen or carbon,
and their salts, their solvates or the solvates of their salts.

Further subject matter of the invention are compounds of the above represented formula (I) wherein $R^1$ stands for phenyl or pyridyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
  alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby the preferred 1 to 2 substituents are more preferably selected independently of one another from the group consisting of halogen, nitro, (C1-C4)-alkyl and (C1-C4)-alkoxy, and said halogen is more preferably selected independently of one another from Cl and F, and the alkyl and alkoxy on their part can be substituted one to three times with fluorine atoms, preferably with 2 fluorine atoms, more preferred with 3 fluorine atoms;
whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N-oxide,
wherein
  alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
$R^1$ preferably stands for pyridyl,
whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N-oxide,
wherein
  alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
$R^1$ more preferred stands for 3-pyridyl or 4-pyridyl,
whereby pyridyl can be substituted with a halogen substituent
$R^1$ most preferred stands for pyridyl,
and their salts, their solvates or the solvates of their salts.

Further subject matter of the invention are compounds of the above represented formula (I), wherein $R^2$ stands for phenyl or pyridyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
  alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby the preferred 1 to 2 substituents are more preferably selected independently of one another from the group consisting of halogen, nitro, (C1-C4)-alkyl and (C1-C4)-alkoxy, and said halogen is more preferably selected independently of one another from Cl and F, and the alkyl and alkoxy on their part can be substituted one to three times with fluorine atoms, more preferred with 2 fluorine atoms, most preferred with 3 fluorine atoms,
whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N-oxide,
wherein
  alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
$R^2$ preferably stands for phenyl,
whereby phenyl is substituted with 1 to 2 substituents, said 1 to 2 substituents being more preferably selected independently of one another from the group consisting of halogen, nitro, (C1-C4)-alkyl and (C1-C4)-alkoxy, and the halogen more preferably being selected independently of one another from Cl and F, and the alkyl and alkoxy on their part can be substituted one to three times with fluorine atoms, more preferred with 2 fluorine atoms, most preferred with 3 fluorine atoms,
$R^2$ most preferred stands for 3-Cl-5-$CF_3$O-phenyl
and their salts, their solvates or the solvates of their salts.

Further, the compounds of formulae (Ia), (Ib), (Ic) and (Id) and their salts, solvates and solvates of their salts, explained in more detail below, are components of the present invention. In consequence:

Compounds in accordance with the invention are the compounds of formulae (I), (Ia), (Ib), (Ic) and (Id) and their salts, solvates and solvates of their salts, as well as the compounds and their salts, solvates and solvates of their salts comprised by formulae (I), (Ia), (Ib), (Ic) and (Id), hereinafter mentioned as exemplary embodiment(s), insofar the compounds mentioned hereafter, comprised by formulae (I), (Ia), (Ib), (Ic) and (Id), are not already salts, solvates and solvates of their salts.

Provided the compounds in accordance with the invention can occur in tautomeric forms, the present invention comprises any tautomeric form.

Isomers are to be understood as tautomers or tautomeric forms within the scope of the present invention, which are characterized in that said isomers have the same chemical formula as their original compound in accordance with the respective formula (I), or (Ia), or (Ib), or (Ic) or (Id) or their salts, solvates and solvates of their salts; isolated atoms, however, can be positionally arranged differently. Given the context of the present invention, these isomers are therefore described as tautomers or tautomeric forms because they can quickly interconvert into each other through the migration of isolated atoms or atom groups, and, in so doing, the respective isomers can be in a rapidly changing chemical equilibrium with one another. Given the context of the present invention, the tautomers or tautomeric forms thus only differ in the position of a chemical group and in the position of a double bond and can be understood as the same chemical compound in accordance with the formula (I), or (Ia), or (Ib), or (Ic) or (Id) or their salts, solvates and solvates of their salts from the viewpoint of chemical components.

As salts, within the scope of the present invention, physiologically acceptable salts of the compounds pursuant to the invention are preferred. Comprised, however, are also salts, which are not suitable for pharmaceutical administration itself, but can, for example, be used for the isolation or cleaning of the compounds in accordance with the invention.

Physiologically acceptable salts of the compounds of the invention include acid addition salts of mineral acids, carboxylic acids, and sulfonic acids, e.g. salts of hydrochloric acid, hydrobromic acid, sulfuric acid, phosphoric acid, methane sulfonic acid, ethane sulfonic acid, p-toluene sulfonic acid, benzene sulfonic acid, naphthalene disulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds in accordance with the inventions also comprise salts of customary bases, such as exemplary and preferably alkali metal salts (e.g., sodium and potassium salts), alkaline earth metal salts (e.g., calcium and magnesium salts) and ammonium salts, derived from ammonia or organic amines with 1 to 16 C atoms, such as exemplarily and preferably ethylamine, diethyl amine, triethyl amine, ethyl diisopropylamine, monoethanolamine, diethanolamine, triethanolamine, dicyclohexylamine, dimethylaminoethanol, procaine, dibenzylamine, N-methylmorpholine, arginine, lysine, ethylendiamine and N-methylpiperidine.

Solvates within the scope of the invention are those forms of the compounds in accordance with the invention that in a solid or liquid state forms a complex through coordination with solvent molecules. Hydrates are a special form of the solvate in which the coordination takes place with water.

Accordingly, within the scope of the present invention the term solvates also always includes their hydrates with the above-cited definition.

Within the scope of the present invention the substituents, unless otherwise specified, have the following meaning:

Alkyl as well as the alkyl parts in alkoxy and alkoxy carbonyl stand for branched or unbranched alkyl and, unless otherwise stated, comprise (C1-C6)-alkyl, in particular (C1-C4)-alkyl, such as, e.g., methyl, ethyl, propyl, isopropyl, butyl, isobutyl, tert. butyl.

Alkoxy within the scope of the invention preferably stands for a branched or unbranched alkoxy residue, in particular with 1 to 6, 1 to 4 or 1 to 3 carbon atoms. Preferred is an unbranched or branched alkoxy residue with 1 to 3 carbon atoms. Exemplarily and preferably, reference is made to: methoxy, ethoxy, n-propoxy, isopropoxy, t-butoxy, n-pentoxy and n-hexoxy.

Alkoxy carbonyl exemplarily and preferably stands for methoxycarbonyl, ethoxycarbonyl, n-propoxycarbonyl, isopropoxycarbonyl, t-butoxycarbonyl, n-pentoxycarbonyl and n-hexoxycarbonyl.

Heterocyclyl stands for monocyclic, heterocyclic residues with 4 to 8, preferably 5 to 6 ring atoms and up to 3, preferably up to 2 hetero atoms and/or hetero groups from the series N, O, S, SO, $SO_2$, whereby one nitrogen atom can also form one N-oxide. The heterocycle can be saturated or partially unsaturated. Preferred are 5- to 7-membered, monocyclic saturated heterocycles with up to two heteroatoms from the series O, N and S, exemplarily and preferably for 1,4-oxazepanyl, pyrrolidine-1-yl, pyrrolidine-2-yl, pyrroline-3-yl, tetrahydrofuranyl, tetrahydrothienyl, pyranyl, 1,3-thiazolidinyl, piperidine-1-yl, piperidine-2-yl, piperidine-3-yl, piperidine-4-yl, thiopyranyl, morpholine-2-yl, morpholine-3-yl, morpholine-4-yl, thiomorpholine-2-yl, thiomorpholine-3-yl, thiomorpholine-4-yl, perhydroazepinyl, piperazine-1-yl, piperazine-2-yl.

Halogen stands for fluorine, chlorine, bromine or iodine, with fluorine and chlorine being preferred, unless otherwise specified.

Within the scope of the invention, (C3-C6)-cycloalkyl stands for a monocyclic, saturated carbocycle with 3 to 6 ring-carbon atoms. Exemplarily and preferably reference is made to: cyclopropyl, cyclobutyl, cyclopentyl and cyclohexyl.

In the formula of the group that can stand for A, the end point of the line, next to which is an*, does not stand for a carbon atom or a CH2-group but is a component of the bond to the atom, to which A is bound.

The above stated general definitions or definitions of residues regarding preferred ranges, apply both to the end products of formula (I) and analogously to the respective starting material or intermediates required for manufacturing.

The above stated general definitions of residues or those regarding preferred ranges apply both to the end products of formulae (I), (Ia), (Ib), (Ic) and (Id) and analogously also to their salts, solvates and solvates of their salts and analogously also to the respective starting material or intermediate products thereof required for manufacturing.

Within the scope of the present invention the term "HIV-1 and HIV-2-induced diseases" describes infections that as a rule lead to an acute HIV-infection after an incubation period of about three to six weeks. This is characterized by fever, night sweats, fatigue, rashes, oral ulcers or arthralgia (joint pain). After a subsequent multi-year latent phase, which is usually symptom-free, these infections generally lead to AIDS.

Regarding the description of the residues in accordance with the invention of the formulae (I), (Ia), (Ib), (Ic) and (Id), the following applies:

The respective combinations or preferred combinations of residues specifically stated in the definitions of residues are also optionally replaced by residue definitions of other combinations independently of the respectively stated combinations of residues.

Subject matter of the invention are also compounds of formula (I), wherein

A has the aforementioned meaning, namely stands for a group of the formula

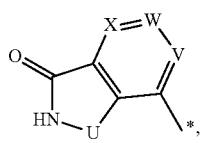

wherein
U stands for NH, CH2 or C=O,
V stands for N or CH,
W stands for CH or CMe, wherein CMe stands for C—CH3,
X stands for N or CH, and
* is the point of attachment to the carbon atom,
R¹ stands for phenyl or pyridyl,
whereby phenyl is substituted with 1 or 2 substituents, where the substituents are selected independently of one another from the group consisting of halogen, cyano, methyl, trifluoromethyl, methoxy and trifluoromethoxy,
whereby pyridyl can be substituted with 1 or 2 substituents, the substituents being selected independently of one another from the group consisting of halogen, methyl, and trifluoromethyl, and whereby the nitrogen atom of the pyridyl can form an N-oxide, and
R² stands for phenyl or pyridyl,
whereby phenyl is substituted with 1 or 2 substituents, the substituents being selected independently of one another from the group consisting of halogen, cyano, (C1-C4)-alkyl and (C1-C4)-alkoxy,
wherein
alkyl and alkoxy on their part can be substituted with 1 to 3 fluorine atoms,
whereby pyridyl can be substituted with 1 or 2 substituents, the substituents being selected independently of one another from the group consisting of halogen, cyano, (C1-C4)-alkyl and (C1-C4)-alkoxy, and whereby the nitrogen atom of the pyridyl can form an N-oxide,
wherein
alkyl and alkoxy on their part can be substituted with 1 to 3 fluorine atoms, and their salts, their solvates or the solvates of their salts.

Subject matter of the invention are also compounds of formula (I), wherein
A has the aforementioned meaning, wherein
U stands for NH, CH2 or C=O,
V stands for N or CH,
W stands for CH,
X stands for CH, and
* is the point of attachment to the carbon atom,
R¹ stands for phenyl or pyridyl,
whereby phenyl is substituted with 1 or 2 substituents, where the substituents are selected independently of one another from the group consisting of halogen, cyano, methyl, trifluoromethyl, methoxy and trifluoromethoxy,
whereby pyridyl can be substituted with 1 or 2 substituents, the substituents being selected independently of one another from the group consisting of halogen, methyl and trifluoromethyl, and whereby the nitrogen atom of the pyridyl can form an N-oxide, and
R² stands for phenyl or pyridyl,
whereby phenyl is substituted with 1 or 2 substituents, the substituents being selected independently of one another from the group consisting of halogen, cyano, (C1-C4)-alkyl and (C1-C4)-alkoxy,
wherein
alkyl and alkoxy on their part can be substituted with 1 to 3 fluorine atoms, whereby pyridyl can be substituted with 1 or 2 substituents, the substituents being selected independently of one another from the group consisting of halogen, cyano, (C1-C4)-alkyl and (C1-C4)-alkoxy, and whereby the nitrogen atom of the pyridyl can form an N-oxide,
wherein
alkyl and alkoxy on their part can be substituted with 1 to 3 fluorine atoms, and their salts, their solvates or the solvates of their salts.

Subject matter of the invention are also compounds of formula (I), wherein
A has the aforementioned meaning, wherein
U stands for NH or CH2,
V stands for N or CH,
W stands for CH or CMe, wherein CMe stands for C—CH3,
X stands for N or CH, and
* is the point of attachment to the carbon atom,
R¹ stands for pyridyl,
whereby pyridyl can be substituted with 1 or 2 substituents, the substituents being selected independently of one another from the group consisting of halogen, methyl and trifluoromethyl, and whereby the nitrogen atom of the pyridyl can form an N-oxide, and
R² stands for phenyl,
whereby phenyl is substituted with 1 or 2 substituents, the substituents being selected independently of one another from the group consisting of halogen, cyano, (C1-C4)-alkyl and (C1-C4)-alkoxy,
wherein
alkyl and alkoxy on their part can be substituted with 1 to 3 fluorine atoms, and their salts, their solvates or the solvates of their salts.

Subject matter of the invention are also compounds of formula (I), wherein
A has the aforementioned meaning, wherein
U stands for NH or CH2,
V stands for N or CH,
W stands for CH,
X stands for CH, and
* is the point of attachment to the carbon atom,
R¹ stands for pyridyl,
whereby pyridyl can be substituted with 1 or 2 substituents, the substituents being selected independently of one another from the group consisting of halogen, methyl and trifluoromethyl, and whereby the nitrogen atom of the pyridyl can form an N-oxide, and
R² stands for phenyl,
whereby phenyl is substituted with 1 or 2 substituents, the substituents being selected independently of one another from the group consisting of halogen, cyano, (C1-C4)-alkyl and (C1-C4)-alkoxy,
wherein
alkyl and alkoxy on their part can be substituted with 1 to 3 fluorine atoms, and their salts, their solvates or the solvates of their salts.

Subject matter of the invention are also compounds of formula (I), wherein
A has the aforementioned meaning, wherein
U stands for NH or CH2,
V stands for N or CH,
W stands for CH or CMe, wherein CMe stands for C—CH3, X stands for N or CH, and
* is the point of attachment to the carbon atom,
$R^1$ stands for 3-pyridyl or 4-pyridyl,
whereby pyridyl can be substituted with a halogen substituent, and
$R^2$ stands for phenyl,
whereby phenyl is substituted with 1 or 2 substituents, the substituents being selected independently of one another from the group consisting of halogen, cyano, (C1-C4)-alkyl, trifluoro-(C1-C4)-alkyl, (C1-C4)-alkoxy, trifluoro-(C1-C4)-alkoxy and difluoro-(C1-C4)-alkoxy, and their salts, their solvates or the solvates of their salts.

Subject matter of the invention are also compounds of formula (I), wherein
A has the aforementioned meaning, wherein
U stands for NH or CH2,
V stands for N or CH,
W stands for CH,
X stands for CH, and
* is the point of attachment to the carbon atom,
$R^1$ stands for 3-pyridyl or 4-pyridyl,
whereby pyridyl can be substituted with a halogen substituent, and
$R^2$ stands for phenyl,
whereby phenyl is substituted with 1 or 2 substituents, the substituents being selected independently of one another from the group consisting of halogen, cyano, (C1-C4)-alkyl, trifluoro-(C1-C4)-alkyl, (C1-C4)-alkoxy, trifluoro-(C1-C4)-alkoxy and difluoro-(C1-C4)-alkoxy,
and their salts, their solvates or the solvates of their salts.

Subject matter of the invention are also compounds of formula (I), wherein
A has the aforementioned meaning, wherein
U stands for NH or CH2, preferably for CH2,
V stands for N or CH, preferably for N,
W stands for CH or CMe, wherein CMe stands for C—CH3,
X stands for N or CH, preferably for N,
* is the point of attachment to the carbon atom,
$R^1$ stands for phenyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby said preferred 1 to 2 substituents are more preferably selected independently of one another from the group consisting of halogen, nitro, (C1-C4)-alkyl and (C1-C4)-alkoxy, and the halogen is more preferably selected independently of one another from Cl and F, and the alkyl and alkoxy on their part can be substituted one to three times with fluorine atoms, more preferred with 2 fluorine atoms, most preferred with 3 fluorine atoms; and
$R^2$ stands for phenyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby the preferred 1 to 2 substituents are more preferably selected independently of one another from the group consisting of halogen, nitro, (C1-C4)-alkyl and (C1-C4)-alkoxy, and the halogen is more preferably selected independently of one another from among Cl and F, and said alkyl and alkoxy on their part can be substituted one to three times with fluorine atoms, more preferred with 2 fluorine atoms, most preferred with 3 fluorine atoms,
$R^2$ most preferred stands for 3-Cl-5-CF$_3$O-phenyl,
and their salts, their solvates or the solvates of their salts.

Subject matter of the invention are also compounds of formula (I), wherein
A has the aforementioned meaning, wherein
U stands for NH or CH2, preferably for CH2,
V stands for N or CH, preferably for N,
W stands for CH or CMe, wherein CMe stands for C—CH3,
X stands for N or CH, preferably for N,
* is the point of attachment to the carbon atom,
$R^1$ stands for pyridyl,
whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N oxide,
wherein
alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
$R^1$ preferably stands for 3-pyridyl or 4-pyridyl,
whereby pyridyl can be substituted with a halogen substituent
$R^1$ most preferred stands for pyridyl; and
$R^2$ stands for phenyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby said preferred 1 to 2 substituents are more preferably selected independently from one another from among the group consisting of halogen, nitro, (C1-C4)-alkyl and (C1-C4) alkoxy, and said halogen is more preferably selected independently from one another from among Cl and F, and said alkyl and alkoxy can be substituted one to three times with fluorine atoms; more preferred with 2 fluorine atoms, most preferred with 3 fluorine atoms,
$R^2$ most preferred stands for 3-Cl-5-CF$_3$O-phenyl,
and their salts, their solvates or the solvates of their salts.

Subject matter of the invention are also compounds of formula

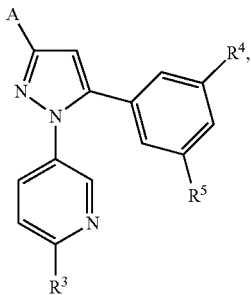

(Ia)

wherein
A has the aforementioned meaning, namely stands for a group of formula

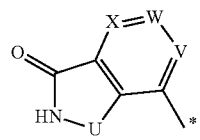

wherein
U stands for nitrogen or carbon,
whereby nitrogen can be substituted with an alkyl substituent,
whereby carbon can be substituted with 1 to 2 alkyl substituents selected independently of one another, or with an oxo substituent,
V stands for nitrogen or carbon,
whereby carbon can be substituted with a substituent selected from the group consisting of halogen, amino, hydroxy, methoxy, methyl and trifluoromethyl,
W stands for nitrogen or carbon,
whereby carbon can be substituted with a substituent selected from the group consisting of halogen, amino, hydroxy, methoxy, methyl and trifluoromethyl,
X stands for nitrogen or carbon,
whereby carbon can be substituted with a substituent selected from the group consisting of halogen, amino, hydroxy, methoxy, methyl and trifluoromethyl, and
* is the point of attachment to the carbon atom,
$R^3$ stands for hydrogen, halogen, amino, trifluoromethyl or (C1-C4)-alkyl,
$R^4$ stands for hydrogen, halogen, (C1-C4)-alkyl or (C1-C4)-alkoxy,
wherein alkyl and alkoxy can be substituted with 1 to 3 fluorine atoms, and
$R^5$ stands for hydrogen, halogen, cyano, (C1-C4)-alkyl, (C3-C6)-cycloalkyl or (C1-C4)-alkoxy,
whereby $R^4$ and $R^5$ cannot simultaneously be hydrogen,
and their salts, their solvates or the solvates of their salts.
Subject matter of the invention are also compounds of formula (Ia), wherein
A has the aforementioned meaning, wherein
U stands for NH or CH2,
V stands for N or CH,
W stands for CH or CMe, wherein CMe stands for C—CH3,
X stands for N or CH, and
* is the point of attachment to the carbon atom,
$R^3$ stands for hydrogen or methyl,
$R^4$ stands for fluorine, difluoromethoxy or trifluoromethoxy, and
$R^5$ stands for fluorine, chlorine, bromine or methoxy,
and their salts, their solvates or the solvates of their salts.
Subject matter of the invention are also compounds of formula (Ia), wherein
A has the aforementioned meaning, wherein
U stands for NH or CH2,
V stands for N or CH,
W stands for CH,
X stands for CH, and
* is the point of attachment to the carbon atom,
$R^3$ stands for hydrogen or methyl,
$R^4$ stands for fluorine, difluoromethoxy or trifluoromethoxy, and
$R^5$ stands for fluorine, chlorine, bromine or methoxy,
and their salts, their solvates or the solvates of their salts.
Subject matter of the invention are also compounds of formula

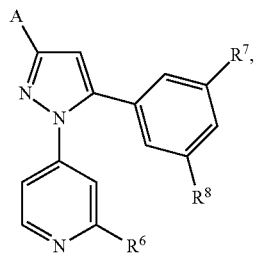

(Ib)

wherein
A has the aforementioned meaning, namely stands for a group of formula

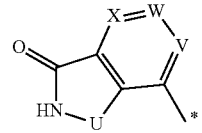

wherein
U stands for nitrogen or carbon,
whereby nitrogen can be substituted with an alkyl substituent,
whereby carbon can be substituted with 1 to 2 alkyl substituents selected independently of one another, or with an oxo substituent,
V stands for nitrogen or carbon,
whereby carbon can be substituted with a substituent selected from the group consisting of halogen, amino, hydroxy, methoxy, methyl and trifluoromethyl,
W stands for nitrogen or carbon,
whereby carbon can be substituted with a substituent selected from the group consisting of halogen, amino, hydroxy, methoxy, methyl and trifluoromethyl, X stands for nitrogen or carbon,
  whereby carbon can be substituted with a substituent selected from the group consisting of halogen, amino, hydroxy, methoxy, methyl and trifluoromethyl, and
  * is the point of attachment to the carbon atom,
$R^6$ stands for hydrogen, halogen, trifluoromethyl, (C1-C4)-alkyl or (C1-C4)-alkoxy,
$R^7$ stands for hydrogen, halogen, (C1-C4)-alkyl or (C1-C4)-alkoxy,
wherein alkyl and alkoxy can be substituted with 1 to 3 fluorine atoms, and
$R^8$ stands for hydrogen, halogen, cyano, (C1-C4)-alkyl, (C3-C6)-cycloalkyl or (C1-C4)-alkoxy,
  whereby $R^7$ and $R^8$ cannot simultaneously be hydrogen,
and their salts, their solvates or the solvates of their salts.

Subject matter of the invention are also compounds of formula (Ib), wherein
A has the aforementioned meaning, wherein
  U stands for NH or CH2,
  V stands for N or CH,
  W stands for CH or CMe, wherein CMe stands for C—CH3,
  X stands for N or CH, and
  * is the point of attachment to the carbon atom,
$R^6$ stands for chlorine, trifluoromethyl methyl or methoxy,
$R^7$ stands for fluorine, methoxy, difluoromethoxy or trifluoromethoxy, and
$R^8$ stands for fluorine, chlorine, bromine or methoxy,
and their salts, their solvates or the solvates of their salts.

Subject matter of the invention are also compounds of formula (Ib), wherein
A has the aforementioned meaning, wherein
  U stands for NH or CH2,
  V stands for N or CH,
  W stands for CH,
  X stands for CH, and
  * is the point of attachment to the carbon atom,
$R^6$ stands for chlorine, trifluoromethyl methyl or methoxy,
$R^7$ stands for fluorine, methoxy, difluoromethoxy or trifluoromethoxy, and
$R^8$ stands for fluorine, chlorine, bromine or methoxy,
and their salts, their solvates or the solvates of their salts.

Subject matter of the invention are also compounds of formula

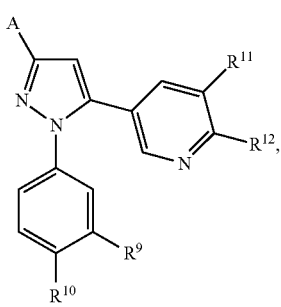

(Ic)

wherein
A has the aforementioned meaning, namely stands for a group of formula

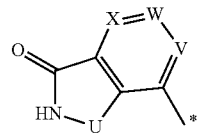

wherein
  U stands for NH or CH2,
  V stands for N or CH,
  W stands for CH or CMe, wherein CMe stands for C—CH3,
  X stands for N or CH, and
  * is the point of attachment to the carbon atom,
$R^9$ stands for hydrogen, halogen, cyano, (C1-C4)-alkyl or (C1-C4)-alkoxy,
  wherein alkyl and alkoxy can be substituted with 1 to 3 fluorine atoms,
$R^{10}$ stands for hydrogen, halogen, trifluoromethyl, (C1-C4)-alkyl or (C1-C4)-alkoxy,
  whereby $R^9$ and $R^{10}$ cannot simultaneously be hydrogen.
$R^{11}$ stands for hydrogen, halogen, cyano, (C1-C4)-alkyl or (C1-C4)-alkoxy,
  wherein alkyl and alkoxy can be substituted with 1 to 3 fluorine atoms, and
$R^{12}$ stands for hydrogen, (C1-C4)-alkyl or halogen,
and their salts, their solvates or the solvates of their salts.

Subject matter of the invention are also compounds of formula

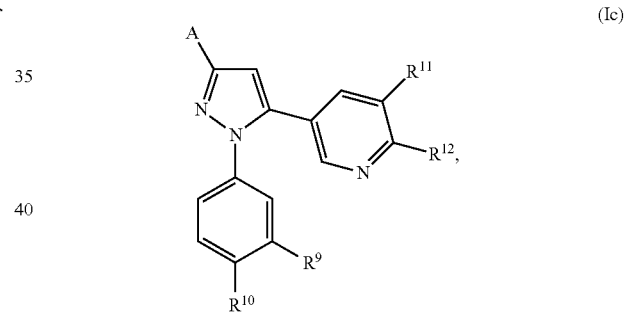

(Ic)

wherein
A has the aforementioned meaning, wherein
  U stands for NH or CH2,
  V stands for N or CH,
  W stands for CH,
  X stands for CH, and
  * is the point of attachment to the carbon atom,
$R^9$ stands for hydrogen, halogen, cyano, (C1-C4)-alkyl or (C1-C4)-alkoxy,
  wherein alkyl and alkoxy can be substituted with 1 to 3 fluorine atoms,
$R^{10}$ stands for hydrogen, halogen, trifluoromethyl, (C1-C4)-alkyl or (C1-C4)-alkoxy,
  whereby $R^9$ and $R^{10}$ cannot simultaneously be hydrogen,
$R^{11}$ stands for hydrogen, halogen, cyano, (C1-C4)-alkyl or (C1-C4)-alkoxy,
  wherein alkyl and alkoxy can be substituted with 1 to 3 fluorine atoms, and
$R^{12}$ stands for hydrogen, (C1-C4)-alkyl or halogen,
and their salts, their solvates or the solvates of their salts.

Subject matter of the invention are also compounds of formula (Id)

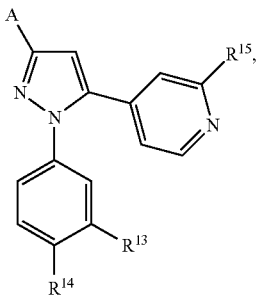

wherein
A has the aforementioned meaning, namely stands for a group of formula

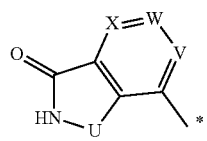

wherein
U stands for NH or CH2,
V stands for N or CH,
W stands for CH or CMe, wherein CMe stands for C—CH3,
X stands for N or CH, and
* is the point of attachment to the carbon atom,
$R^{13}$ stands for hydrogen, halogen, cyano, (C1-C4)-alkyl or (C1-C4)-alkoxy,
wherein alkyl and alkoxy can be substituted with 1 to 3 fluorine atoms,
$R^{14}$ stands for hydrogen, halogen, trifluoromethyl, (C1-C4)-alkyl or (C1-C4)-alkoxy,
whereby $R^{13}$ and $R^{14}$ cannot simultaneously be hydrogen, and
$R^{15}$ stands for hydrogen, halogen, cyano, (C1-C4)-alkyl or (C1-C4)-alkoxy,
wherein alkyl and alkoxy can be substituted with 1 to 3 fluorine atoms,
and their salts, their solvates or the solvates of their salts.

Subject matter of the invention are also compounds of formula (Id)

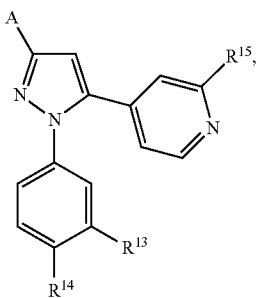

wherein
A has the aforementioned meaning, wherein
U stands for NH or CH2,
V stands for N or CH,
W stands for CH,
X stands for CH, and
* is the point of attachment to the carbon atom,
$R^{13}$ stands for hydrogen, halogen, cyano, (C1-C4)-alkyl or (C1-C4)-alkoxy,
wherein alkyl and alkoxy can be substituted with 1 to 3 fluorine atoms,
$R^{14}$ stands for hydrogen, halogen, trifluoromethyl, (C1-C4)-alkyl or (C1-C4)-alkoxy,
whereby $R^{13}$ and $R^{14}$ cannot simultaneously be hydrogen, and
$R^{15}$ stands for hydrogen, halogen, cyano, (C1-C4)-alkyl or (C1-C4)-alkoxy,
wherein alkyl and alkoxy can be substituted with 1 to 3 fluorine atoms,
and their salts, their solvates or the solvates of their salts.

In some exemplary embodiments of the invention, it can be preferred for A to stand for a group selected from

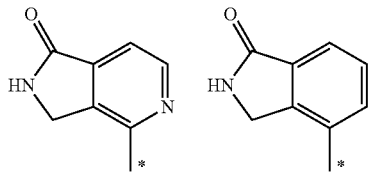

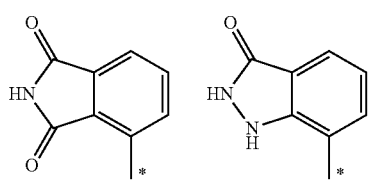

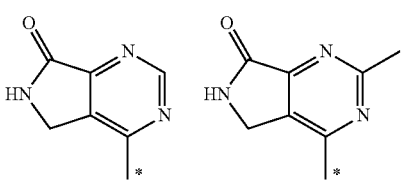

wherein
* is the point of attachment to the carbon atom.

A subject matter of the invention is furthermore a method for the synthesis of the compounds of formulae (I), (Ia), (Ib), (Ic) and (Id), whereby a compound of formula (II)

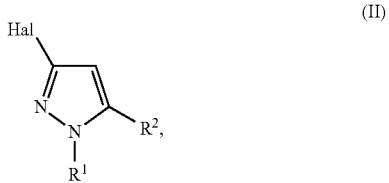

wherein
Hal stands for chlorine, bromine or iodine and
R1 and R2 have the meaning specified above,
is reacted with a compound of formula

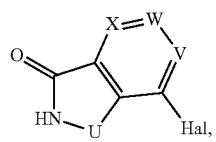
(III)

wherein
Hal stands for chlorine, bromine or iodine and
U, V, W and X have the meaning specified above.

This means that for the production methods in accordance with the invention in accordance with formula (II):
the substituents $R^1$ and $R^2$ can be selected independently of one another from:
$R^1$ stands for phenyl or pyridyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N oxide,
wherein
alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl, and
$R^2$ stands for phenyl or pyridyl,
whereby phenyl is substituted with 1 to 3, preferably 1 to 2 substituents, the substituents being selected independently of one another from the group consisting of halogen, hydroxy, amino, cyano, nitro, (C1-C4)-alkyl, (C3-C6)-cycloalkyl, (C1-C4)-alkylamino and (C1-C4)-alkoxy,
wherein
alkyl, cycloalkyl, alkylamino and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
whereby pyridyl can be substituted with 1 or 2 substituents, the substituents being selected independently of one another from the group consisting of halogen, hydroxy, amino, cyano, nitro, (C1-C4)-alkyl, (C3-C6)-cycloalkyl and (C1-C4)-alkoxy, and whereby the nitrogen atom of the pyridyl can form an N oxide, wherein
alkyl, cycloalkyl and alkoxy in turn may be substituted one to three times identically or differently with radicals selected from the group consisting of halogen, cyano, hydroxy, (C1-C4)-alkoxy, amino, mono-(C1-C4)-alkylamino, di-(C1-C4)-alkylamino, (C3-C7)-cycloalkyl and 4- to 7-membered heterocyclyl,
the substituents U, V, W and X being selected independently of one another from
U stands for nitrogen or carbon,
whereby nitrogen can be substituted with an alkyl substituent,
whereby carbon can be substituted with 1 to 2 alkyl substituents selected independently from one another, or with an oxo substituent;
V stands for nitrogen or carbon,
whereby carbon can be substituted with a substituent selected from the group consisting of halogen, amino, hydroxy, methoxy, methyl and trifluoromethyl;
W stands for nitrogen or carbon,
whereby carbon can be substituted with a substituent selected from the group consisting of halogen, amino, hydroxy, methoxy, methyl and trifluoromethyl;
X stands for nitrogen or carbon,
whereby carbon can be substituted with a substituent selected from the group consisting of halogen, amino, hydroxy, methoxy, methyl and trifluoromethyl.

The conversion generally takes place in two stages in inert solvents, first forming an organo-metallic component, followed by the conversion in the presence of a catalyst complex and a base, preferably in a temperature range from 50° C. to 150° C. under high pressure and the exclusion of oxygen.

The compounds of formulae (I), (Ia), (Ib), (Ic) and (Id) produced in accordance with the method specified above may have protective groups that can be cleaved, in accordance with the conditions known to one skilled in the art, in order to obtain additional compounds of formulae (I), (Ia), (Ib), (Ic) and (Id).

The compounds of formulae (I), (Ia), (Ib), (Ic) and (Id) produced in accordance with the method specified above can be converted into additional compounds of formulae (I), (Ia), (Ib), (Ic) and (Id) by selective oxidation using oxidizing agents known to one skilled in the art.

The production of the compounds in accordance with the invention may be illustrated by the following synthesis diagram.

Synthesis Diagram

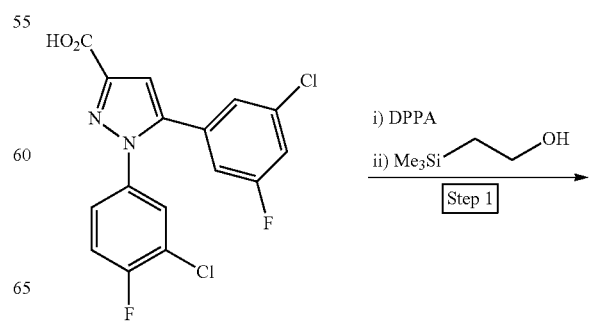

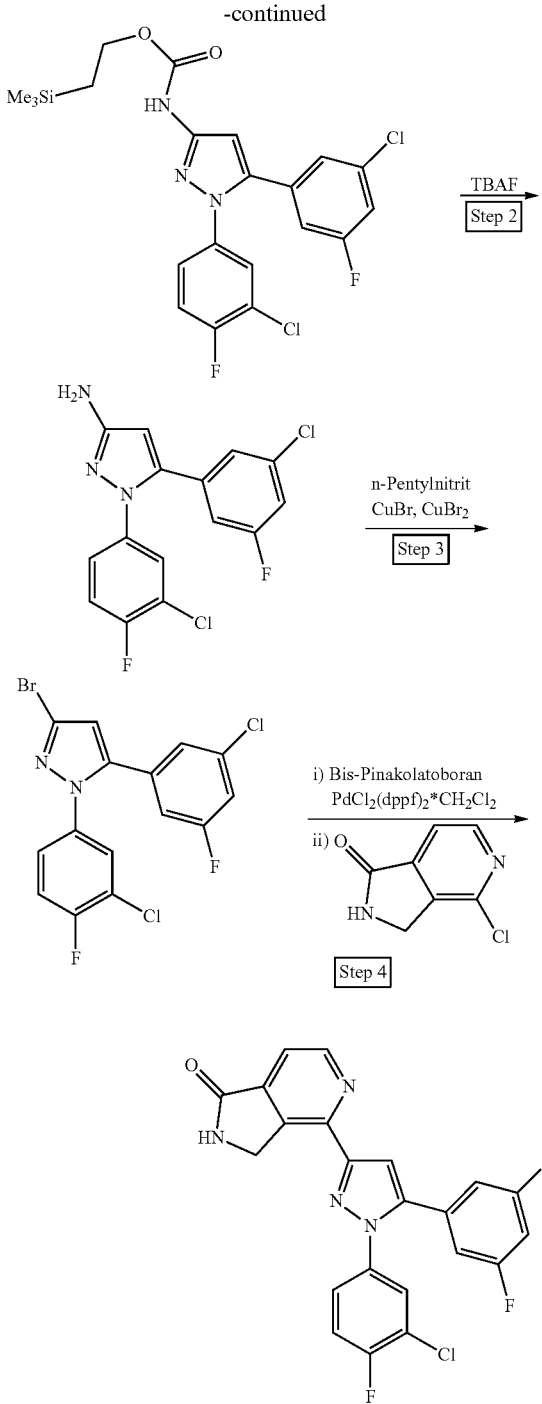

The compounds in accordance with the invention demonstrate a valuable pharmacological action spectrum that cannot be predicted.

They are therefore suitable for use as drugs in a method for treating and/or preventing diseases in humans and animals.

The compounds of the present invention are characterised particularly by an advantageous antiretroviral activity spectrum.

An additional subject matter of the present invention is therefore the use of the compounds in accordance with the invention in a method for treating and/or preventing diseases caused by retroviruses, HI viruses in particular.

A further subject matter of the present invention is the use of the compounds in accordance with the invention in a method for treating and/or preventing diseases, in particular the aforementioned diseases.

A further subject matter of the present invention is the use of the compounds in accordance with the invention to produce a drug for use in methods of treating and/or preventing diseases, in particular the aforementioned diseases.

A further subject matter of the present invention is a method for treating and/or preventing diseases, in particular the aforementioned diseases, using a therapeutically effective amount of the compounds in accordance with the invention.

In this connection, an additional subject matter of the present invention is, in particular, the use of a therapeutically effective quantity of the compounds in accordance with the invention in a method to prevent and/or treat diseases caused by retroviruses, especially those caused by HI viruses.

Among the areas of indication in human medicine, the following may be cited as examples:

1.) The treatment and prevention of human retrovirus infections.
2.) The treatment and prevention of infections and diseases (AIDS) caused by HIV-1 (human immunodeficiency virus; previously known as HTLV III/LAV) and HIV-2, and the stages associated with them, such as ARC (AIDS-related complex) and LAS (lymphadenopathy syndrome) as well as the immunodeficiencies and encephalopathies caused by these viruses.
3.) The treatment of HIV infections caused by simple or multi-resistant HI viruses.

The term "resistant HI viruses" means, for example, HI viruses with resistance to nucleoside RT Inhibitors (NRTI), non-nucleoside RT Inhibitors (NNRTI), integrase inhibitors (II), protease inhibitors (PI) or viruses with resistance to other active principles, e.g. T20 (fusion inhibitors). The term "resistant HI viruses" also means HI viruses with resistance against nucleotide RT inhibitors (NtRTI).

4.) The treatment or prevention of the AIDS-carrier state (AIDS-transmitter state).
5.) The treatment or prevention of an HTLV-I or HTLV-II infection.

In veterinary medicine, the following indications may, for example, be listed:
Infections with
a) Maedi-visna (in sheep and goats)
b) progressive pneumonia virus (PPV) (in sheep and goats)
c) caprine arthritis encephalitis-virus (in sheep and goats)
d) Zwoegerziekte virus (in sheep)
e) infectious anemia virus (in horses)
f) infections caused by the feline leukemia virus
g) infections caused by the feline immunodeficiency virus (FIV)
h) infections caused by the simian immunodeficiency virus (SIV).

Points 2, 3 and 4 above are preferred for the indication area of human medicine. Therefore the indications specified in numbers 2) to 4) are preferred areas for the use of the compounds in accordance with the invention in a method for their prevention and/or treatment.

The substances in accordance with the invention are particularly suitable for use to fight HI viruses with resistances against known non-nucleoside reverse transcriptase inhibitors (NNRTIs) such as efavirenz or nevirapine Therefore, diseases caused by HI viruses that already have resistances against known non-nucleoside RT inhibitors are preferred areas for the use of the compounds in accordance with the invention to prevent and/or treat such diseases.

The compounds in accordance with the invention may be effective systemically and/or locally. For this purpose they may be administered in a suitable manner, such as by oral, parenteral, pulmonary, nasal, sublingual, lingual, buccal, rectal, dermal, transdermal, conjunctival, otic routes or as an implant or stent. The present invention therefore comprises these drug administration routes for the administration of the compounds in accordance with the invention.

The compounds in accordance with the invention can be administered in suitable forms for these drug administration routes.

Means of administration that function in accordance with the state of the art and that release the compounds in accordance with the invention quickly and/or in modified form are suitable for oral administration; said means of administration contain the compounds in accordance with the invention in crystalline and/or amorphized and/or dissolved form, e.g. tablets (non-coated or coated tablets, for example enteric-coated or with coatings that dissolve slowly or are insoluble, which control the release of the compound in accordance with the invention), tablets or film-coated/wafer-like forms that dissolve quickly in the mouth, film-coated forms/lyophilisates, capsules (for example hard or soft gelatin capsules), sugar-coated tablets, granulates, pellets, powder, emulsions, suspensions, aerosols or solutions.

Parenteral administration may take place while circumventing a resorption step (e.g. intravenous, intra-arterial, intracardial, intraspinal or intralumbal routes) or incorporating resorption (e.g. intramuscular, subcutaneous, intracutaneous, percutaneous or intraperitoneal routes). Administration forms suitable for parenteral administration are, among others, injection and infusion preparations in the form of solutions, suspensions, emulsions lyophilisates or sterile powders.

The following means are suitable for the other routes of administration, for example inhalation drugs (e.g. powder inhalers, nebulizers), nose drops, nose solutions, nose sprays; tablets, film-coated/wafer-like medications, or capsules for lingual, sublingual or buccal administration, suppositories, ear or eye preparations, vaginal capsules, aqueous suspensions (lotions, shake mixtures), lipophilic suspensions, ointments, creams, transdermal therapeutic systems (as for example patches), milk, pastes, foams, dusting powder, implants or stents.

The compounds in accordance with the invention can be converted into the above-mentioned forms of administration. This may be done in a known manner through mixing with inert, non-toxic pharmaceutically suitable excipients. The latter include carrier substances (e.g. microcrystalline cellulose, lactose, mannitol), solvents (e.g. liquid polyethylene glycols), emulsifiers and dispersants or wetting agents (for example sodium dodecyl sulfate, polyoxysorbitan oleate), binding agents (e.g. polyvinylpyrrolidone), synthetic and natural polymers (e.g. albumin), stabilizers (e.g. antioxidants such as ascorbic acid), dyes (e.g. inorganic pigments such as iron oxides) and flavour and/or odour correctors.

A further subject matter of the present invention are drugs which contain at least one compound in accordance with the invention, usually together with one or more inert, non-toxic, pharmaceutically suitable excipients, as well as the use thereof for the aforementioned purposes.

In general, it has been shown to be advantageous in both human and veterinary medicine to administer the active ingredients in accordance with the invention in total quantities of 0.1 to 200 mg/kg, preferably 1 to 100 mg/kg of body weight per 24-hour period, potentially in the form of multiple single doses, to achieve the desired result. A single dose preferably contains the active ingredient(s) in quantities from 1 to 80 mg/kg, especially 1 to 30 mg/kg of body weight.

Nonetheless, it can sometimes be necessary to deviate from said quantities, namely depending on body weight, administration route, individual response to the active substance, nature of the preparation and time or interval at which the administration takes place. For example, in certain cases it may be sufficient to get by with less than the aforementioned minimum amount, while in other cases the stated upper limit has to be exceeded. When administering large amounts it may be recommendable to distribute these in several individual doses over the course of a day.

Unless otherwise specified, the percentages in the following tests and examples are given as percentages by weight; parts are parts by weight. Solvent ratios, dilution ratios and concentration readings of liquid/liquid solutions refer in each case to the volume. The notation "w/v" means "weight/volume". Thus for example "10% w/v": means 100 mL solution or suspension contains 10 g substance.

EXAMPLES

Abbreviations bs broad singlet (in NMR)
bd broad boublet (in NMR)
cat. catalytic
CI chemical ionisation (in MS)
CMe C—$CH_3$
dd doublet of doublet (in NMR)
DMF Dimethyl formamide
DMSO Dimethyl sulfoxide
dt doublet of triplet (in NMR)
d. Th. of theoretical yield
EI electron impact ionization (in MS)
eq. equivalent(s)
ESI electrospray-ionisation (in MS)
Et ethyl
ges. saturated
h hour(s)
HPLC high-pressure-, high performance liquid chromatography
conc. concentrated
LC-MS liquid chromatography-mass spectrometry
LHMDS lithium bis(trimethylsilyl)amide
m multiplet (in NMR)
Me methyl
min minute(s)
MS mass spectrometry
NMR nuclear magnetic resonance
Ph phenyl
q quartet (in NMR)
quint quintet (in NMR)
RT room temperature
$R_t$ retention time (in HPLC)
s singlet (in NMR)
TFA trifluoroacetic acid THF tetrahydrofuran
UV ultraviolet spectrometry
wässr. aqueous, aqueous solution A. LC-MS and HPLC Methods Method 1 (LC-MS):
Instrument: Waters ACQUITY SQD UPLC System; Column: Waters Acquity UPLC HSS T3 1.8μ 50 mm×1 mm; Eluent A: 1 l water+0.25 ml 99% formic acid, Eluent B: 1 l acetonitrile+0.25 ml 99% formic acid; Gradient: 0.0 min 90% A→1.2 min 5% A→2.0 min 5% A; Heater: 50° C.; Flow rate: 0.40 ml/min; UV detection: 210-400 nm.

Method 2 (LC-MS):
Instrument: Micromass Quattro Premier with Waters UPLC Acquity; Column: Thermo Hypersil GOLD 1.9μ 50×1 mm; Eluent A: 1 l water+0.5 ml 50% formic acid, Eluent B: 1 l acetonitrile+0.5 ml 50% formic acid; Gradient: 0.0 min 97% A→0.5 min 97% A→3.2 min 5% A→4.0 min 5% A Heater: 50° C.; Flow rate: 0.3 ml/min; UV detection: 210 nm.

Method 3 (LC-MS):
Instrument: Waters ACQUITY SQD UPLC System; Column: Waters Acquity UPLC HSS T3 1.8μ 30 mm×2 mm; Eluent A: 1 l water+0.25 ml 99% formic acid, Eluent B: 1 l acetonitrile+0.25 ml 99% formic acid; Gradient: 0.0 min 90% A→1.2 min 5% A→2.0 min 5% A; Heater: 50° C.; Flow rate: 0.40 ml/min; UV detection: 208-400 nm.

Method 4 (LC-MS):
MS instrument: Waters (Micromass) QM; HPLC instrument: Agilent 1100 Series; Column: Agilent ZORBAX Extend-C18 3.0×50 mm 3.5 micron; Eluent A: 1 l water+0.01 mol ammonium carbonate, Eluent B: 1 l acetonitrile; Gradient: 0.0 min 98% A→0.2 min 98% A→3.0 min 5% A→4.5 min 5% A; Heater: 40° C.; Flow rate: 1.75 ml/min; UV detection: 210 nm.

When purifying compounds in accordance with the invention by preparative HPLC in accordance with the methods described above, in which the eluent contains additives, such as trifluoroacetic acid, formic acid or ammonia, the compounds in accordance with the invention can occur in salt form, such as trifluoroacetate, formate or ammonium salt if the compounds in accordance with the invention contain sufficient basic or acidic functionality. Such a salt can be converted into the corresponding free base or acid by methods known to one skilled in the art.

B. Starting Compounds and Intermediates

The (hetero)arylhydrazine and methyl-(hetero)arylketone used are commercially available or were synthesised using methods known from the literature.

The following references on synthesis of the (hetero)arylhydrazine are cited as examples: K. H. Pilgram, Synthetic Communications, 1985, 15 (8), 697-706; M. T. Makhija, Bioorganic & Medicinal Chemistry, 2004, 12 (9), 2317-2333; A. Reisinger, Organic & Biomolecular Chemistry, 2004, 2 (2), 246-256; V. S. Padalkar, Synthetic Communications, 2011, 41 (6), 925-938; H. Y. Lo, Bioorganic & Medicinal Chemistry Letters, 2010, 20 (22), 6379-6383; M. G. C. Kahn, Bioorganic & Medicinal Chemistry Letters, 2006, 16 (13), 3454-3458; WO 2007/064872; WO 2009/068617; US 2005/0215577; WO 2008/034008; WO 2011/033018.

The following references on synthesis of the methyl-(hetero)arylketone are cited as examples: D. B. Bolstad, Journal of Medicinal Chemistry, 2008, 51 (21), 6839-6852; D. Xu, Tetrahedron Letters, 2008, 49 (42), 6104-6107; M. A. Chowdhury, Journal of Medicinal Chemistry, 2009, 52 (6), 1525-1529; J. Zheng, Chemical Communications, 2007, 48, 5149-5151; US 2009/0209529; WO 2007/064553; WO 2007/031440; WO 2009/077954.

Example 1A

Lithium-1-(3-fluoro-5-trifluoromethoxyphenyl)-4-ethoxy-3,4-dioxobut-1-en-1-olate

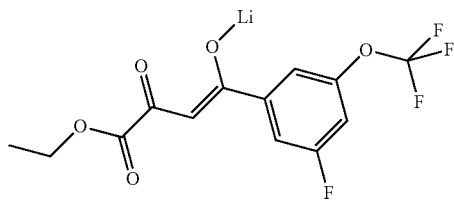

A solution of LHMDS (1 N in THF, 3.11 ml, 3.116 mmol) is diluted with diethyl ether (10 ml) and cooled to −78° C. A solution of 3-fluoro-5-trifluoromethoxy acetophenone (0.60 g, 2.70 mmol) in diethyl ether (5 ml) is added and the reaction mixture is stirred for 45 min at −78° C. Next, diethyloxalate (0.44 ml, 3.24 mmol) is added dropwise at −78° C. and the resulting solution is warmed to RT and stirred at RT overnight. The title compound results after removing the solvent under vacuum and is used in the next step without further purification.

LC-MS (Method 1): Rt=1.19 min; MS (ESIpos): m/z=321 [M−Li+2H]+.

Example 2A

Lithium-1-(3-chloro-5-trifluoromethoxyphenyl)-4-ethoxy-3,4-dioxobut-1-en-1-olate

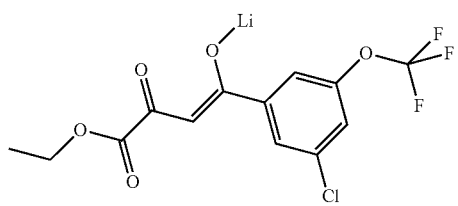

The title compound is produced from 3-chloro-5-trifluoromethoxyacetophenone (1.00 g, 3.56 mmol) and diethyloxalate (0.58 ml, 4.28 mmol) in a manner analogous to the synthesis of the compound from example 1A. The title compound is used in the next step without further purification.

LC-MS (Method 1): Rt=1.29 min; MS (ESIpos): m/z=337 [M−Li]−.

Example 3A

Lithium-1-(3-bromo-5-trifluoromethoxy phenyl)-4-ethoxy-3,4-dioxobut-1-en-1-olate

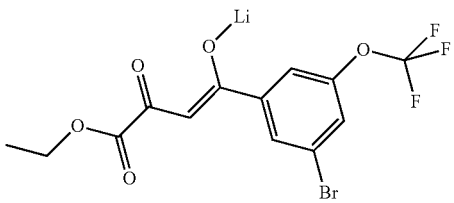

The title compound is produced starting from 3-bromo-5-trifluoromethoxy acetophenone (4.9 g, 17.31 mmol) and diethyl oxalate (2.84 ml, 20.77 mmol) in a manner analogous to the synthesis of the compound from example 1A. This produces 7.12 g (101% of theoretical yield) of the title compound at 95% purity, which is used in the next step without further purification.

LC-MS (Method 1): $R_t$=1.33 min; MS (ESIpos): m/z=381 [M−Li]$^-$.

Example 4A

Lithium-1-(3-difluoromethoxy-5-fluorophenyl)-4-ethoxy-3,4-dioxobut-1-en-1-olate

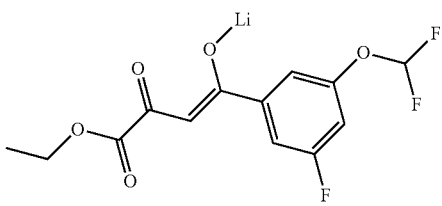

The title compound is produced starting from 3-difluoromethoxy-5-fluoroacetophenone (0.80 g, 3.93 mmol) and diethyl oxalate (0.64 ml, 4.72 mmol) in an analogous manner to synthesis of the compound from example 1A. This produces 1.43 g (117% of theoretical yield) of the compound as a raw product, which is used in the next step without further purification.

LC-MS (Method 1): $R_t$=1.11 min; MS (ESIpos): m/z=303 [M−Li]$^-$.

Example 5A

Lithium-1-(3-chloro-5-difluoromethoxy phenyl)-4-ethoxy-3,4-dioxobut-1-en-1-olate

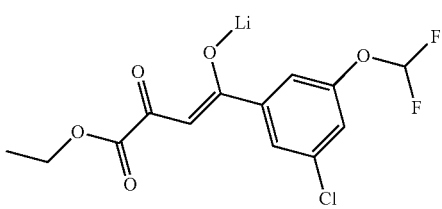

The title compound is produced starting from 3-chloro-5-difluoromethoxy acetophenone (5.00 g, 22.67 mmol) and diethyl oxalate (3.69 ml, 27.20 mmol) in a manner analogous to the synthesis of the compound from example 1A. This produces 8.46 g (114% of theoretical yield) of the title compound as a raw product, which is used in the next step without further purification.

LC-MS (Method 1): $R_t$=1.21 min; MS (ESIpos): m/z=319 [M−Li]$^-$.

Example 6A

Lithium-1-(3-bromo-5-difluoromethoxy phenyl)-4-ethoxy-3,4-dioxobut-1-en-1-olate

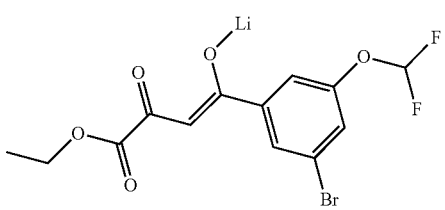

The title compound is produced starting from 3-bromo-5-difluoromethoxy acetophenone (5.00 g, 18.86 mmol) and diethyl oxalate (3.09 ml, 21.69 mmol) in a manner analogous to the synthesis of the compound from example 1A. This produces 6.95 g (99% of theoretical yield) of the title compound as a raw product, which is used in the next step without further purification.

LC-MS (Method 1): $R_t$=1.24 min; MS (ESIpos): m/z=363 [M−Li]$^-$.

Example 7A

Lithium-1-(3-chloro-5-fluorophenyl)-4-ethoxy-3,4-dioxobut-1-en-1-olate

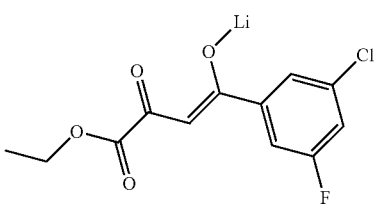

A solution of LHMDS (1 N in THF, 14 ml, 14 mmol) is diluted with diethyl ether (7 ml) and cooled to −78° C. A solution of 3-chloro-5-fluoroacetophenone (2.1 g, 12.2 mmol) in diethyl ether (18 ml) is added and the mixture is stirred for 45 min at −78° C. Diethyl oxalate (2 ml, 14.6 mmol) is then added dropwise at −78° C., warmed to RT, and the reaction mixture is stirred overnight at RT. After removing the solvent under vacuum, this produces 3.9 g of the title compound at 85% purity (115% of theoretical yield), which is used in the next step without further purification.

LC-MS (Method 1): $R_t$=1.19 min; MS (ESIpos): m/z=272 [MLi+2H]$^+$.

Example 8A 1-(3-chloro-4-fluorophenyl)-5-(3-fluoro-5-trifluoromethoxyphenyl)-1H-pyrazole-3-carboxylic acid

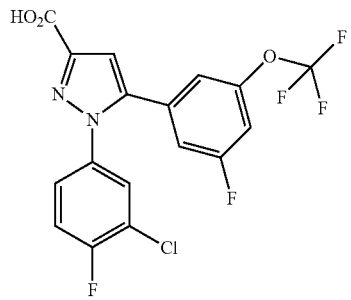 [SMILES: O=C(O)c1cc(-c2cc(F)cc(OC(F)(F)F)c2)n(-c2ccc(F)c(Cl)c2)n1]

A solution of the compound from example 1A (886 mg, 2.7 mmol) and 0.59 g (2.97 mmol) 3-chloro-4-fluorophenylhydrazine hydrochloride in 10 ml ethanol is stirred for 3 hours at RT. The ethanol is removed under vacuum and the residue dissolved in 10 ml glacial acetic acid. The solution is stirred for 2 hours under reflux and the solvent is then removed under vacuum. The residue is dissolved in a mixture of methanol/acetonitrile/water and purified using preparative HPLC (developing solvent: methanol/Milli-Q water/trifluoroacetic acid (anhydrous) 15:80:5). This produces 1.18 g (80% of theoretical yield, 82% purity) of the ethyl ester of the title compound as an intermediate.

The intermediate is dissolved in 30 mL THF and 10 ml water, and 0.91 g (21.72 mmol) lithiumhydroxide monohydrate is added. The reaction mixture is stirred at RT overnight, acidified with 1N hydrochloric acid and extracted using dichloromethane. The organic phase is washed with water, dried using sodium sulfate, filtered and evaporated under vacuum. The residue is stirred together with ether/pentane, filtered and dried. This produces 0.73 g (78% of theoretical yield) of the title compound.

$^1$H-NMR (400 MHz, DMSO-d$_6$): δ=7.00 (s, 1H), 7.29 (s, 1H), 7.37-7.50 (m, 3H), 7.55 (t, 1H), 7.76 (dd, 1H), 13.15 (bs, 1H).

LC-MS (Method 1): $R_t$=1.11 min; MS (ESIpos): m/z=419 [M+H]$^+$.

Example 9A 1-(3-chloro-4-fluorophenyl)-5-(3-chloro-5-trifluoromethoxyphenyl)-1H-pyrazole-3-carboxylic acid

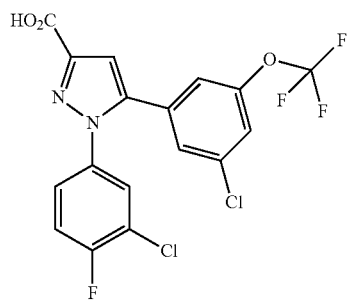

The compound from example 2A (1.22 g, 3.56 mmol) is reacted with 0.77 g (3.92 mmol) 3-chloro-4-fluorophenylhydrazine hydrochloride in a manner analogous to the synthesis of the compound from example 8A. After processing and separating the raw product by way of HPLC (solvent: acetonitrile-water gradient), this produces 1.13 g (68% of theoretical yield) of the ethyl ester of the title compound as an intermediate.

0.94 g (2.03 mmol) of the intermediate is provided in 21 ml THF and a solution of 0.85 g (20.33 mmol) lithium hydroxide monohydrate in 7 ml water is added. The reaction mixture is stirred overnight at RT, acidified with 1N muriatic acid and diluted with ethyl acetate. The aqueous phase is separated and discarded. The organic phase is washed twice with water and once with saturated sodium chloride solution, dried using sodium sulfate and evaporated under vacuum. The residue is stirred together with ether/pentane, filtered and dried. This produces 0.83 g (94% of theoretical yield) of the title compound.

$^1$H-NMR (400 MHz, DMSO-d$_6$): δ=7.11 (s, 1H), 7.31 (s, 1H), 7.37-7.43 (m, 1H), 7.56 (t, 1H), 7.61-7.66 (m, 2H), 7.77 (dd, 1H), 13.17 (bs, 1H).

LC-MS (Method 1): $R_t$=1.21 min; MS (ESIpos): m/z=435 [M+H]$^+$.

Example 10A 1-(3-chloro-4-fluorophenyl)-5-(3-bromo-5-trifluoromethoxyphenyl)-1H-pyrazole-3-carboxylic acid

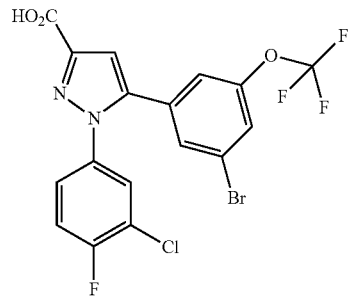 [SMILES: O=C(O)c1cc(-c2cc(Cl)cc(OC(F)(F)F)c2)n(-c2ccc(F)c(Cl)c2)n1]

The compound from example 3A (2.50 g, 6.11 mmol, 95% purity) is converted in a manner analogous to the synthesis of the compound from example 8A with 1.8 g (9.16 mmol) 3-chloro-4-fluorophenylhydrazine hydrochloride. After processing and separating the raw product using column chromatography over silica gel (solvent: dichloromethane→dichloromethane/methanol 98:2), one obtains 2.68 g (87% of theoretical yield) of the ethyl ester of the title compound as an intermediate.

The intermediate is saponified in a manner analogous to the synthesis of the compound from example 8A with 2.22 g (52.79 mmol) lithium hydroxide monohydrate. This produces 2.17 g (86% of theoretical yield) of the title compound.

$^1$H-NMR (400 MHz, DMSO-d$_6$): δ=7.15 (s, 1H), 7.31 (s, 1H), 7.37-7.43 (m, 1H), 7.56 (t, 1H), 7.73-7.79 (m, 3H), 13.16 (bs, 1H).

LC-MS (Method 1): $R_t$=1.21 min; MS (ESIpos): m/z=479 [M+H]$^+$.

Example 11A 1-(3-chloro-4-fluorophenyl)-5-(3-fluoro-5-difluoromethoxyphenyl)-1H-pyrazole-3-carboxylic acid

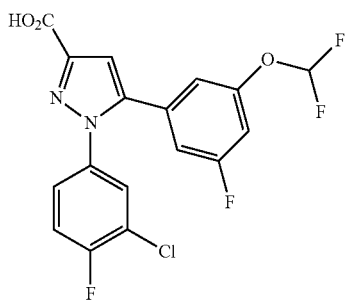 [SMILES: O=C(O)c1cc(-c2cc(F)cc(OC(F)F)c2)n(-c2ccc(F)c(Cl)c2)n1]

The compound from example 4A (0.57 g, 1.84 mmol) is converted in a manner analogous to the synthesis of the compound from example 8A with (0.54 g, 2.75 mmol) 3-chloro-4-fluorophenylhydrazine hydrochloride. The reaction solution is then mixed with ethyl acetate and washed twice with water, twice with saturated sodium hydrogen carbonate solution and once with saturated sodium sulfate and evaporated under vacuum. After separating the raw product by means of preparative HPLC (solvent: acetonitrile-water gradient), this produces 0.41 g (52% of theoretical yield) of the ethyl ester of the title compound as an intermediate.

The intermediate product is hydrolyzed in a manner analogous to the synthesis of the compound from example 8A with 0.40 g (9.52 mmol) of lithium hydroxide monohydrate. This produces 0.34 g (88% of theoretical yield) of the title compound.

$^1$H-NMR (400 MHz, DMSO-d$_6$): δ=6.94 (s, 1H), 7.05-7.14/7.17-7.27 (je m, 4H), 7.33-7.40 (m, 1H), 7.54 (t, 1H), 7.77 (dd, 1H), 13.16 (bs, 1H).

LC-MS (Method 1): R$_t$=1.03 min; MS (ESIpos): m/z=401 [M+H]$^+$.

Example 12A 1-(2-chloropyridine-4-yl)-5-(3-chloro-5-difluoromethoxyphenyl)-1H-pyrazole-3-carboxylic acid

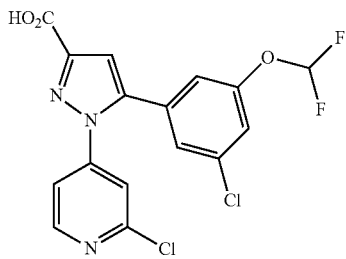 [SMILES: O=C(O)c1cc(-c2cc(Cl)cc(OC(F)F)c2)n(-c2ccnc(Cl)c2)n1]

The compound from example 5A (2.00 g, 6.12 mmol) is reacted in a manner analogous to the synthesis of the compound from example 8A with 1.65 g (9.19 mmol) of 2-chloropyridine-4-yl-hydrazine hydrochloride. The reaction solution is then mixed with ethyl acetate and washed twice with water, twice with saturated sodium bicarbonate and once with saturated sodium chloride solution, dried using sodium sulfate and evaporated under vacuum. After separation of the raw product using preparative HPLC (solvent: water/acetonitrile gradient) and column chromatography over silica gel (solvent: cyclo-hexane/ethyl acetate 3:1) this produces 1.09 g (41% of theoretical yield) of the ethyl ester of the title compound as an intermediate product.

The intermediate product 0.76 g (1.78 mmol) is hydrolyzed in a manner analogous to the synthesis of the compound from example 8A with 0.74 g (17.75 mmol) of lithium hydroxide monohydrate. This produces 0.64 g (90% of theoretical yield) of the title compound.

$^1$H-NMR (400 MHz, DMSO-d$_6$): δ=7.18 (s, 1H), 7.28 (s, 1H), 7.29 (t, 1H), 7.32 (dd, 1H), 7.42 (s, 1H), 7.44-7.47 (m, 1H), 7.57 (d, 1H), 8.48 (d, 1H), 13.36 (bs, 1H).

LC-MS (Method 1): R$_t$=0.96 min; MS (ESIpos): m/z=400 [M+H]$^+$.

Example 13A 1-(2-chloropyridine-4-yl)-5-(3-bromo-5-difluoromethoxyphenyl)-1H-pyrazole-3-carboxylic acid

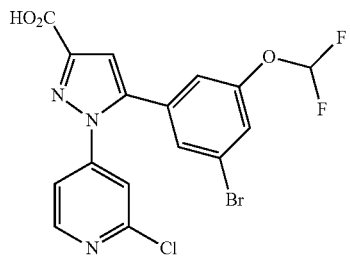 [SMILES: O=C(O)c1cc(-c2cc(Br)cc(OC(F)F)c2)n(-c2ccnc(Cl)c2)n1]

The compound from example 6A (2.80 g, 7:54 mmol) is reacted (31.11 mmol) in a manner analagous to the synthesis of the compound from example 8A with 2.04 g of 3-chloro-4-fluorophenyl hydrazine hydrochloride. The reaction solution is then mixed with ethyl acetate and dried twice with water, twice with saturated sodium bicarbonate solution and once with saturated sodium chloride solution using sodium sulfate and evaporated under vacuum. After separation of the raw product by preparative HPLC (solvent: water/acetonitrile gradient) 2.32 g (65% of theoretical yield) of the ethyl ester of the title compound is produced as an intermediate product.

The intermediate product 2.28 g (4.83 mmol) is hydrolyzed in a manner analogous to the synthesis of the compound from example 8A with 2.03 g (48.28 mmol) lithium hydroxide monohydrate. This produces 2.03 g (94% of theoretical yield) of the title compound.

$^1$H-NMR (400 MHz, DMSO-d$_6$): δ=7.21 (s, 1H), 7.29 (s, 1H), 7.29 (t, 1H), 7.33 (dd, 1H), 7.51-7.60 (m, 3H), 8.48 (d, 1H), 13.36 (bs, 1H).

LC-MS (Method 3): R$_t$=1.02 min; MS (ESIpos): m/z=444 [M+H]$^+$.

Example 14A 5-(3-chloro-5-fluorophenyl)-1-(pyridine-3-yl)-1H-pyrazole-3-carboxylic acid

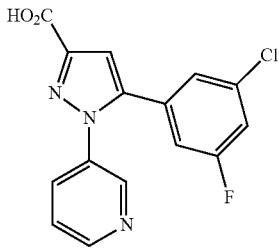 [SMILES: O=C(O)c1cc(-c2cc(F)cc(Cl)c2)n(-c2cccnc2)n1]

807 mg (2.90 mmol) of the compound from example 7A is reacted with 464 mg (3.19 mmol) 3-pyridylhydrazine hydrochloride in a manner analogous to the synthesis of the compound from example 8A. Following hydrolysis, 353 mg (38% of theoretical yield) of the title compound is produced.

$^1$H-NMR (400 MHz, DMSO-$d_6$): δ=7.19 (d, 1H), 7.25 (d, 2H), 7.48-7.59 (m, 2H), 7.85 (d, 1H), 8.58 (d, 1H), 8.66 (d, 1H); COOH not detectable.

LC-MS (Method 1): $R_t$=0.81 min; MS (ESIpos): m/z=318 [M+H]$^+$.

Example 15A 5-(3-fluoro-5-trifluoromethoxyphenyl)-1-(pyridine-3-yl)-1H-pyrazole-3-carboxylic acid

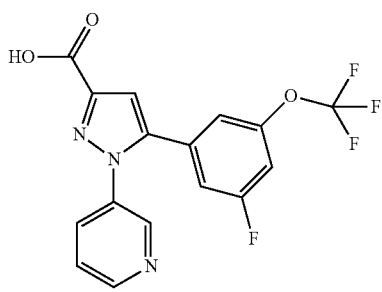 [SMILES: O=C(O)c1cc(-c2cc(F)cc(OC(F)(F)F)c2)n(-c2cccnc2)n1]

1.82 g (4.71 mmol) of the compound from example 1A is reacted with 1.03 g (7.07 mmol) 3-pyridylhydrazine hydrochloride in a manner analogous to the synthesis of the compound from example 8A. Following hydrolysis, 1.12 g (65% of theoretical yield) of the title compound is produced.

$^1$H-NMR (400 MHz, DMSO-$d_6$): δ=7.03 (s, 1H), 7.32 (s, 1H), 7.41 (d, 1H), 7.48 (d, 1H), 7.55 (dd, 1H), 7.83-7.89 (m, 1H), 8.58 (d, 1H), 8.67 (dd, 1H), 13.20 (bs, 1H).

LC-MS (Method 1): $R_t$=0.87 min; MS (ESIpos): m/z=368 [M+H]$^+$.

Example 16A 5-(3-chloro-5-trifluoromethoxyphenyl)-1-(pyridine-3-yl)-1H-pyrazole-3-carboxylic acid

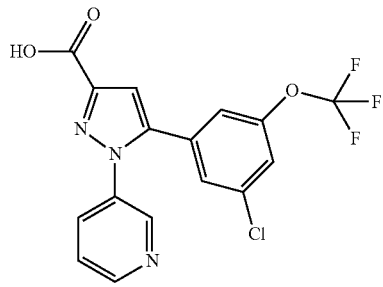 [SMILES: O=C(O)c1cc(-c2cc(Cl)cc(OC(F)(F)F)c2)n(-c2cccnc2)n1]

500 mg (1.23 mmol) of the compound from example 2A is reacted with 197 mg (1.36 mmol) 3-pyridylhydrazine hydrochloride in a manner analogous to the synthesis of the compound from example 8A. Following hydrolysis, 203 mg (43% of theoretical yield) of the title compound is produced.

$^1$H-NMR (400 MHz, DMSO-$d_6$): δ=7.16 (s, 1H), 7.34 (s, 1H), 7.55 (dd, 1H), 7.58-7.61 (m, 2H), 7.64 (s, 1H), 7.86 (dt, 1H), 8.67 (dd, 1H), 13.19 (bs, 1H).

LC-MS (Method 3): $R_t$=0.98 min; MS (ESIpos): m/z=384 [M+H]$^+$.

Example 17A 5-(3-bromo-5-trifluoromethoxyphenyl)-1-(pyridine-3-yl)-1H-pyrazole-3-carboxylic acid

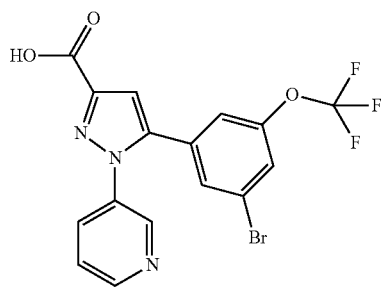 [SMILES: O=C(O)c1cc(-c2cc(Br)cc(OC(F)(F)F)c2)n(-c2cccnc2)n1]

1.10 g (2.40 mmol) of the compound from example 3A is reacted with 525 mg (3.61 mmol) 3-pyridylhydrazine hydrochloride in a manner analogous to the synthesis of the compound from example 8A. Following hydrolysis, 557 mg (54% of theoretical yield) of the title compound is produced.

$^1$H-NMR (400 MHz, DMSO-$d_6$): δ=7.19 (s, 1H), 7.29 (s, 1H), 7.51 (dd, 1H), 7.66-7.72 (m, 2H), 7.84 (d, 1H), 8.11 (dt, 1H), 8.32 (d, 1H), 13.20 (bs, 1H).

LC-MS (Method 1): $R_t$=1.04 min; MS (ESIpos): m/z=428 [M+H]$^+$.

Example 18A 5-(3-fluoro-5-difluoromethoxyphenyl)-1-(pyridine-3-yl)-1H-pyrazole-3-carboxylic acid

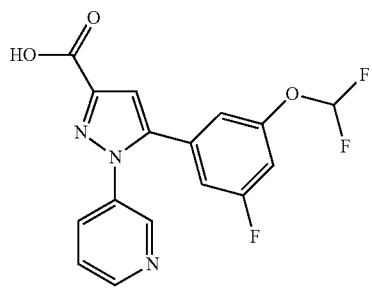 [SMILES: O=C(O)c1cc(-c2cc(F)cc(OC(F)F)c2)n(-c2cccnc2)n1]

590 mg (1.01 mmol) of the compound from example 4A is reacted with 161 mg (1.11 mmol) 3-pyridylhydrazine hydrochloride in a manner analogous to the synthesis of the compound from example 8A. Following hydrolysis, 150 mg (43% of theoretical yield) of the title compound is produced.

$^1$H-NMR (400 MHz, DMSO-d$_6$): δ=6.96 (s, 1H), 7.05-7.11 (m, 1H), 7.21 (dt, 1H), 7.25 (t, 1H), 7.27 (s, 1H), 7.55 (dd, 1H), 7.83-7.89 (m, 1H), 8.58 (d, 1H), 8.66 (dd, 1H), 13.19 (bs, 1H).

LC-MS (Method 3): R$_t$=0.83 min; MS (ESIpos): m/z=350 [M+H]$^+$.

Example 19A 5-(3-chloro-5-difluoromethoxyphenyl)-1-(pyridine-3-yl)-1H-pyrazole-3-carboxylic acid

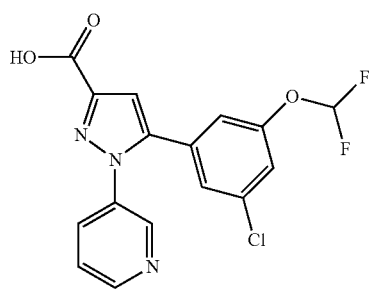 [SMILES: O=C(O)c1cc(-c2cc(Cl)cc(OC(F)F)c2)n(-c2cccnc2)n1]

350 mg (0.80 mmol) of the compound from example 5A is reacted with 128 mg (0.88 mmol) 3-pyridylhydrazine hydrochloride in a manner analogous to the synthesis of the compound from example 8A. Following hydrolysis, 176 mg (60% of theoretical yield) of the title compound is produced.

$^1$H-NMR (400 MHz, DMSO-d$_6$): δ=7.06-7.09 (m, 1H), 7.25 (t, 1H), 7.26-7.30 (m, 2H), 7.38 (t, 1H), 7.55 (dd, 1H), 7.84-7.89 (m, 1H), 8.59 (d, 1H), 8.67 (dd, 1H), 13.18 (bs, 1H).

LC-MS (Method 1): R$_t$=0.85 min; MS (ESIpos): m/z=366 [M+H]$^+$.

Example 20A 5-(3-bromo-5-difluoromethoxyphenyl)-1-(pyridine-3-yl)-1H-pyrazole-3-carbonic acid

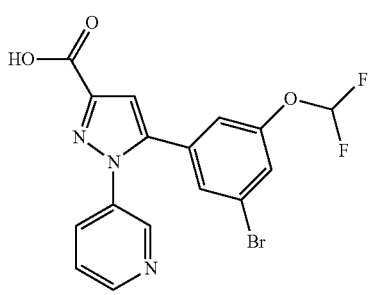 [SMILES: O=C(O)c1cc(-c2cc(Br)cc(OC(F)F)c2)n(-c2cccnc2)n1]

247 mg (0.67 mmol) of the compound from example 6A is reacted with 145 mg (1.00 mmol) 3-pyridylhydrazine hydrochloride in a manner analogous to the synthesis of the compound from example 8A. Following hydrolysis, 51 mg (19% of theoretical yield) of the title compound is produced.

$^1$H-NMR (400 MHz, DMSO-d$_6$): δ=7.11 (s, 1H), 7.25 (t, 1H), 7.29 (s, 1H), 7.39 (t, 1H), 7.49 (t, 1H), 7.56 (dd, 1H), 7.83-7.89 (m, 1H), 8.58 (d, 1H), 8.67 (dd, 1H), 13.17 (bs, 1H).

LC-MS (Method 1): R$_t$=0.87 min; MS (ESIpos): m/z=410 [M+H]$^+$.

The following pyrazole carboxylic acid was prepared in accordance with the referenced literature:

| | Structure | Reference |
|---|---|---|
| Example 21A | HO$_2$C structure with pyrazole, 3,5-dichloro-4-fluorophenyl and 3-chloro-5-fluorophenyl substituents | WO 2009/115213 Example 71A |

Example 22A 4-chloro-2,3-dihydro-1H-pyrrolo[3,4-c]pyridine-1-one

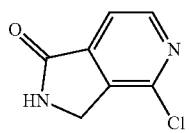 [SMILES: O=C1NCc2c1ccnc2Cl]

1.50 g (7.51 mmol) 2-chloro-3-methyl-4-pyridine carboxylic acid ethyl-ester, 1.74 g (9.77 mmol) N-bromosuccinimide and 0.11 g (0.68 mmol) 2,2'-azobis-2-methyl-proprionitrile are dissolved in tetrachloromethane and stirred for 5 h under reflux. The resulting solid is filtered off and discarded. The filtrate is washed with water, the aqueous phase is extracted using dichloromethane, and the combined organic phases are evaporated in a rotary evaporator. The raw product is separated by column chromatography over silica gel (dichloromethane→dichloromethane/methanol 99:1). This produces 2.11 g (94% of theoretical yield, 93% purity) of the brominated intermediate.

1.50 g (5.39 mmol, 93% purity) of the brominated intermediate is dissolved in 20 ml acetonitrile, and mixed with 15 ml of a 20% solution of ammonia and water, and the reaction mixture is stirred for 2 h at RT. The fine precipitate is filtered off and dried under high vacuum. After unifying both fractions, 1.36 g of the title compound is produced (quantitative yield, contaminated by ammonium bromide salt).

$^1$H-NMR (400 MHz, DMSO-d$_6$): δ=4.47 (s, 2H), 7.72 (d, 1H), 8.57 (d, 1H), 9.18 (s, 1H).

LC-MS (Method 1): R$_t$=0.38 min; MS (ESIpos): m/z=169 [M+H]$^+$.

Example 23A 4-chloro-5,6-dihydro-7H-pyrrolo[3,4-d]pyrimidine-7-one

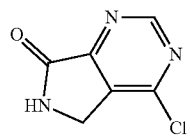 [SMILES: O=C1NCc2c(Cl)ncnc21]

1.00 g (5.36 mmol) methyl-6-chloro-5-methylpyrimidine-4-carboxylate, 0.95 g (5.36 mmol) N-bromosuccinimide and 79 mg (0.48 mmol) 2,2'-azobis-2-methylpropanenitrile were dissolved in 7 ml 1,2-dichlorethane and stirred for 2 hours under reflux. Over the course of 4 hours 0.76 g (4.29 mmol) N-bromosuccinimide was added under reflux. The reaction mixture was mixed with ethyl acetate and washed successively with water, twice with saturated sodium thiosulphate solution, again with water and then with a saturated sodium chloride solution. The organic phase was dried using sodium sulfate, filtered and the solution evaporated in a rotary evaporator. The raw product was dissolved in a small amount of acetonitrile; the solution was filtered through a Millipore syringe filter and separated using preparative HPLC (solvent: acetonitrile/water gradient). This produces 708 mg (48% of theoretical yield) of brominated intermediates.

689 mg (2.60 mmol) of the brominated intermediates was dissolved in 2.2 ml of acetonitrile at 0° C., mixed with 0.4 ml (2.60 mmol) of a 20% solution of ammonia in water and the reaction mixture was warmed to room temperature. It was briefly stirred at 0° C. The precipitate was then filtered out, washed twice with cold acetonitrile and dried under high vacuum. This produced 424 mg of the title compound (95% of theoretical yield, contaminated by ammonium bromide salt).

$^1$H-NMR (400 MHz, DMSO-d$_6$): δ=4.50 (s, 2H), 9.23 (s, 1H), 9.55 (s, 1H).

LC-MS (Method 4): R$_t$=0.92 min; MS (ESIpos): m/z=170 [M+H]$^+$.

Example 24A 4-chloro-2-methyl-5,6-dihydro-7H-pyrrolo[3,4-d]pyrimidine-7-one

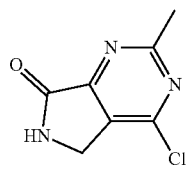

0.99 g (4.62 mmol) ethyl-6-chloro-2,5-dimethylpyrimidine-4-carboxylate, 0.82 g (4.62 mmol) N-bromosuccinimide and 68 mg (0.42 mmol) 2,2'-azobis-2-methylpropanenitrile were dissolved in 6 ml 1,2-dichloroethane and stirred for 2 hours under reflux. Over the course of 4 hours a further 0.66 g (3.70 mmol) N-bromosuccinimide was added under reflux. The reaction mixture was mixed with ethyl acetate and successively washed with water, twice with saturated sodium thiosulphate solution, again with water and then with saturated sodium chloride solution. The organic phase was dried using sodium sulfate, filtered, and the solution was evaporated in a rotary evaporator. The raw product was dissolved in a small amount of acetonitrile, the solution was filtered through a Millipore syringe filter and separated by preparative HPLC (solvent: acetonitrile/water gradient). This produced 618 mg (45% of theoretical yield) of brominated intermediates.

600 mg (2.04 mmol) of the brominated intermediate was dissolved at 0° C. in 1.75 ml acetonitrile mixed with 0.3 ml (2.04 mmol) of a 20% solution of ammonia in water and the reaction mixture was warmed up to room temperature. At 0° C. it was briefly stirred. Then the precipitate was filtered off, washed twice with cold acetonitrile and dried under high vacuum. This produced 421 mg of the title compound (quantitative yield, contaminated by ammonium bromide salt).

$^1$H-NMR (400 MHz, DMSO-d$_6$): δ=2.74 (s, 3H), 4.45 (s, 2H), 9.48 (s, 1H).

LC-MS (Method 1): R$_t$=0.39 min; MS (ESIpos): m/z=184 [M+H]$^+$.

C. Exemplary Embodiments

The described pyrazole carboxylic acid intermediates are converted into the target compounds using a four-step sequence. The following synthesis diagram shows the exemplary conversion.

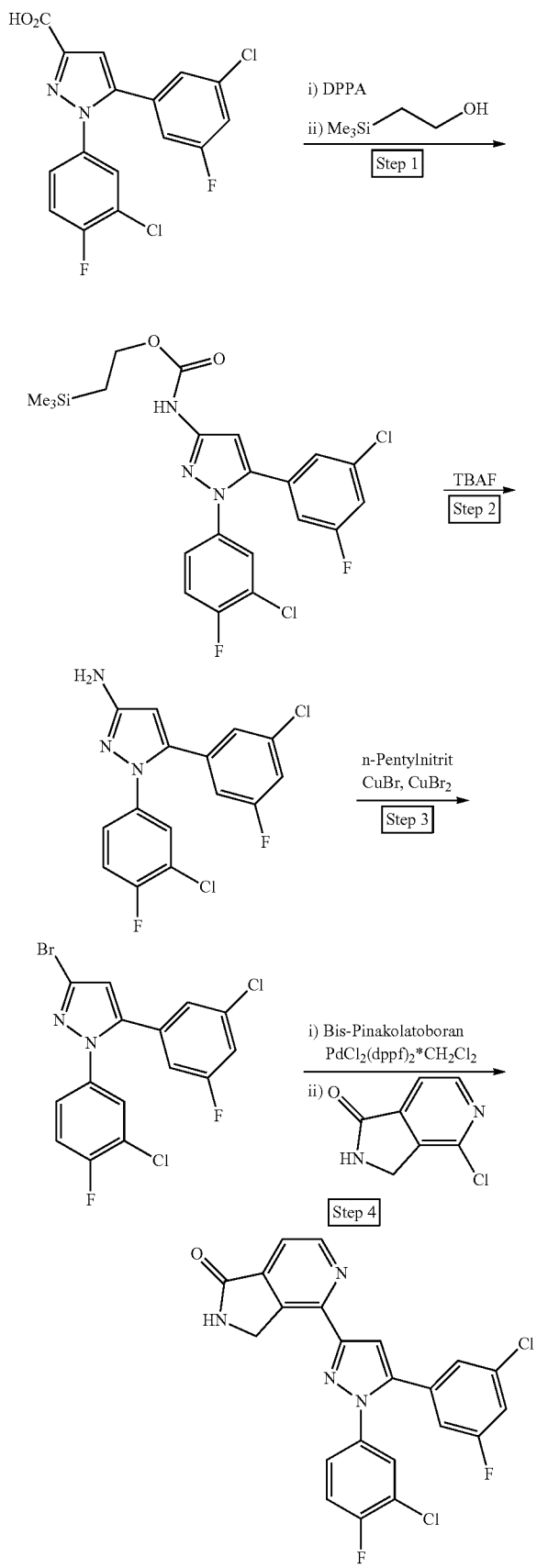

Example 1

4-[1-(3-chloro-4-fluorophenyl)-5-(3-chloro-5-fluorophenyl)-1H-pyrazole-3-yl]-2,3-dihydro-1H-pyrrolo[3,4-c]pyridine-1-one

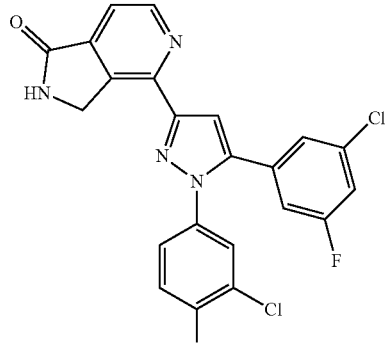

Step 1

A solution of 10.00 g (27.09 mmol) of the pyrazole carboxylic acid from example 21A is mixed in 250 ml of dioxane, mixed with 11.7 ml (54.18 mmol) diphenyl phosphorazidate and 5.7 ml (40.63 mmol) triethylamine, and the reaction mixture is stirred for 1 hour at 50° C. After adding 19.4 ml (135.44 mmol) 2-(trimethylsilyl) ethanol, the reaction mixture is stirred for 2 hours under reflux, mixed with water, and the phases are separated. The aqueous phase is extracted twice with ethyl acetate, and the combined organic phases are dried using sodium sulfate, filtered and evaporated under vacuum until dryness. The raw product is separated using column chromatography over silica gel (cyclohexane/ethyl acetate 10:1). This produces 13.02 g (85% of theoretical yield, 86% purity) of trimethylsilyl ethyl carbamate.

Step 2

12.81 g (22.7 mmol, 86% purity) of the product from step 1 is dissolved in 300 ml tetrahydrofuran and mixed with tetra-n-butylammonium fluoride (1N in THF, 45.4 ml, 45.4 mmol). The reaction mixture is stirred for 3 h at 50° C., the solvent is extracted under vacuum and the residue is absorbed in ethyl acetate and washed with water. The organic phase is dried using sodium sulfate, the sodium sulfate is filtered off and the filtrate is evaporated under vacuum until dryness. The residue is stirred with cyclohexane/ether/pentane. The precipitated solid is filtered off and dried under high vacuum. This produces 5.83 g (76% of theoretical yield) of aminopyrazole.

Step 3

A solution of 1.01 g (7.06 mmol) copper(I)bromide, 1.17 ml (8.82 mmol) N-pentyl nitrite and 2 mg (0.01 mmol) copper (II)bromide in 150 ml acetonitrile is provided and mixed slowly dropwise with a solution of 2.00 g (5.88 mmol) of the compound from step 2 in 50 ml acetonitrile. The reaction mixture is stirred for 2 hours at room temperature, the phases are separated and the aqueous phase is extracted twice with dichloromethane. The combined organic phases are evaporated under vacuum until dryness and the raw product is purified using preparative HPLC (solvent: acetonitrile/water gradient). This produces 0.95 g (39% of theoretical yield) of bromopyrazole.

Step 4

100 mg (0.25 mmol) of the product from step 3 is dissolved in 5 ml of dioxane and mixed with 75 mg (0.30 mmol)

bis-pinakolato-diboron, 73 mg (0.74 mmol) potassium acetate and 12 mg (0.02 mmol) [1,1-bis-(diphenylphosphino) ferrocene]-dichloropalladium dichlormethane complex. The reaction mixture is stirred for 1 hour in the microwave at 120° C., cooled down to RT, mixed with 63 mg (0.37 mmol) of the compound from example 22A, 0.25 ml sodium carbonate solution (2 N in water, 0.50 mmol) and 10 mg (0.01 mmol) [1,1-bis-(diphenylphosphino)ferrocene]-dichloropalladium-dichlormethane complex and mixed for 2 hours at 120° C. The reaction mixture is filtered through a Millipore syringe filter, mixed with DMSO, and separated twice using preparative HPLC (solvent: acetonitrile/water gradient). This produces 42 mg (37% of theoretical yield) of the title compound.

$^1$H-NMR (400 MHz, DMSO-$d_6$): δ=4.81 (s, 2H), 7.24-7.29 (m, 1H), 7.32-7.35 (m, 1H), 7.37-7.42 (m, 1H), 7.49-7.59 (m, 3H), 7.69 (d, 1H), 7.87 (dd, 1H), 8.82 (d, 1H), 9.06 (s, 1H).

LC-MS (Method 1): $R_t$=1.19 min; MS (ESIpos): m/z=457 [M+H]$^+$.

Example 2

4-[5-(3-chloro-5-fluorophenyl)-1-(pyridine-3-yl)-1H-pyrazole-3-yl]-2,3-dihydro-1H-pyrrolo[3,4-c]pyridine-1-one

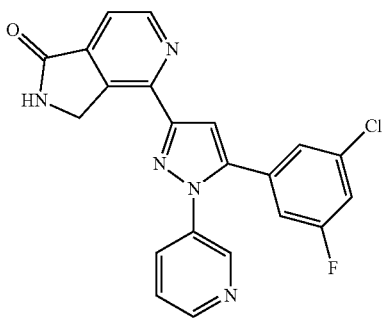 [SMILES: O=C1NCc2c1ccnc2-c1cc(-c2cc(F)cc(Cl)c2)n(-c2cccnc2)n1]

The synthesis of the title compound is performed starting from 1.50 g (4.72 mmol) of the compound from example 14A in a manner analogous to the synthesis of the compound in example 1 with the following modifications.

In step 1 after stirring the raw product with ether and subsequent evaporation under vacuum until dryness, one obtains 1.55 g (75% of theoretical yield) of trimethylsilyl ethyl carbamate.

In step 2 the raw product after workup is purified using column chromatography over silica gel (solvent: dichlormethane/methanol 95:5) and this produces 1.10 g (102% of theoretical yield) of aminopyrazole.

In step 3 the compound from step 2 is reacted for 20 hours at room temperature and for another 3 hours at 50° C. The precipitate is filtered off from the reaction solution and the filtrate is mixed with water. The phases are separated, the aqueous phase is extracted twice with dichloromethane, the combined organic phases are concentrated under vacuum until dryness and the raw product is then purified using preparative HPLC (solvent: acetonitrile/water gradient). The result is 0.59 g (45% of theoretical yield) of bromopyrazole.

In step 4 72 mg (61% of theoretical yield) of the title compound is produced from 100 mg (0.28 mmol) of the compound from step 3.

$^1$H-NMR (400 MHz, DMSO-$d_6$): δ=4.81 (s, 2H), 7.28 (dt, 1H), 7.33 (s, 1H), 7.51-7.60 (m, 3H), 7.70 (d, 1H), 7.86-7.93 (m, 1H), 8.66 (dd, 1H), 8.71 (d, 1H), 8.83 (d, 1H), 9.08 (s, 1H).

LC-MS (Method 3): $R_t$=0.95 min; MS (ESIpos): m/z=406 [M+H]$^+$.

Example 3

4-[1-(3-chloro-4-fluorophenyl)-5-(3-chloro-5-fluorophenyl)-1H-pyrazole-3-yl]-2,3-dihydro-1H-isoindole-1-one

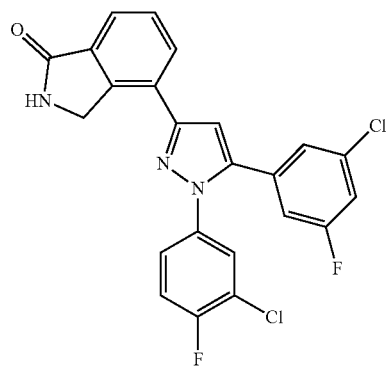 [SMILES: O=C1NCc2c1cccc2-c1cc(-c2cc(F)cc(Cl)c2)n(-c2ccc(F)c(Cl)c2)n1]

The synthesis of the title compound is performed starting from 100 mg (0.25 mmol) of the product from step 3 of example 1 in a manner analogous to the synthesis of the compound from example 1. In step 4, instead of the compound from example 22A, 4-bromo-2,3-dihydroisoindol-1-on (63 mg, 0.30 mmol) is used. The result is 74 mg (65% of theoretical yield) of the title compound.

$^1$H-NMR (400 MHz, DMSO-$d_6$): δ=4.72 (s, 2H), 7.21 (dt, 1H), 7.32-7.41 (m, 2H), 7.49 (s, 1H), 7.51-7.58 (m, 2H), 7.62 (t, 1H), 7.71 (d, 1H), 7.83 (dd, 1H).

LC-MS (Method 1): $R_t$=1.28 min; MS (ESIpos): m/z=456 [M+H]$^+$.

Example 4

4-[5-(3-chloro-5-fluorophenyl)-1-(pyridine-3-yl)-1H-pyrazole-3-yl]-2,3-dihydro-1H-isoindole-1-one

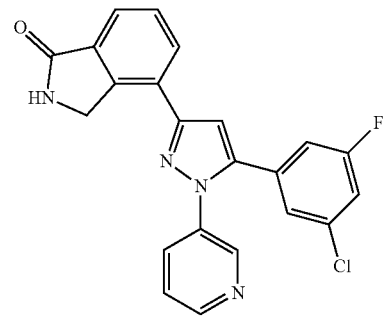 [SMILES: O=C1NCc2c1cccc2-c1cc(-c2cc(F)cc(Cl)c2)n(-c2cccnc2)n1]

The synthesis of the title compound is performed starting from 36 mg (0.10 mmol) of the product from step 3 from example 2 in a manner analogous to the synthesis of the compound from example 2. In step 4, after a 1 hour reaction at 120° C. in the microwave, another 13 mg (0.05 mmol) bis-pinakolato-diboron is added to the reaction solution as well as 5 mg (0.01 mmol) [1,1-bis-(diphenylphosphino)ferrocene]-dichloropalladium-dichloromethane complex, and the mixture is again stirred for 1 hour at 120° C. in the microwave. In addition, 4-bromo-2,3-dihydroisoindole-1-on (26 mg, 0.12 mmol) is used instead of the compound from example 22A. This produces 8 mg (19% of theoretical yield) of the title compound.

$^1$H-NMR (400 MHz, DMSO-d$_6$): δ=4.73 (s, 2H), 7.22 (dt, 1H), 7.34 (s, 1H), 7.50-7.59 (m, 3H), 7.63 (t, 1H), 7.72 (d, 1H), 7.85-7.91 (m, 1H), 8.15 (d, 1H), 8.64 (dd, 1H), 8.68 (d, 1H), 8.74 (s, 1H).

LC-MS (Method 3): R$_t$=1.02 min; MS (ESIpos): m/z=405 [M+H]$^+$.

Example 5

4-{1-(3-chloro-4-fluorophenyl)-5-[3-fluoro-5-(trifluoromethoxy)phenyl]-1H-pyrazole-3-yl}-2,3-dihydro-1H-pyrrolo[3,4-c]pyridine-1-one

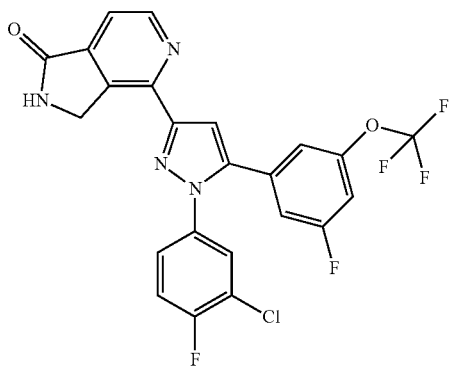 [SMILES: O=C1NCc2c1ccnc2-c1cc(-c2cc(Cl)cc(OC(F)(F)F)c2)n(-c2ccc(F)c(Cl)c2)n1]

The synthesis of the title compound is prepared from 0.50 g (1.19 mmol) of the compound from example 8A in a manner analogous to the synthesis of the compound from example 1 with the following modifications.

In step 1, after purification of the raw product using preparative HPLC (Solvent: acetonitrile/water gradient), 0.51 g (80% of theoretical yield) of trimethylsilyl ethyl carbamate is obtained.

In step 2, after stirring the raw product with ether/pentane, 0.32 g (86% of theoretical yield) aminopyrazole is isolated.

In step 3, 264 mg (0.68 mmol) of the product from step 2 is stirred for 2 hours at room temperature with 116 mg (0.81 mmol) copper(I)bromide, 0.14 mL (1.02 mmol) n-pentyl nitrite and 1 mg (0.004 mmol) copper(II)bromide in 18 ml acetonitrile. After adding another 49 mg (0.34 mmol) copper (I)bromide and 0.05 ml (0.34 mmol) N-pentyl nitrite, the reaction mixture is stirred overnight at RT. The reaction mixture is mixed with water, the phases are separated and the aqueous phase is extracted three times using ethylacetate. The combined organic phases are dried using sodium sulfate, filtered and evaporated under vacuum to dryness. The raw product was absorbed in a small amount of acetonitrile, filtered through a Millipore filter and then purified using preparative HPLC (solvent: acetonitrile/water gradient). This produces 130 g (42% of theoretical yield) of bromopyrazole.

In step 4, 42 mg (0.09 mmol) of the compound from step 3 is produced after separation of the raw product using preparative HPLC (solvent: acetonitrile/water gradient) and then recrystallization from acetonitrile 4 mg (9% of theoretical yield) from the title compound.

$^1$H-NMR (400 MHz, DMSO-d$_6$): δ=4.80 (s, 2H), 7.07 (s, 1H), 7.41-7.47 (m, 1H), 7.48-7.60 (m, 4H), 7.70 (d, 1H), 7.83 (dd, 1H), 8.83 (d, 1H), 9.06 (s, 1H).

LC-MS (Method 1): R$_t$=1.26 min; MS (ESIpos): m/z=507 [M+H]$^+$.

Example 6

4-{5-[3-fluoro-5-(trifluoromethoxy)phenyl]-1-(pyridine-3-yl)-1H-pyrazole-3-yl}-2,3-dihydro-1H-pyrrolo[3,4-c]pyridine-1-one

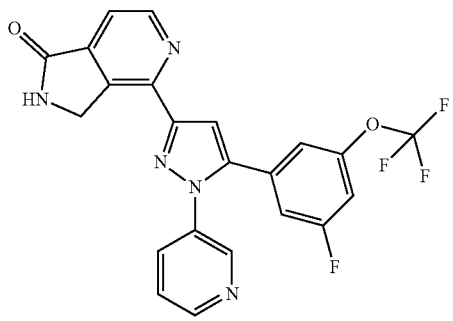 [SMILES: O=C1NCc2c1ccnc2-c1cc(-c2cc(Cl)cc(OC(F)(F)F)c2)n(-c2cccnc2)n1]

Step 1

A solution of 1.47 g (4.00 mmol) of the pyrazole carboxylic acid from example 15A in 38 ml dioxane is mixed with 1.72 ml (8.00 mmol) diphenyl phosphorazidate and 840 μl (6.00 mmol) of triethylamine, and the reaction mixture is stirred for 1 h at 50° C. After adding 2.87 ml (20.00 mmol) 2-(trimethylsilyl)ethanol, the reaction mixture is stirred for 2 h under reflux, mixed with water and extracted twice using ethyl acetate. The combined organic phases are dried using sodium sulfate, filtered and evaporated under vacuum to dryness. The residue is crystallized using ether/pentane, the sediment is filtered off and dried. This produced 1.55 g (80% of theoretical yield) of trimethylsilyl ethyl carbamate.

Step 2

1.55 g (3.21 mmol) of the product from step 1 is dissolved in 38 ml tetrahydrofuran and mixed with tetra-n-butylammonium fluoride (1N in THF, 6.43 ml, 6.43 mmol). The reaction mixture is stirred for 3 h at 50° C., the solvent is extracted under vacuum and the residue is absorbed in ethyl acetate and washed with water. The organic phase is dried using sodium sulfate, filtered and evaporated under vacuum until dryness. The residue is crystallized using ether/pentane, the solid is filtered off and dried. This produces 1.03 g (95% of theoretical yield) of aminopyrazole.

Using an analogous approach, (1.20 g, 2.49 mmol) of the product from Step 1 is converted to 0.78 g (93% of theoretical yield) of trimethylsilyl ethyl carbamate.

Step 3

A solution of 0.66 g (4.57 mmol) copper(I)bromide, 760 pl (5.72 mmol) n-pentyl nitrite and 5 mg (0.02 mmol) copper (II)bromide in 67 ml acetonitrile is combined with a solution of 1.29 g (3.81 mmol) of the compound from step 2 in 33 ml acetonitrile. The reaction mixture is stirred overnight at RT, combined with water, the phases are separated and the aqueous phase is extracted three times using ethyl acetate. The combined organic phases are dried using sodium sulfate, filtered and evaporated under vacuum to dryness. The residue is dissolved in some acetonitrile, filtered over Millipore filters and separated using preparative HPLC (solvent: acetonitrile/water gradient). This produces 0.45 g (29% of theoretical yield) of bromopyrazole.

Step 4

In three parallel mixtures, each of three 100 mg (0.25 mmol) portions of the product from step 3 is dissolved in 5 ml dioxane in each case and each is combined with 76 mg (0.30 mmol) of bis-pinakolato-diboron, 73 mg (0.75 mmol) potassium acetate and 12 mg (0.017 mmol) [1,1-bis-(diphenylphosphino)ferrocene]-dichloropalladium dichloromethane complex. The reaction mixtures are stirred for 1 h in the microwave at 120° C. and cooled to RT, then combined with 50 mg (0.30 mmol) of the compound from example 22A, 250 µl (2 N in water, 0.50 mmol) sodium carbonate solution and 10 mg (0.013 mmol) [1,1-bis-(diphenylphosphino)ferrocene]-dichloropalladium dichloromethane complex and stirred for 2 h at 120° C. The reaction mixtures are combined. The suspension is diluted in a small amount of acetonitrile, filtered through a Millipore filter and separated by preparative HPLC (solvent: acetonitrile/water gradient). Once the resulting solid has crystallized out of the acetonitrile, this produces 174 mg (51% of theoretical yield) of the title compound.

$^1$H-NMR (400 MHz, DMSO-d$_6$): δ=4.81 (s, 2H), 7.11 (s, 1H), 7.46-7.59 (m, 4H), 7.70 (d, 1H), 7.87-7.93 (m, 1H), 8.66 (dd, 1H), 8.70 (d, 1H), 8.83 (d, 1H), 9.07 (s, 1H).

LC-MS (Method 1): R$_t$=1.02 min; MS (ESIpos): m/z=456 [M+H]$^+$.

Example 7

4-{5-[3-fluoro-5-(trifluoromethoxy)phenyl]-1-(pyridine-3-yl)-1H-pyrazole-3-yl}-2,3-dihydro-1H-isoindole-1-one The synthesis of the title compound is performed starting from 100 mg (0.25 mmol) of the product from step 3 of the compound from example 6 in a manner analogous to step 4 from example 6, whereby instead of the compound from example 22A, 4-bromo-2,3-dihydroisoindole-1-on (63 mg, 0.30 mmol) is used. This produces 64 mg (56% of theoretical yield) of the title compound.

$^1$H-NMR (400 MHz, DMSO-d$_6$): δ=4.73 (s, 2H), 7.12 (s, 1H), 7.43 (dt, 1H), 7.48-7.58 (m, 3H), 7.64 (t, 1H), 7.72 (d, 1H), 7.85-7.91 (m, 1H), 8.16 (d, 1H), 8.64 (d, 1H), 8.67 (d, 1H), 8.75 (s, 1H).

LC-MS (Method 3): R$_t$=1.07 min; MS (ESIpos): m/z=455 [M+H]$^+$.

Example 8

4-{5-[3-fluoro-5-(trifluoromethoxy)phenyl]-1-(pyridine-3-yl)-1H-pyrazole-3-yl}-1H-isoindole-1,3(2H)-dione 40 mg (0.09 mmol) of the compound from example 7 are absorbed in 1 ml acetone and mixed with 1 ml water, 74 mg (0.29 mmol) magnesium nitrate hexahydrate and 32 mg (0.20 mmol) potassium permanganate. The reaction mixture is stirred for 24 hours at room temperature, diluted with 5 ml acetonitrile and filtered through a Millipore filter. The filtrate is extracted twice with dichloromethane and the combined organic phases washed with a saturated sodium chloride solution, dried using sodium sulfate, filtered and evaporated under vacuum until dryness. The residue is recrystallized from acetonitrile. This produces 14 mg (25% of theoretical yield, 75% purity) of the title compound.

$^1$H-NMR (400 MHz, DMSO-d$_6$): δ=7.09 (s, 1H), 7.39 (dt, 1H), 7.48-7.58 (m, 2H), 7.69 (s, 1H), 7.86-7.93 (m, 3H), 8.33 (dd, 1H), 8.63-8.68 (m, 2H), 11.49 (s, 1H).

LC-MS (Method 1): R$_t$=1.12 min; MS (ESIpos): m/z=469 [M+H]$^+$.

Example 9

4-{1-(3-chloro-4-fluorophenyl)-5-[3-chloro-5-(trifluoromethoxy)phenyl]-1H-pyrazole-3-yl}-2,3-dihydro-1H-pyrrolo[3,4-c]pyridine-1-one The synthesis is prepared from 825 mg (1.90 mmol) of the compound from example 9A in a manner analogous to the synthesis of the compound from example 6. This produces 844 mg (81% of theoretical yield) of trimethylsilyl ethyl carbamate (step 1), 541 mg (87% of theoretical yield) of aminopyrazole (step 2) and 223 mg (37% of theoretical yield) of bromopyrazole (step 3). In step 4, 30 mg (27% of theoretical yield) of the title compound are obtained from 100 mg (0.21 mmol) of the compound from step 3.

$^1$H-NMR (400 MHz, DMSO-$d_6$): δ=4.80 (s, 2H), 7.18 (s, 1H), 7.42-7.48 (m, 1H), 7.53-7.60 (m, 2H), 7.65-7.72 (m, 3H), 7.84 (dd, 1H), 8.83 (d, 1H), 9.06 (s, 1H).

LC-MS (Method 1): $R_t$=1.28 min; MS (ESIpos): m/z=523 [M+H]$^+$.

Example 10

4-{5-[3-chloro-5-(trifluoromethoxy)phenyl]-1-(pyridine-3-yl)-1H-pyrazole-3-yl}-2,3-dihydro-1H-pyrrolo[3,4-c]pyridine-1-one

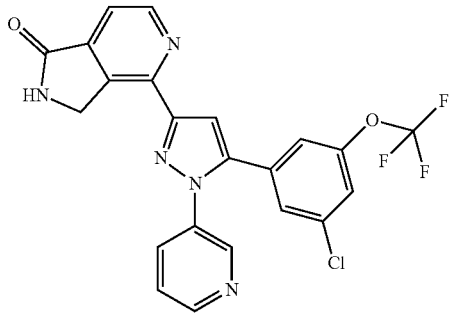

Step 1

A solution of 2.50 g (6.52 mmol) of the pyrazole carboxylic acid from example 16A in 46 ml dioxane is combined with 2.81 ml (13.03 mmol) diphenyl phosphorazidate and 1.36 ml (9.77 mmol) triethylamine, and the reaction mixture is stirred for 1 h at 50° C. After adding 4.67 ml (32.58 mmol) 2-(trimethylsilyl)ethanol, the reaction mixture is stirred for 2 h under reflux, combined with water and extracted twice using ethyl acetate. The combined organic phases are dried using sodium sulfate, filtered and evaporated under vacuum to dryness. The residue is crystallized with ether/pentane and the sediment is filtered out and dried. This produces 2.50 g (77% of theoretical yield) of trimethylsilyl ethyl carbamate.

Step 2

2.55 g (5.11 mmol) of the product from step 1 is dissolved in 60 ml tetrahydrofuran and combined with tetra-n-butylammonium fluoride (1N in THF, 10.22 ml, 10.22 mmol). The reaction mixture is stirred for 3 h at 50° C., the solvent is extracted under vacuum, and the residue is absorbed in ethyl acetate and washed with water. The organic phase is dried using sodium sulfate, filtered and evaporated under vacuum until dryness. The residue is crystallized using ether/pentane, the solid is filtered off and dried. This produces 1.60 g (88% of theoretical yield) of aminopyrazole.

Step 3

A solution of 775 mg (5.40 mmol) copper(I)bromide, 900 μl (6.75 mmol) n-pentyl nitrite and 7.8 mg (0.04 mmol) copper(II)bromide in 80 ml acetonitrile is combined, by dropwise addition, with a solution of 1.60 g (4.50 mmol) of the compound from step 2 in 40 ml acetonitrile. The reaction mixture is stirred at RT overnight, combined with water and extracted three times using ethyl acetate. The combined organic phases are dried using sodium sulfate, filtered and evaporated under vacuum to dryness. The residue is dissolved in a small amount of acetonitrile, filtered through a Millipore filter and separated by preparative HPLC (solvent: acetonitrile/water gradient). This produces 701 mg (37% of theoretical yield) of bromopyrazole.

Step 4

In four parallel procedures, four portions of 175 mg (0.42 mmol) of the product from step 3 are each dissolved in 5 ml dioxane and combined with 128 mg (0.50 mmol) of bispinakolato-diboron, 123 mg (1.26 mmol) potassium acetate and 21 mg (0.025 mmol) [1,1-bis-(diphenyl-phosphino)ferrocene]-dichloropalladium-dichloro-methane complex. Each reaction mixture is stirred in the microwave for 1 h at 120° C., cooled to RT, combined with 85 mg (0.50 mmol) of the compound from example 22A, 0.42 ml (2 N in water, 0.84 mmol) of a sodium carbonate solution and 17 mg (0.02 mmol) [1,1-bis-(diphenylphosphino)ferrocene]-dichloropalladium-dichloromethane complex and stirred for 2 h at 120° C. The reaction mixtures are combined. The suspension is diluted with acetonitrile, filtered through a Millipore filter and separated by preparative HPLC (solvent: acetonitrile/water gradient). Once the resulting solid has crystallized out of the acetonitrile, this produces 286 mg (36% of theoretical yield) of the title compound.

$^1$H-NMR (400 MHz, DMSO-$d_6$): δ=4.80 (s, 2H), 7.24 (s, 1H), 7.53-7.60 (m, 2H), 7.65-7.68 (m, 2H), 7.70 (d, 1H), 7.87-7.93 (m, 1H), 8.66 (dd, 1H), 8.71 (d, 1H), 8.83 (d, 1H), 9.08 (s, 1H).

LC-MS (Method 1): $R_t$=1.03 min; MS (ESIpos): m/z=472 [M+H]$^+$.

Example 11

4-{5-[3-chloro-5-(trifluoromethoxy)phenyl]-1-(pyridine-3-yl)-1H-pyrazole-3-yl}-2,3-dihydro-1H-isoindole-1-one

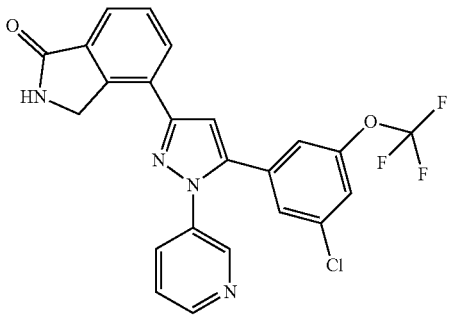 [SMILES: O=C1NCc2c1cccc2-c1cc(-c2cc(Cl)cc(OC(F)(F)F)c2)n(-c2cccnc2)n1]

The synthesis of the title compound is performed starting from 100 mg (0.24 mmol) of the product from step 3 of the compound from example 10 in a manner analogous to step 4 of the synthesis of the compound from example 10. Instead of the compound from example 22A, 4-bromo-2,3-dihydroisoindole-1-on (61 mg, 0.29 mmol) is used. This produces 28 mg (24% of theoretical yield, 94% purity) of the title compound.

$^1$H-NMR (400 MHz, DMSO-$d_6$): δ=4.73 (s, 2H), 7.21 (s, 1H), 7.51-7.60 (m, 2H), 7.61-7.69 (m, 3H), 7.72 (d, 1H), 7.89 (d, 1H), 8.17 (d, 1H), 8.61-8.71 (m, 2H), 8.75 (s, 1H).

LC-MS (Method 3): $R_t$=1.13 min; MS (ESIpos): m/z=471 [M+H]$^+$.

Example 12

4-{5-[3-bromo-5-(trifluoromethoxy)phenyl]-1-(3-chloro-4-fluorophenyl)-1H-pyrazole-3-yl}-2,3-dihydro-1H-pyrrolo[3,4-c]pyridine-1-one

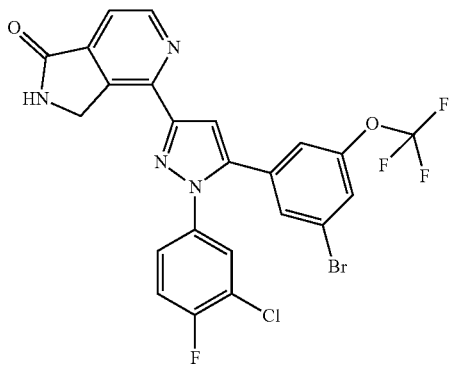

The synthesis of the title compound is performed starting from 2.17 g (4.52 mmol) of the compound from example 10A in a manner analogous to synthesis of the compound from example 6 with the following modifications.

In step 1, after purification of the raw product using column chromatography over silica gel (solvent: cyclohexane/ethyl acetate 10:1) 2.48 g (92% of theoretical yield) of trimethylsilyl ethyl carbamate is produced.

In step 2, the reaction mixture is stirred for 3 hours at 50° C. and 16 hours at RT. After processing analogously to step 2 from example 6, the raw product is purified using column chromatography over silica gel (solvent: dichloro-methane/methanol 98:2→95:5), and this produces 1.87 g (100% of theoretical yield) of aminopyrazole.

In step 3, 100 mg (0.22 mmol) of the compound from step 2 and 234 mg (2.00 mmol) isopentyl nitrite is added in portions to 1 ml diiodomethane at 100° C. The reaction mixture is stirred for 2 hours at 100° C., then mixed with a small amount of acetonitrile, filtered through a Millipore filter and separated by preparative HPLC (solvent: acetonitrile/water gradient). This produces 55 mg (44% of theoretical yield) of iodopyrazole.

Divided into two batches, in step 4 a total of 45 mg (0.09 mmol) of the compound from step 3 is dissolved in 1.9 ml dioxane and mixed with 24 mg (0.09 mmol) bis-pinakolato-diboron, 24 mg (0.25 mmol) potassium acetate and 3.9 mg (0.005 mmol) [1,1-bis-(diphenyl-phosphino)ferrocene]-dichloropalladium-dichlormethane-complex. The reaction mixtures are in each case stirred in the microwave for 1 hour at 120° C., cooled to room temperature and mixed with a total of 23 mg (0.13 mmol) of the compound from example 22A, 0.09 ml (2 N in water, 0.18 mmol) sodium carbonate solution and 3.6 mg (0.004 mmol) [1,1-bis-(diphenylphosphino)ferrocene]-dichloropalladium-dichlormethane complex. The reaction mixture is stirred at 120° C. for 4 hours and the reaction mixtures are then combined. The suspension is diluted with acetonitrile, filtered through a Millipore filter and separated using preparative HPLC (solvent: acetonitrile/water gradient). Once the resulting solid has crystallized out of the acetonitrile, this produces 286 mg (36% of theoretical yield) of the title compound. After additional purification by column chromatography of the product over silica gel (solvent: cyclohexane/ethyl acetate 1:3→0:100) and followed by stirring with acetonitrile, this produces 2.6 mg of the title compound (5% of the theoretical yield, 94% purity).

$^1$H-NMR (400 MHz, DMSO-d$_6$): δ=4.80 (s, 2H), 7.22 (s, 1H), 7.42-7.47 (m, 1H), 7.54-7.60 (m, 2H), 7.70 (d, 1H), 7.77 (s, 1H), 7.81-7.86 (m, 2H), 8.83 (d, 1H), 9.06 (s, 1H).

LC-MS (Method 1): $R_t$=1.30 min; MS (ESIpos): m/z=567 [M+H]$^+$.

Example 13

4-{5-[3-bromo-5-(trifluoromethoxy)phenyl]-1-(pyridine-3-yl)-1H-pyrazole-3-yl}-2,3-dihydro-1H-pyrrolo[3,4-c]pyridine-1-one

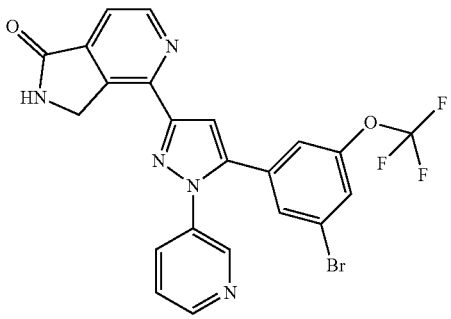

Step 1

A solution of 2.75 g (6.42 mmol) of the pyrazole carboxylic acid from example 17A in 50 ml dioxane is combined with 2.77 ml (12.85 mmol) diphenyl phosphorazidate and 1.34 ml (9.63 mmol) triethylamine, and the reaction mixture is stirred for 1 h at 50° C. After adding 4.60 ml (32.11 mmol) 2-(trimethylsilyl)ethanol, the reaction mixture is stirred for 2 h under reflux, mixed with water and extracted twice using ethylacetate. The combined organic phases are dried using sodium sulfate, filtered and evaporated under vacuum to dryness. The residue is stirred with ether, and the solid is filtered off and dried. This produces 1.98 g (57% of theoretical yield) of trimethylsilyl ethyl carbamate. The mother liquor is separated using preparative HPLC (solvent: acetonitrile/water gradient), yielding a further 0.61 g (13% of theoretical yield) of the bromopyrazole.

Step 2

The product from step 1 (2.58 g, 4.75 mmol) is dissolved in 40 ml tetrahydrofuran, and tetra-n-butylammonium fluoride (1N in THF, 9.5 ml, 9.50 mmol) is added. The reaction mixture is stirred for 3 hours at 50° C., the solvent extracted under vacuum, and the residue absorbed in dichloromethane and washed with water. The organic phase is dried using sodium sulfate, filtered and evaporated under vacuum until dryness. The residue is separated using column chromatography over silica gel (solvent: dichloro-methane/methanol 95:5), yielding 1.91 g (97% of theoretical yield) of the aminopyrazole.

Step 3

500 mg (1.25 mmol) of the compound from step 2 and 1.32 g (11.27 mmol) isopentyl nitrite are successively added to 5 ml diiodomethane over the course of 10 min at 100° C. The reaction mixture is stirred for 1 hour at 100° C.; then a small amount of acetonitrile is added and the mixture is separated using preparative HPLC (solvent: acetonitrile/water gradient). The yield is 482 mg (75% of theoretical yield) of the iodopyrazole.

Step 4

100 mg (0.20 mmol) of the product from step 3 is dissolved in 5 ml of dioxane and 60 mg of (0.24 mmol) bis-pinakolato-diboron, 58 mg (0.59 mmol) of potassium acetate and 7 mg (0.01 mmol) [1,1-bis-(diphenylphosphino)ferrocen]-dichloropalladium-dichloromethane complex added. The reaction mixture is stirred 1 hour in the microwave at 120° C., cooled to RT, added to 50 mg (0.29 mmol) of the compound from example 22A, 0.20 ml (2 N in water, 0.39 mmol) of sodium carbonate solution and 8 mg (0.01 mmol) of [1,1-bis-(diphenylphosphino)ferrocene]-dichloropalladium-dichloromethane complex, and stirred for 2 hours at 120° C. The suspension is directly separated using preparative HPLC (solvent: acetonitrile/water gradient). 10 mg (9% of theoretical yield) of the title compound is obtained.

$^1$H-NMR (400 MHz, DMSO-d$_6$): δ=4.81 (s, 2H), 7.28 (s, 1H), 7.52-7.61 (m, 2H), 7.70 (d, 1H), 7.75-7.81 (m, 2H), 7.90 (d, 1H), 8.66 (d, 1H), 8.71 (d, 1H), 8.84 (d, 1H), 9.08 (s, 1H).

LC-MS (Method 3): R$_t$=1.10 min; MS (ESIpos): m/z=516 [M+H]$^+$.

Example 14

4-{5-[3-(difluoromethoxy)-5-fluorophenyl]-1-(pyridine-3-yl)-1H-pyrazole-3-yl}-2,3-dihydro-1H-pyrrolo[3,4-c]pyridine-1-one

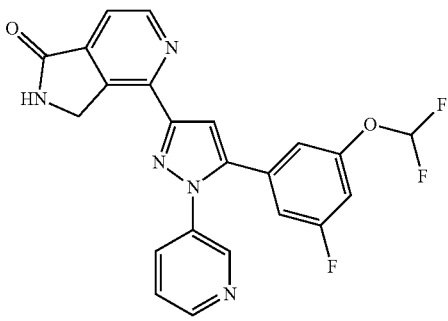

The synthesis of the title compound is performed starting from 402 mg (1.15 mmol) of the compound from example 18A in a manner analogous to the synthesis of the compound from example 6, with the following modifications.

In step 1, 402 mg (73% of theoretical yield) of the trimethylsilyl ethyl carbamate is obtained.

In step 2, the raw product is purified after processing analogously to example 6 using preparative HPLC (solvent: acetonitrile/water gradient), yielding 241 mg (88% of theoretical yield) of aminopyrazole.

In step 3, the product from step 2 is reacted to 119 mg (44% of theoretical yield, 0.31 mmol) of bromopyrazole.

Starting from 106 mg (0.28 mmol) of the compound from step 3, step 4 yields 35 mg (29% of theoretical yield of the title compound after final recrystallization from acetonitrile.

$^1$H-NMR (400 MHz, DMSO-d$_6$): δ=4.81 (s, 2H), 7.05 (s, 1H), 7.16 (d, 1H), 7.24 (d, 1H), 7.30 (t, 1H), 7.51-7.60 (m, 2H), 7.70 (d, 1H), 7.90 (d, 1H), 8.66 (d, 1H), 8.71 (d, 1H), 8.83 (d, 1H), 9.09 (s, 1H).

LC-MS (Method 2): R$_t$=2.11 min; MS (ESIpos): m/z=438 [M+H]$^+$.

Example 15

4-{1-(3-chloro-4-fluorophenyl)-5-[3-(difluoromethoxy)-5-fluorophenyl]-1H-pyrazole-3-yl}-2,3-dihydro-1H-pyrrolo[3,4-c]pyridine-1-one

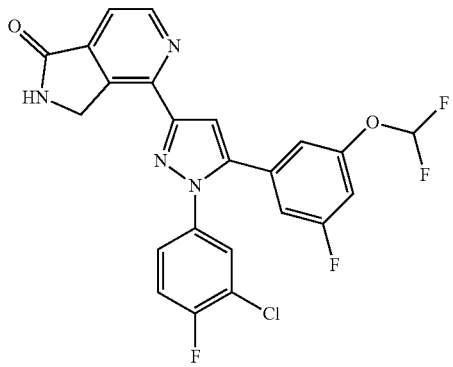 [SMILES: O=C1NCc2c1ccnc2-c1cc(-c2cc(F)cc(OC(F)F)c2)n(-c2ccc(F)c(Cl)c2)n1]

The synthesis of the title compound starts from 332 mg (0.83 mmol) of the compound from example 11A in a manner analogous to the synthesis of the compound from example 6, with the following modifications.

In step 1, 333 mg (78% of theoretical yield) of trimethylsilyl ethyl carbamate is obtained.

In step 2, the raw product is purified after processing using preparative HPLC (solvent: acetonitrile/water gradient) in a manner analogous to example 6, yielding 207 mg (87% of theoretical yield) of aminopyrazole.

In step 3, 191 mg (0.51 mmol) of the product from step 2 is reacted to 96 mg (43% of theoretical yield) of bromopyrazole.

Starting from 85 mg (0.20 mmol) of the compound from step 3, 17 mg (18% of theoretical yield) of the title compound is obtained in step 4 after final recrystallization from acetonitrile.

$^1$H-NMR (400 MHz, DMSO-d$_6$): δ=4.80 (s, 2H), 7.02 (s, 1H), 7.18 (d, 1H), 7.24 (d, 1H), 7.30 (t, 1H), 7.37-7.44 (m, 1H), 7.46-7.58 (m, 2H), 7.70 (d, 1H), 7.86 (dd, 1H), 8.82 (d, 1H), 9.06 (s, 1H).

LC-MS (Method 2): R$_t$=2.52 min; MS (ESIpos): m/z=489 [M+H]$^+$.

Example 16

4-{5-[3-chloro-5-(difluoromethoxy)phenyl]-1-(pyridine-3-yl)-1H-pyrazole-3-yl}-2,3-dihydro-1H-pyrrolo[3,4-c]pyridine-1-one

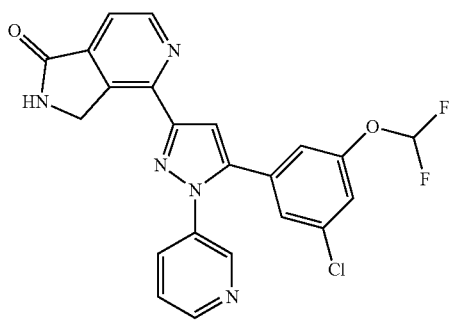 [SMILES: O=C1NCc2c1ccnc2-c1cc(-c2cc(Cl)cc(OC(F)F)c2)n(-c2cccnc2)n1]

The synthesis of the title compound is performed starting from 2.70 g (7.38 mmol) of the compound from example 19A in a manner analogous to the synthesis of the compound from example 6, with the following modifications.

In step 1, 2.56 g (72% of theoretical yield) of trimethylsilyl ethyl carbamate is obtained, and in step 2, 1.45 g (81% of theoretical yield) of aminopyrazole. In step 3, 0.80 g (2.38 mmol) of the product from step 2 is converted to 0.29 g (31% of theoretical yield) of bromopyrazole. In step 4, starting from 100 mg (0.25 mmol) of the compound from step 3, 35 mg (31% of theoretical yield) of the title compound is obtained after final recrystallization from acetonitrile.

$^1$H-NMR (400 MHz, DMSO-d$_6$): δ=4.81 (s, 2H), 7.16 (s, 1H), 7.30 (s, 1H), 7.35 (t, 1H), 7.41 (t, 1H), 7.52-7.59 (m, 2H), 7.70 (d, 1H), 7.86-7.93 (m, 1H), 8.66 (dd, 1H), 8.71 (d, 1H), 8.83 (d, 1H), 9.08 (s, 1H).

LC-MS (Method 3): R$_t$=0.98 min; MS (ESIpos): m/z=454 [M+H]$^+$.

Example 17

4-{5-[3-chloro-5-(difluoromethoxy)phenyl]-1-(2-chloropyridine-4-yl)-1H-pyrazole-3-yl}-2,3-dihydro-1H-pyrrolo[3,4-c]pyridine-1-one

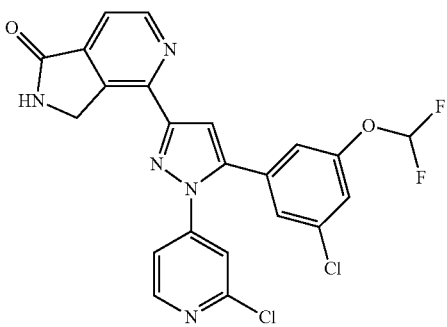 [SMILES: O=C1NCc2c1ccnc2-c1cc(-c2cc(Cl)cc(OC(F)F)c2)n(-c2ccnc(Cl)c2)n1]

The synthesis of the title compound is performed starting from 629 mg (1.57 mmol) of the compound from example 12A in a manner analogous to the synthesis of the compound from example 6, with the following modifications.

In step 1, 643 mg (79% of theoretical yield) of trimethylsilyl ethyl carbamate is obtained, and in step 2, 432 mg (94% of theoretical yield) of aminopyrazole. In Step 3, 410 mg (1.11 mmol) of the compound from step 2 and 1164 mg (9.94 mmol) of isopentyl nitrite are successively added to 4.5 ml of diiodomethane over the course of 30 minutes at 100° C. The reaction mixture is stirred for 2 hours at 100° C., a small quantity of acetonitrile is added, and the mixture is then filtered through a Millipore filter and subsequently separated twice by means of preparative HPLC (solvent: acetonitrile/water gradient). The yield is 303 mg (57% of theoretical yield) of iodopyrazole. In step 4, starting from 100 mg (0.21 mmol) of the iodopyrazole from step 3, 2.7 mg (3% of theoretical yield) of the title compound is obtained after double separation using preparative HPLC (solvent: acetonitrile/water gradient) and final recrystallization from acetonitrile.

$^1$H-NMR (400 MHz, DMSO-d$_6$): δ=4.88 (s, 2H), 7.27 (s, 1H), 7.34 (t, 1H), 7.37 (dd, 1H), 7.48-7.51 (m, 2H), 7.55 (s, 1H), 7.68 (d, 1H), 7.73 (d, 1H), 8.47 (d, 1H), 8.84 (d, 1H), 9.13 (s, 1H).

LC-MS (Method 1): R$_t$=1.06 min; MS (ESIpos): m/z=488 [M+H]$^+$.

Example 18

4-{5-[3-chloro-5-(difluoromethoxy)phenyl]-1-(pyridine-3-yl)-1H-pyrazole-3-yl}-2,3-dihydro-1H-isoindole-1-one

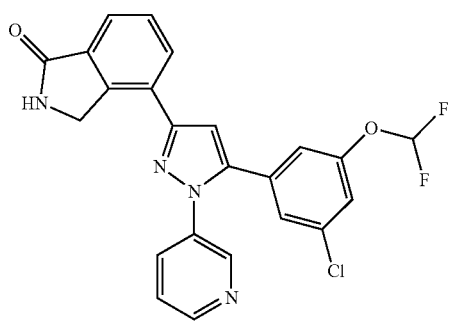 [SMILES: O=C1NCc2c1cccc2-c1cc(-c2cc(Cl)cc(OC(F)F)c2)n(-c2cccnc2)n1]

The synthesis of the title compound is performed in a manner analogous to the synthesis of the compound from example 16, starting from 358 mg (0.89 mmol) of the product from step 3 of the compound from example 16. In step 4, 4-bromo-2,3-dihydroisoindole-1-one (181 mg, 1.07 mmol) is used in place of the compound from example 22A. After final stirring with diethyl ether, 206 mg (51% of theoretical yield) of the title compound is obtained.

$^1$H-NMR (400 MHz, DMSO-d$_6$): δ=4.73 (s, 2H), 7.11 (s, 1H), 7.27 (t, 1H), 7.37 (s, 1H), 7.42 (s, 1H), 7.50-7.58 (m, 2H), 7.63 (t, 1H), 7.72 (d, 1H), 7.88 (d, 1H), 8.16 (d, 1H), 8.64 (d, 1H), 8.68 (d, 1H), 8.74 (s, 1H).

LC-MS (Method 3): R$_t$=1.04 min; MS (ESIpos): m/z=453 [M+H]$^+$.

Example 19

4-{5-[3-bromo-5-(difluoromethoxy)phenyl]-1-(pyridine-3-yl)-1H-pyrazole-3-yl}-2,3-dihydro-1H-pyrrolo[3,4-c]pyridine-1-one

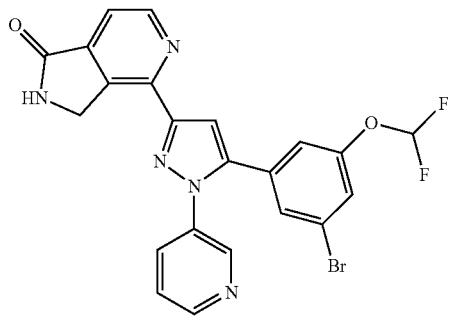 [SMILES: O=C1NCc2c1ccnc2-c1cc(-c2cc(Br)cc(OC(F)F)c2)n(-c2cccnc2)n1]

The synthesis of the title compound is performed starting from 2.00 g (4.88 mmol) of the compound from example 20A in a manner analogous to the synthesis of the compound from example 6, with the following modifications.

In step 1, 1.95 g (76% of theoretical yield) of trimethylsilyl ethyl carbamate is obtained, and in step 2, 1.21 g (86% of theoretical yield) of aminopyrazole. In step 3, 1.00 g (2.62 mmol) of the compound from step 2 and 2.77 g (23.61 mmol) of isopentyl nitrite are successively added to 6 ml of diiodomethane within 30 minutes at 100° C. The reaction mixture is stirred for 2 hours at 100° C., then a small quantity of acetonitrile is added, the mixture is filtered through a Millipore filter, and finally separated by means of preparative HPLC (solvent: acetonitrile/water gradient). One obtains 0.85 g (66% of theoretical yield) of iodopyrazole. In step 4, starting from 100 mg (0.20 mmol) of the iodopyrazole from step 3, 3.1 mg (3% of theoretical yield, 89% purity) of the title compound is obtained after separation using preparative HPLC (solvent: acetonitrile/water gradient) and final recrystallization from acetonitrile.

$^1$H-NMR (400 MHz, DMSO-d$_6$): δ=4.81 (s, 2H), 7.20 (s, 1H), 7.30 (t, 1H), 7.46 (t, 1H), 7.53 (t, 1H), 7.53-7.60 (m, 2H), 7.70 (d, 1H), 7.87-7.93 (m, 1H), 8.66 (dd, 1H), 8.71 (d, 1H), 8.83 (d, 1H), 9.08 (s, 1H).

LC-MS (Method 1): R$_t$=1.00 min; MS (ESIpos): m/z=498 [M+H]$^+$.

Example 20

4-{5-[3-bromo-5-(difluoromethoxy)phenyl]-1-(2-chloropyridine-4-yl)-1H-pyrazole-3-yl}-2,3-dihydro-1H-pyrrolo[3,4-c]pyridine-1-one

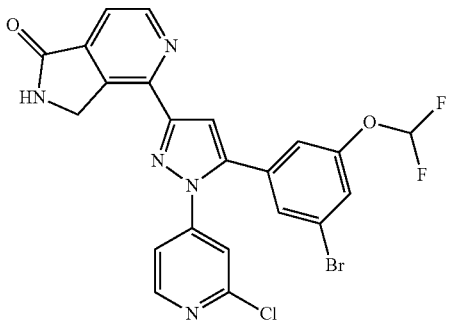

The synthesis of the title compound is performed starting with 1.50 g (3.37 mmol) of the compound from example 13A in a manner analogous to the synthesis of the compound from example 6, with the modifications listed below.

In step 1, one obtains 1.56 g (83% of theoretical yield) of the trimethylsilyl ethyl carbamate and in step 2, 1.11 g (92% of theoretical yield) of the aminopyrazole. In step 3, 0.80 g (1.93 mmol) of the compound from step 2 and 2.03 g (17.32 mmol) isopentyl nitrite are successively added to 6 ml of diiodomethane at 100° C. within 30 min. The reaction mixture is stirred for 2 hours at 100° C.; then a small amount of acetonitrile is added, the mixture filtered through a millipore filter, and finally separated by means of preparative HPLC (solvent: acetonitrile/water gradient). 0.40 g (40% of theoretical yield) of the iodopyrazole is obtained. In step 4, starting with 100 mg (0.19 mmol) of the iodopyrazole from step 3 after separation using preparative HPLC (solvent: acetonitrile/water gradient) and subsequent recrystallization from acetonitrile, 2.1 mg (2% of theoretical yield) of the title compound is obtained.

$^1$H-NMR (400 MHz, DMSO-d$_6$): δ=4.88 (s, 2H), 7.31 (t, 1H), 7.33 (t, 1H), 7.37 (dd, 1H), 7.55 (s, 1H), 7.59-7.63 (m, 2H), 7.68 (d, 1H), 7.73 (d, 1H), 8.47 (d, 1H), 8.84 (d, 1H), 9.12 (s, 1H).

LC-MS (Method 1): R$_t$=1.11 min; MS (ESIpos): m/z=532 [M+H]$^+$.

Example 21

4-{5-[3-bromo-5-(difluoromethoxy)phenyl]-1-(pyridine-3-yl)-1H-pyrazole-3-yl}-2,3-dihydro-1H-isoindole-1-one

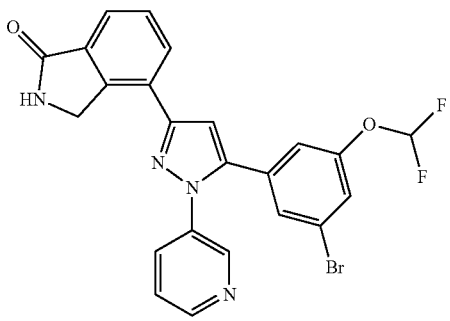 [SMILES: O=C1NCc2c1cccc2-c1cc(-c2cc(Br)cc(OC(F)F)c2)n(-c2cccnc2)n1]

The synthesis of the title compound is performed in a manner analogous to example 19, starting with 100 mg (0.20 mmol) of the product from step 3 of the synthesis of the compound from example 19. In step 4,4-bromo-2,3-dihydroisoindole-1-one (52 mg, 0.24 mmol) is used in place of the compound from example 22A. 2.7 mg (2% of theoretical yield, 79% purity) of the title compound is obtained.

$^1$H-NMR (400 MHz, DMSO-d$_6$): δ=4.73 (s, 2H), 7.14 (s, 1H), 7.27 (t, 1H), 7.47-7.60 (m, 4H), 7.63 (t, 1H), 7.72 (d, 1H), 7.88 (d, 1H), 8.16 (d, 1H), 8.64 (d, 1H), 8.67 (d, 1H), 8.74 (s, 1H).

LC-MS (Method 1): R$_t$=1.06 min; MS (ESIpos): m/z=497 [M+H]$^+$.

The following compounds were synthesised in a manner analogous to the examples described above:

| | Structure | SM Step 1 | SM Step 4 |
|---|---|---|---|
| Example 22 | 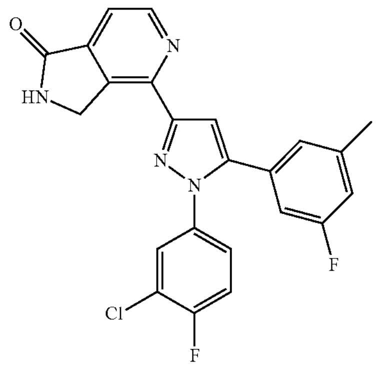 [SMILES: Cc1cc(F)cc(-c2cc(-c3nccc4c3CNC4=O)nn2-c2ccc(F)c(Cl)c2)c1] | | |
| Example 23 | 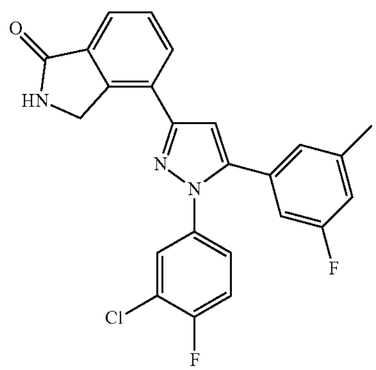 [SMILES: Cc1cc(F)cc(-c2cc(-c3cccc4c3CNC4=O)nn2-c2ccc(F)c(Cl)c2)c1] | | |
| Example 24 | 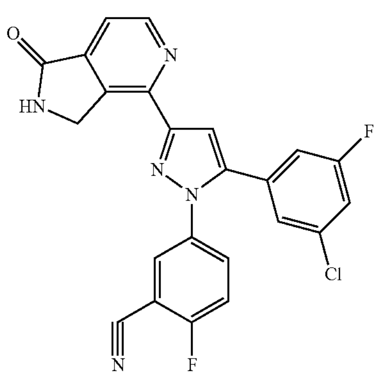 [SMILES: N#Cc1cc(-n2nc(-c3nccc4c3CNC4=O)cc2-c2cc(F)cc(Cl)c2)ccc1F] | | |
| Example 25 | 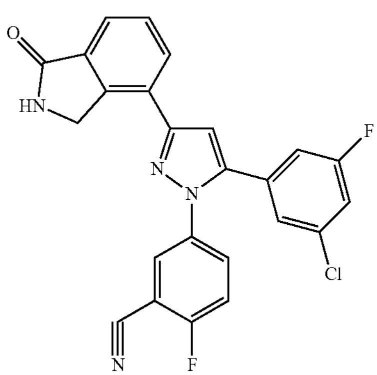 [SMILES: N#Cc1cc(-n2nc(-c3cccc4c3CNC4=O)cc2-c2cc(F)cc(Cl)c2)ccc1F] | | |

-continued

| | Structure | SM Step 1 | SM Step 4 |
|---|---|---|---|
| Example 26 | 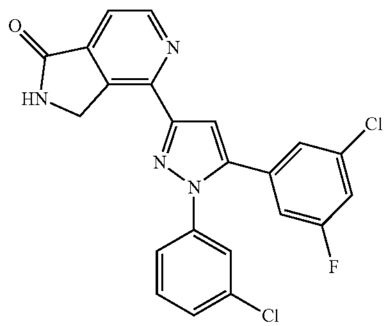 [SMILES: O=C1NCc2c1ccnc2-c1cc(-c2cc(F)cc(Cl)c2)n(-c2cccc(Cl)c2)n1] | | |
| Example 27 | 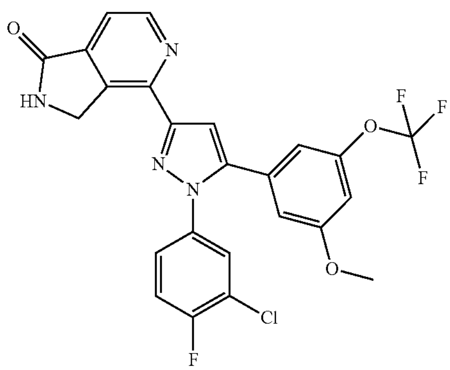 [SMILES: COc1cc(OC(F)(F)F)cc(-c2cc(-c3nccc4c3CNC4=O)nn2-c2ccc(F)c(Cl)c2)c1] | | |
| Example 28 | 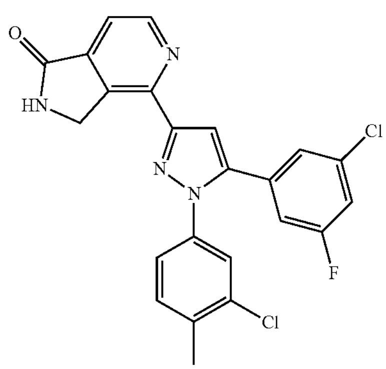 [SMILES: Cc1ccc(-n2nc(-c3nccc4c3CNC4=O)cc2-c2cc(F)cc(Cl)c2)cc1Cl] | | |
| Example 29 | 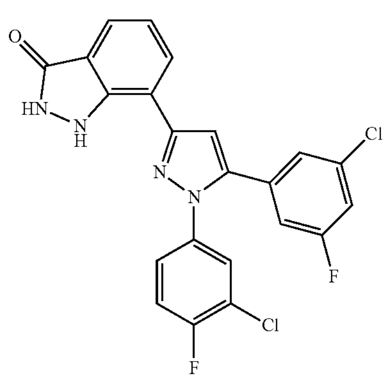 [SMILES: O=c1[nH][nH]c2c(-c3cc(-c4cc(F)cc(Cl)c4)n(-c4ccc(F)c(Cl)c4)n3)cccc12] | | |

-continued
| | Structure | SM Step 1 | SM Step 4 |
|---|---|---|---|
| Example 30 | 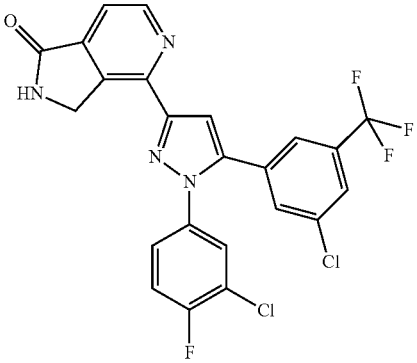 [SMILES: O=C1NCc2c1ccnc2-c1cc(-c2cc(Cl)cc(C(F)(F)F)c2)n(-c2ccc(F)c(Cl)c2)n1] | 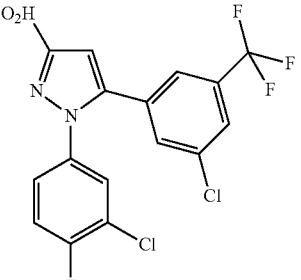 | 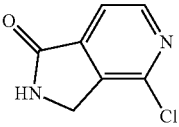 |
| Example 31 | 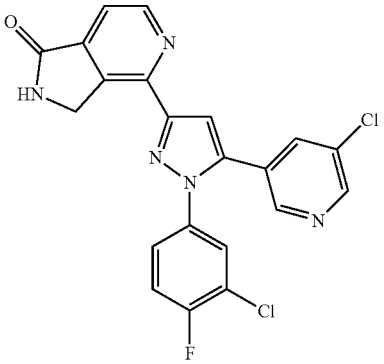 [SMILES: O=C1NCc2c1ccnc2-c1cc(-c2cncc(Cl)c2)n(-c2ccc(F)c(Cl)c2)n1] | 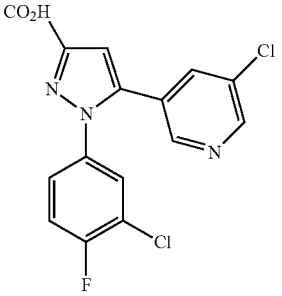 [SMILES: O=C(O)c1cc(-c2cncc(Cl)c2)n(-c2ccc(F)c(Cl)c2)n1] | 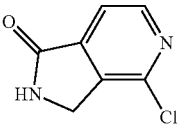 [SMILES: O=C1NCc2c1ccnc2Cl] |
| Example 32 | 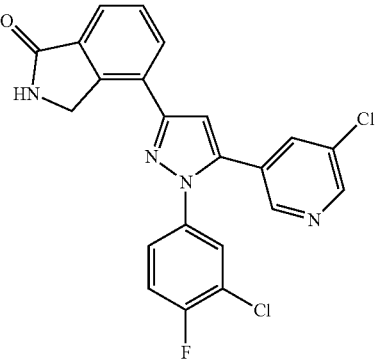 [SMILES: O=C1NCc2c1cccc2-c1cc(-c2cncc(Cl)c2)n(-c2ccc(F)c(Cl)c2)n1] | 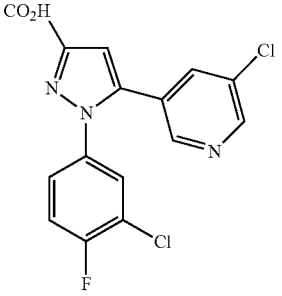 [SMILES: O=C(O)c1cc(-c2cncc(Cl)c2)n(-c2ccc(F)c(Cl)c2)n1] | 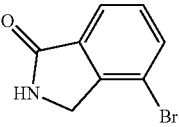 |
| Example 33 | 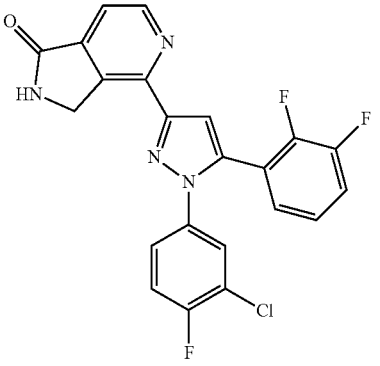 [SMILES: O=C1NCc2c1ccnc2-c1cc(-c2cccc(F)c2F)n(-c2ccc(F)c(Cl)c2)n1] | 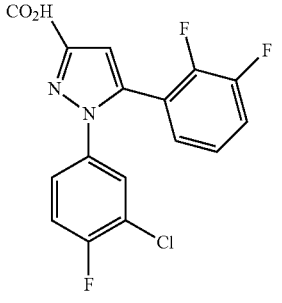 [SMILES: O=C(O)c1cc(-c2cccc(F)c2F)n(-c2ccc(F)c(Cl)c2)n1] | 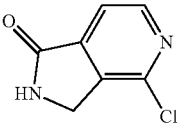 |

-continued

| | Structure | SM Step 1 | SM Step 4 |
|---|---|---|---|
| Example 34 | 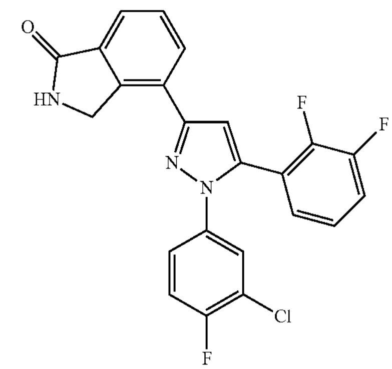 [SMILES: O=C1NCc2c1cccc2-c1cc(-c2cccc(F)c2F)n(-c2ccc(F)c(Cl)c2)n1] | | |
| Example 35 | 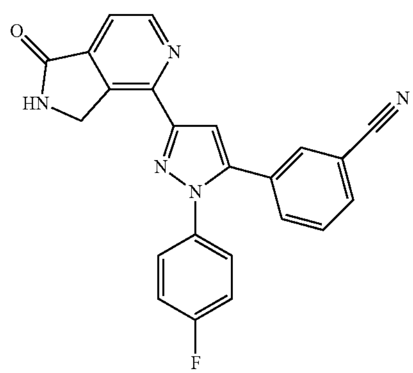 [SMILES: N#Cc1cccc(-c2cc(-c3nccc4c3CNC4=O)nn2-c2ccc(F)cc2)c1] | | |
| Example 36 | 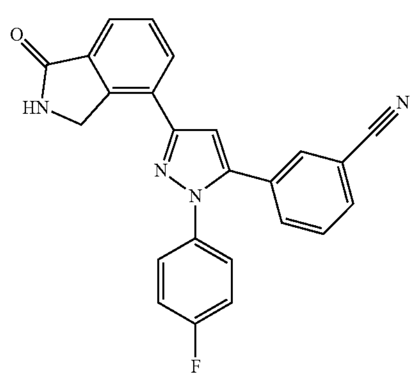 [SMILES: N#Cc1cccc(-c2cc(-c3cccc4c3CNC4=O)nn2-c2ccc(F)cc2)c1] | | |
| Example 37 | 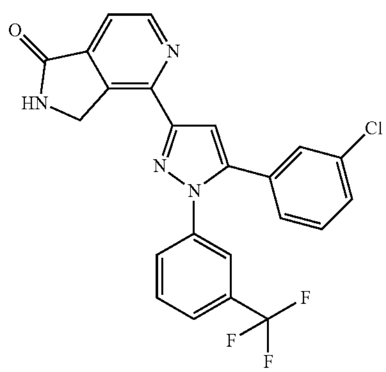 [SMILES: O=C1NCc2c1ccnc2-c1cc(-c2cccc(Cl)c2)n(-c2cccc(C(F)(F)F)c2)n1] | | |

-continued
| | Structure | SM Step 1 | SM Step 4 |
|---|---|---|---|
| Example 38 | 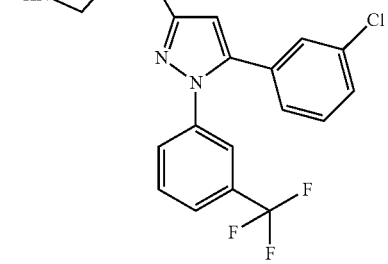 | 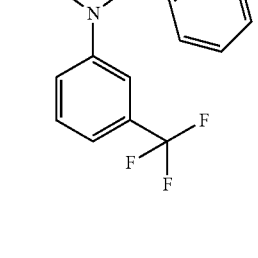 | 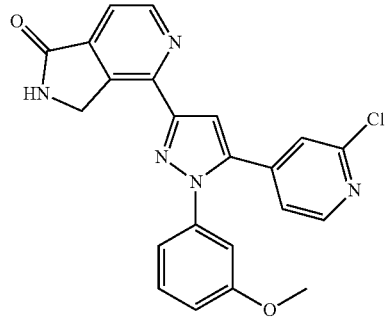 [SMILES: COc1cccc(-n2nc(-c3nccc4c3CNC4=O)cc2-c2ccnc(Cl)c2)c1] |
| Example 39 | 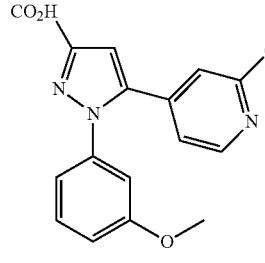 | 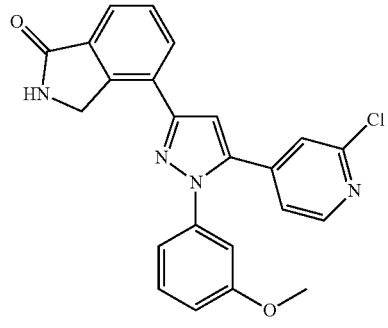 [SMILES: COc1cccc(-n2nc(-c3cccc4c3CNC4=O)cc2-c2ccnc(Cl)c2)c1] | 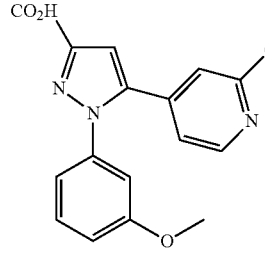 |
| Example 40 | 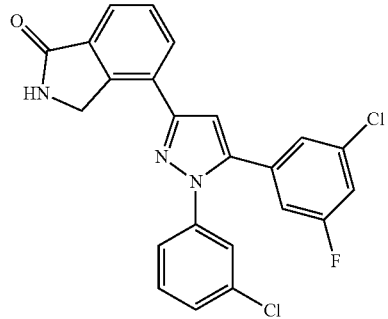 [SMILES: O=C1NCc2c1cccc2-c1cc(-c2cc(F)cc(Cl)c2)n(-c2cccc(Cl)c2)n1] | 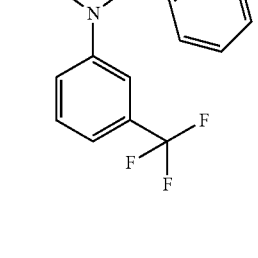 | 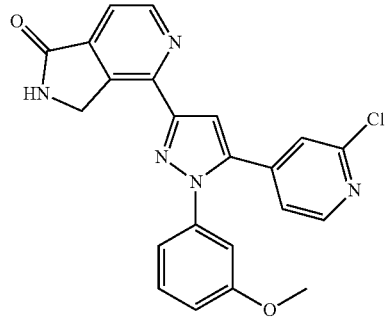 [SMILES: COc1cccc(-n2nc(-c3nccc4c3CNC4=O)cc2-c2ccnc(Cl)c2)c1] |
| Example 41 | 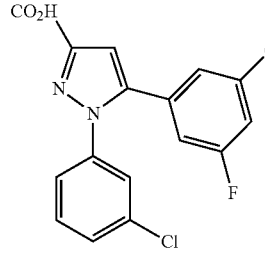 | | 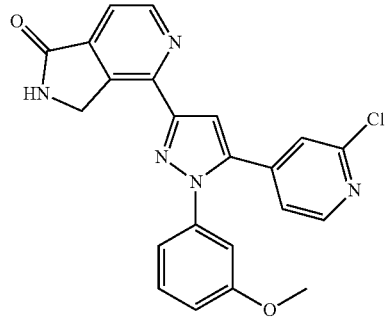 [SMILES: COc1cccc(-n2nc(-c3nccc4c3CNC4=O)cc2-c2ccnc(Cl)c2)c1] |

-continued

| | Structure | SM Step 1 | SM Step 4 |
|---|---|---|---|
| Example 42 | 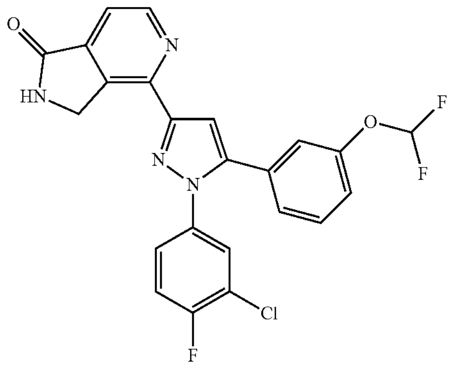 [SMILES: O=C1NCc2c1ccnc2-c1cc(-c2cccc(OC(F)F)c2)n(-c2ccc(F)c(Cl)c2)n1] | | |
| Example 43 | 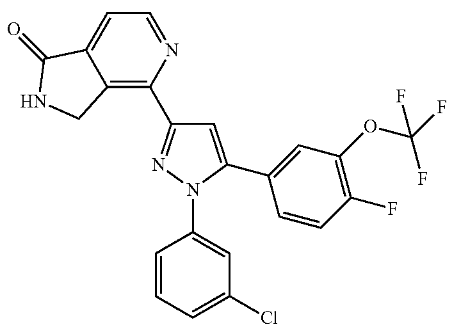 [SMILES: O=C1NCc2c1ccnc2-c1cc(-c2ccc(F)c(OC(F)(F)F)c2)n(-c2cccc(Cl)c2)n1] | | |
| Example 44 | 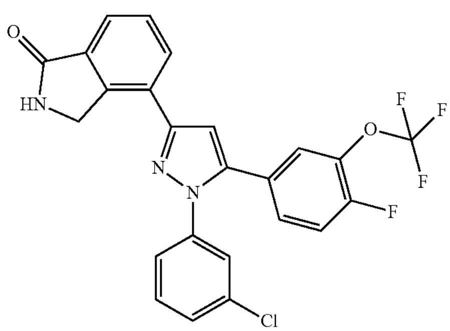 [SMILES: O=C1NCc2c1cccc2-c1cc(-c2ccc(F)c(OC(F)(F)F)c2)n(-c2cccc(Cl)c2)n1] | | |
| Example 45 | 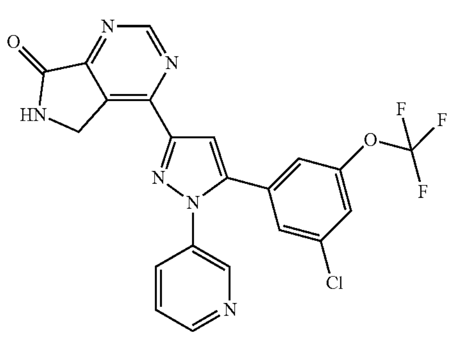 [SMILES: O=C1NCc2c1ncnc2-c1cc(-c2cc(Cl)cc(OC(F)(F)F)c2)n(-c2cccnc2)n1] | | |

| | Structure | SM Step 1 | SM Step 4 |
|---|---|---|---|
| Example 46 | [Structure of Example 46: 2-methyl-pyrrolopyrimidinone linked to pyrazole bearing 3-chloro-5-(trifluoromethoxy)phenyl and 3-pyridyl substituents] | [5-[3-chloro-5-(trifluoromethoxy)phenyl]-1-(pyridin-3-yl)-1H-pyrazole-3-carboxylic acid] | [4-chloro-2-methyl-6,7-dihydro-5H-pyrrolo[3,4-d]pyrimidin-7(6H)-one] |

The corresponding LC-MS and $^1$H-NMR data is provided below:

LC-MS and $^1$H-NMR Data

Example 22

LC-MS (Method 1): $R_t$=1.20 min; MS (ESIpos): m/z=437 [M+H]$^+$.

$^1$H-NMR (400 MHz, DMSO-d6): d [ppm]=2.31 (s, 3H), 4.81 (s, 2H), 6.94-7.01 (d, 1H), 7.08 (s, 1H), 7.10-7.15 (m, 1H), 7.33-7.40 (m, 2H), 7.50-7.56 (t, 1H), 7.66-7.70 (d, 1H), 7.79-7.83 (m, 1H), 8.82 (d, 1H), 9.03 (s, 1H).

Example 23

LC-MS (Method 1): $R_t$=1.27 min; MS (ESIpos): m/z=436 [M+H]$^+$.

$^1$H-NMR (400 MHz, DMSO-d6): d [ppm]=2.31 (s, 3H), 4.72 (s, 2H), 6.97 (d, 1H), 7.07 (s, 1H), 7.13 (d, 1H), 7.31-7.39 (m, 2H), 7.52 (t, 1H), 7.61 (t, 1H), 7.68-7.73 (m, 1H), 7.77 (dd, 1H), 8.14 (d, 1H), 8.70 (s, 1H).

Example 24

LC-MS (Method 1): $R_t$=1.11 min; MS (ESIpos): m/z=448 [M+H]$^+$.

$^1$H-NMR (400 MHz, DMSO-d6): d [ppm]=4.82 (s, 2H), 7.23-7.28 (m, 1H), 7.36 (s, 1H), 7.51 (s, 1H), 7.53-7.57 (m, 1H), 7.62-7.68 (m, 1H), 7.70 (d, 1H), 7.77 (dd, 1H), 8.24 (m, 1H), 8.82 (d, 1H), 9.06 (s, 1H).

Example 25

LC-MS (Method 1): $R_t$=1.17 min; MS (ESIpos): m/z=447 [M+H]$^+$.

$^1$H-NMR (400 MHz, DMSO-d6): d [ppm]=4.73 (s, 2H), 7.21 (d, 1H), 7.37 (s, 1H), 7.51 (s, 1H), 7.56 (d, 1H), 7.59-7.68 (m, 2H), 7.69-7.74 (d, 1H), 7.74-7.80 (m, 1H), 8.15 (d, 1H), 8.19 (dd, 1H), 8.72 (s, 1H).

Example 26

LC-MS (Method 2): $R_t$=2.56 min; MS (ESIpos): m/z=439 [M+H]$^+$.

$^1$H-NMR (400 MHz, DMSO-d6): d [ppm]=4.81 (s, 2H), 7.22-7.28 (m, 1H), 7.28-7.37 (m, 2H), 7.48-7.51 (m, 2H), 7.51-7.57 (m, 2H), 7.64-7.67 (m, 1H), 7.69 (d, 1H), 8.82 (d, 1H), 9.03 (s, 1H).

Example 27

LC-MS (Method 1): $R_t$=1.21 min; MS (ESIpos): m/z=519 [M+H]$^+$.

$^1$H-NMR (400 MHz, DMSO-d6): d [ppm]=3.82 (s, 3H), 4.80 (s, 2H), 6.71 (s, 1H), 7.02 (s, 1H), 7.15 (s, 1H), 7.38-7.47 (m, 1H), 7.50 (s, 1H), 7.52-7.61 (m, 1H), 7.69 (d, 1H), 7.80 (d, 1H), 8.82 (d, 1H), 9.06 (s, 1H).

Example 28

LC-MS (Method 1): $R_t$=1.24 min; MS (ESIpos): m/z=453 [M+H]$^+$.

$^1$H-NMR (400 MHz, DMSO-d6): d [ppm]=2.39 (s, 3H), 4.79 (s, 2H), 7.19-7.27 (m, 2H), 7.34 (s, 1H), 7.43-7.47 (m, 1H), 7.48 (s, 1H), 7.51-7.57 (m, 1H), 7.63-7.66 (m, 1H), 7.69 (d, 1H), 8.82 (d, 1H), 9.05 (s, 1H).

Example 29

LC-MS (Method 1): $R_t$=1.20 min; MS (ESIpos): m/z=457 [M+H]$^+$.

$^1$H-NMR (400 MHz, DMSO-d6): d [ppm]=7.07-7.17 (t, 1H), 7.18-7.27 (m, 1H), 7.30-7.42 (m, 2H), 7.44-7.52 (m, 2H), 7.52-7.60 (m, 1H), 7.66-7.73 (m, 1H), 7.86 (d, 1H), 8.17 (dd, 1H).

Example 30

LC-MS (Method 1): $R_t$=1.29 min; MS (ESIpos): m/z=507 [M+H]$^+$.

$^1$H-NMR (400 MHz, DMSO-d6): d [ppm]=4.80 (s, 2H), 7.41-7.46 (m, 1H), 7.52-7.59 (m, 1H), 7.59-7.63 (t, 2H), 7.68-7.72 (d, 1H), 7.83-7.85 (m, 1H), 7.85-7.89 (m, 1H), 7.94 (s, 1H), 8.83 (d, 1H), 9.04 (s, 1H).

Example 31

LC-MS (Method 1): $R_t$=1.04 min; MS (ESIpos): m/z=440 [M+H]$^+$.

$^1$H-NMR (400 MHz, DMSO-d6): d [ppm]=4.81 (s, 2H), 7.40-7.46 (m, 1H), 7.52-7.60 (m, 2H), 7.70 (d, 1H), 7.87-7.92 (m, 1H), 8.02 (m, 1H), 8.47-8.51 (m, 1H), 8.66-8.70 (m, 1H), 8.83 (d, 1H), 9.04 (s, 1H).

Example 32

LC-MS (Method 1): $R_t$=1.11 min; MS (ESIpos): m/z=439 [M+H]$^+$.

¹H-NMR (400 MHz, DMSO-d6): d [ppm]=4.72 (s, 2H), 7.38-7.44 (m, 1H), 7.51-7.57 (m, 2H), 7.60-7.66 (t, 1H), 7.69-7.74 (m, 1H), 7.83-7.87 (m, 1H), 7.99-8.02 (m, 1H), 8.12-8.16 (m, 1H), 8.48 (d, 1H), 8.68 (d, 1H), 8.71 (s, 1H).

Example 33

LC-MS (Method 1): $R_t$=1.13 min; MS (ESIpos): m/z=441 [M+H]⁺.
¹H-NMR (400 MHz, DMSO-d6): d [ppm]=4.85 (s, 2H), 7.26-7.41 (m, 3H), 7.44 (s, 1H), 7.48-7.54 (m, 1H), 7.54-7.63 (m, 1H), 7.68-7.72 (d, 1H), 7.83 (dd, 1H), 8.82 (d, 1H), 9.05 (s, 1H).

Example 34

LC-MS (Method 1): $R_t$=1.19 min; MS (ESIpos): m/z=440 [M+H]⁺.
¹H-NMR (400 MHz, DMSO-d6): d [ppm]=4.75 (s, 2H), 7.25-7.39 (m, 3H), 7.44 (s, 1H), 7.47-7.54 (m, 1H), 7.54-7.66 (m, 2H), 7.72 (d, 1H), 7.76-7.80 (m, 1H), 8.17 (d, 1H), 8.70 (s, 1H).

Example 35

LC-MS (Method 1): $R_t$=0.98 min; MS (ESIpos): m/z=396 [M+H]⁺.
¹H-NMR (400 MHz, DMSO-d6): d [ppm]=4.79 (s, 2H), 7.31-7.38 (m, 2H), 7.47-7.51 (m, 3H), 7.58-7.61 (m, 2H), 7.66-7.69 (d, 1H), 7.86-7.89 (m, 1H), 7.91 (s, 1H), 8.80-8.84 (d, 1H), 9.04 (s, 1H).

Example 36

LC-MS (Method 1): $R_t$=1.04 min; MS (ESIpos): m/z=395 [M+H]⁺.
¹H-NMR (400 MHz, DMSO-d6): d [ppm]=4.71 (s, 2H), 7.30-7.37 (m, 2H), 7.43-7.50 (m, 3H), 7.52-7.57 (d, 1H), 7.57-7.65 (m, 2H), 7.68-7.73 (d, 1H), 7.85-7.90 (d, 1H), 7.92 (s, 1H), 8.10-8.17 (d, 1H), 8.71 (s, 1H).

Example 37

LC-MS (Method 1): $R_t$=1.21 min; MS (ESIpos): m/z=455 [M+H]⁺.
¹H-NMR (400 MHz, DMSO-d6): d [ppm]=4.83 (s, 2H), 7.26-7.31 (m, 1H), 7.43-7.47 (m, 2H), 7.48-7.53 (m, 2H), 7.68-7.71 (d, 1H), 7.71-7.78 (m, 3H), 7.79-7.84 (m, 1H), 8.81-8.85 (d, 1H), 9.04 (s, 1H).

Example 38

LC-MS (Method 1): $R_t$=1.28 min; MS (ESIpos): m/z=454 [M+H]⁺.
¹H-NMR (400 MHz, DMSO-d6): d [ppm]=4.74 (s, 2H), 7.22-7.27 (m, 1H), 7.43-7.47 (m, 2H), 7.48-7.53 (m, 2H), 7.60-7.65 (t, 1H), 7.69-7.75 (m, 4H), 7.76-7.82 (m, 1H), 8.15-8.19 (m, 1H), 8.71 (s, 1H).

Example 39

LC-MS (Method 1): $R_t$=0.98 min; MS (ESIpos): m/z=418 [M+H]⁺.
¹H-NMR (400 MHz, DMSO-d6): d [ppm]=3.77 (s, 3H), 4.80 (s, 2H), 6.94-6.99 (m, 1H), 7.06-7.10 (m, 1H), 7.11-7.14 (m, 1H), 7.29 (dd, 1H), 7.42 (t, 1H), 7.54 (s, 1H), 7.65 (s, 1H), 7.69 (d, 1H), 8.41 (d, 1H), 8.82 (d, 1H), 9.03 (s, 1H).

Example 40

LC-MS (Method 1): $R_t$=1.04 min; MS (ESIpos): m/z=417 [M+H]⁺.
¹H-NMR (400 MHz, DMSO-d6): d [ppm]=3.77 (s, 3H), 4.71 (s, 2H), 6.95 (d, 1H), 7.04-7.11 (m, 2H), 7.23 (d, 1H), 7.40 (t, 1H), 7.55 (s, 1H), 7.59-7.66 (m, 2H), 7.71 (d, 1H), 8.14 (d, 1H), 8.41 (d, 1H), 8.70 (s, 1H).

Example 41

LC-MS (Method 1): $R_t$=1.28 min; MS (ESIpos): m/z=438 [M+H]⁺.
¹H-NMR (500 MHz, DMSO-d6): d [ppm]=4.72 (s, 2H), 7.20 (d, 1H), 7.29-7.34 (m, 2H), 7.46-7.56 (m, 4H), 7.59-7.65 (m, 2H), 7.71 (d, 1H), 8.14 (d, 1H), 8.68 (s, 1H).

Example 42

LC-MS (Method 1): $R_t$=1.13 min; MS (ESIpos): m/z=471 [M+H]⁺.
¹H-NMR (500 MHz, DMSO-d6): d [ppm]=4.81 (s, 2H), 7.19-7.26 (m, 4H), 7.36-7.41 (m, 1H), 7.43 (s, 1H), 7.45-7.56 (m, 2H), 7.69 (d, 1H), 7.78-7.82 (m, 1H), 8.82 (d, 1H), 9.01 (s, 1H).

Example 43

LC-MS (Method 1): $R_t$=1.24 min; MS (ESIpos): m/z=489 [M+H]⁺.
¹H-NMR (500 MHz, DMSO-d6): d [ppm]=4.81 (s, 2H), 7.32-7.36 (m, 1H), 7.44-7.48 (m, 2H), 7.48-7.53 (m, 2H), 7.53-7.60 (m, 2H), 7.60-7.65 (m, 1H), 7.68 (d, 1H), 8.82 (d, 1H), 9.01 (s, 1H).

Example 44

LC-MS (Method 1): $R_t$=1.30 min; MS (ESIpos): m/z=488 [M+H]⁺.
¹H-NMR (500 MHz, DMSO-d6): d [ppm]=4.72 (s, 2H), 7.29-7.34 (m, 1H), 7.42-7.45 (s, 1H), 7.45-7.54 (m, 4H), 7.56 (m, 1H), 7.59-7.67 (m, 2H), 7.69-7.73 (m, 1H), 8.13-8.17 (m, 1H), 8.67 (s, 1H).

Example 45

LC-MS (Method 1): $R_t$=1.02 min; MS (ESIpos): m/z=473 [M+H]⁺.
¹H-NMR (400 MHz, DMSO-d₆): d=4.80 (s, 2H), 7.25 (s, 1H), 7.57-7.59 (m, 1H), 7.6-7.72 (m, 3H), 7.91 (d, 1H), 8.68-8.73 (m, 2H), 9.45 (s, 2H).

Example 46

LC-MS (Method 1): $R_t$=1.07 min; MS (ESIpos): m/z=487 [M+H]⁺.
¹H-NMR (400 MHz, DMSO-d₆): d=2.81 (s, 3H), 4.73 (s, 2H), 7.25 (s, 1H), 7.50-7.61 (m, 1H), 7.61-7.75 (m, 3H), 7.91 (d, 1H), 8.60-8.78 (m, 2H), 9.38 (s, 1H).

D. Assessment of Physiological Activity

Abbreviations $CC_{50}$ Half cytotoxicity concentration
DMSO Dimethyl sulfoxide

EC$_{50}$ Half maximal effective concentration
FBS Fetal Bovine Serum (Biochrom AG, Berlin, Germany)
IC$_{50}$ Half maximal inhibitory concentration
PBS phosphate buffered saline
Pen/Strep Penicillin/Streptomycin
RPMI Roswell Park Memorial Institute
MOI multiplicity of infection
MTP microtitre plate
ELISA enzyme-linked immunosorbent assay The suitability of the compounds in accordance with the invention for use in methods for the treatment of diseases caused by retroviruses can be shown in the following assay systems:

The assay systems referred to below are to be regarded as examples and can be varied by one skilled in the art, by making modifications, or replaced by other suitable assay systems known to one skilled in the art for investigating the compounds in accordance with the invention against the background of retroviral diseases.

In-Vitro Assays
Biochemical Reverse Transcriptase Assay

The "Reverse Transcriptase Assay, colorimetric" (Roche Diagnostics GmbH, Mannheim, Germany) is used in accordance with the manufacturer's instructions. The test substances are dissolved in DMSO and used in the test in a 5-step dilution sequence (DMSO final concentration 1%). Using Prism4 software (GraphPad, San Diego, Calif.), the IC$_{50}$ values of the test substances are determined from the resulting dose-response curves as the concentration of the diluted test substance at which the measured optical density is 50% of the positive control.

It is found that the compounds in accordance with the invention inhibit reverse transcriptase activity. The IC$_{50}$ values are in the region of 0.05-0.85 µM.

Luminescence Reduction Assay

For this assay, HIV-1$_{NL4-3}$ reporter viruses are used which carry the luciferase164 gene (lu164) in place of the nef gene. The viruses are generated by transfection of 293T cells with the corresponding proviral pNL4-3 plasmid (Lipofectamine Reagent, Invitrogen, Karlsruhe, Germany). Starting from the proviral plasmid DNA, viruses with defined resistance mutations (single or combined) are produced in the reverse transcriptase gene using the "QuikChange II XL Site-Directed Mutagenesis Kit" (Stratagene, Cedar Creek, Tex., USA). Resistance mutations include, among others: L74V, A98G, A98S, L100I, K101E, K103N, V106A, V106I, V106M, V108I, V108A, E138K, V179I, V179D, V179E, Y181C, Y181I, Y188L, G190A, G190S, H221Y, P225H, F227C, F227L, F227V, M230I, M230L, L234I, P236L, N348I, T369A, T369I, T369V. MT4 cells infected with these reporter viruses (NIH AIDS Research and Reference Reagent Program) secrete luciferase into the medium, which enables the luminometric quantification of the virus replication.

For starting a 96-well MTP, 3 million MT4 cells are pelleted, suspended in 1 ml RPMI 1640 medium without phenol red (Invitrogen, Karlsruhe, Germany)/10% FBS/2 mM L-glutamine/1% Pen/Strep (Invitrogen, Karlsruhe, Germany), and incubated for 2 hours at 37° C. with a suitable quantity of the relevant HIV-1$_{NL4-3}$ reporter virus (pellet infection). Non-adsorbed viruses are then washed out, and the infected cells are pelleted again and suspended in 8 ml RPMI 1640 medium without phenol red/2% or 10% FBS/2 mM L-glutamine/1% Pen/Strep. From this, 90 µl per well is pipetted into a white 96-well MTP to 10 µl of test substance at a suitable level of dilution. In order to avoid edge effects, the edge wells of the MTP are not used for substance dilutions. The second vertical row of the MTP contains only infected cells (virus control) and the eleventh vertical row only non-infected cells (cell control), each in RPMI 1640 medium without phenol red/2% or 10% FBS/2 mM L-glutamine/1% Pen/Strep. The remaining wells of the MTP contain the compounds in accordance with the invention in various concentrations, starting from the third vertical row, from which the test substances are diluted in 3-step sequences up to the tenth vertical row by a factor of $3^7$. The test substances are dissolved in DMSO; the final DMSO concentration in the test formulation is 1%. The test samples are incubated for 5 days at 37° C./5% $CO_2$ and subjected to luminometric analysis after addition of 15 µl Lu164 buffer (65 mM NaCl, 300 mM MES pH 5.8, 5 mM glutathione and 1:200 coelenterazine (5 mg/ml in 30 µM glutathione/DMSO) (P.J.K. GmbH, Kleinblittersdorf, Germany). The EC$_{50}$ values of the test substances are determined using quattroWorkflow software (Quattroresearch, Martinsried, Germany) from the resulting dose-response curves as the concentration of infected cells treated in which the virus replication as measured in RLUs (relative light units) is 50% of the untreated infected cells.

It is found that the compounds in accordance with the invention inhibit HIV replication. Experimental data is summarized in Table A.

PBL and alamarBlue Viability Assay

Primary human blood lymphocytes (PBLs) are isolated from blood using Ficoll-Paque Leucosep tubes (Greiner Bio-One, Frickenhausen, Germany) and stimulated for 3 days in RPMI 1640 medium (Invitrogen, Karlsruhe, Germany)/10% FBS/2 mM L-glutamine/1% Pen/Strep with phytohaemagglutinin (90 µg/ml) and interleukin-2 (40 U/ml).

For starting a 96-well MTP, 3 million PBLs are pelleted, suspended in 1 ml RPMI 1640 medium/10% FBS/2 mM L-glutamine/1% Pen/Strep and incubated for 2 hours at 37° C. with a suitable quantity of the relevant HIV-1$_{LAI}$ (NIH AIDS Research & Reference Reagent Program, Germantown, USA) (pellet infection). Non-adsorbed viruses are then washed out, and the infected cells pelleted again and suspended in 18 ml RPMI 1640 medium/10% FBS/2 mM L-glutamine/1% Pen/Strep/Interleukin-2 (40 U/ml). From this, 180 µl per well is pipetted into a 96-well MTP to 20 µl of test substance at a suitable level of dilution. Alternatively, the HIV is added after preparation of the substance dilutes in the MTP together with the cells, and is not washed out (supernatant infection). In order to avoid edge effects, the edge wells of the MTP are not used for substance dilutions. The second vertical row of the MTP contains only infected cells (virus control) and the eleventh vertical row only non-infected cells (cell control), each in RPMI 1640 medium/10% FBS/2 mM L-glutamine/1% Pen/Strep/Interleukin-2 (40 U/ml). The remaining wells of the MTP contain the compounds in accordance with the invention in various concentrations, starting from the third vertical row, from which the test substances are diluted in 3-step sequences up to the tenth vertical row by a factor of $3^7$. The test substances are dissolved in DMSO; the final DMSO concentration in the test preparation is 1%. The test samples are incubated for 5 days at 37° C./5% $CO_2$. After 5 to 7 days, 50 µl of cell-free supernatant is removed from each well to determine its p24 content using p24 ELISA (HIV-1 p24CA Antigen Capture Assay Kit, NCI-Frederick Cancer Research and Development Center, Frederick, USA). From the resulting values of the photometric analysis (450/620 nm), the EC$_{50}$ values of the test substances are determined from the resulting dose-response curves using the Prism4 software (GraphPad, San Diego, Calif.) as the concentration of treated infected cells, where the p24 quantity is 50% of the untreated infected cells.

Alternatively, MT4 cells are used in place of PBLs for testing the test substances. HIV-1$_{LAI}$-infected MT4 cells (MOI 0.01, supernatant infection) are incubated in accordance with the procedure described above in RPMI 1640 medium using 2% or 10% FKS/2 mM L-glutamine/1% Pen/Strep in the presence of the test substances for 5 days at 37° C./5% $CO_2$ (10 µl diluted substance and 90 µl cells/virus per well). 10 µl alamarBlue (Invitrogen, Karlsruhe, Germany) is then added per well and the MTPs are incubated for 3 hours at 37° C. before fluorimetric evaluation is performed (544/590 nm). Using quattroWorkflow software (Quattroresearch, Martinsried, Germany), the $EC_{50}$ values of the test substances are determined from the resulting dose-response curves as the concentration of treated infected cells in which the fluorescence is 50% of that of the untreated, non-infected cells.

It is found that the compounds in accordance with the invention inhibit HIV replication. Experimental data is summarized in Table A.

Assay for Determining the Cytotoxic Effect of the Test Substances

To determine the cytotoxic effect of the test substances in non-infected cells, the substances are pipetted in appropriate quantities onto 96-well MTPs and incubated with non-infected cells (e.g. H9, PBLs, THP-1, MT4, CEM, Jurkat) (analogously to the assays described above). After 5 days, 1/10 by volume of alamarBlue is added to each well of the test samples and the MTPs then incubated for 3 hours at 37° C. A fluorimetric analysis is then performed (544/590 nm). The $CC_{50}$ values of the test substances are determined using quattroWorkflow software (Quattroresearch, Martinsried, Germany) from the resulting dose-response curves as the concentration of treated cells in which the fluorescence is 50% of that of the untreated cells. Experimental $CC_{50}$ values for all compounds listed in Table A are >3.3 µM.

TABLE A

| example | $EC_{50}$ (µM) MT4 cells HIV-1$_{NL4-3}$ wildtype 2% FBS | $EC_{50}$ (µM) MT4 cells HIV-1$_{NL4-3}$ K103N-Y181C 2% FBS | $EC_{50}$ (µM) MT4 cells HIV-1$_{LAI}$ wildtype 10% FBS |
|---|---|---|---|
| 1 | 0.0015 | 0.0040 | 0.0097 |
| 2 | 0.0013 | 0.0132 | 0.0063 |
| 3 | 0.0060 | 0.0289 | 0.0586 |
| 4 | 0.0055 | 0.0420 | 0.0155 |
| 5 | 0.0110 | 0.0117 | 0.1500 |
| 6 | 0.0024 | 0.0083 | 0.0137 |
| 7 | 0.0107 | 0.0206 | 0.0512 |
| 8 | 0.6430 | >3.3 | >3.3 |
| 9 | 0.0128 | 0.0176 | 0.0768 |
| 10 | 0.0012 | 0.0027 | 0.0080 |
| 11 | 0.0091 | 0.0240 | 0.0663 |
| 12 | 00089 | 0.0120 | 0.0974 |
| 13 | 0.0011 | 0.0025 | 0.0086 |
| 14 | 0.0010 | 0.0097 | 0.0053 |
| 15 | 0.0044 | 0.0085 | 0.0171 |
| 16 | 0.0005 | 0.0026 | 0.0023 |
| 17 | 0.0011 | 0.0049 | 0.0086 |
| 18 | 0.0056 | 0.0130 | 0.0177 |
| 19 | 0.0003 | 0.0019 | 0.0028 |
| 20 | 0.0010 | 0.0040 | 0.0118 |
| 21 | 0.0063 | 0.0283 | 0.0325 |
| 22 | 0.0009 | 0.0077 | 0.0245 |
| 23 | 0.0150 | 0.0565 | 0.0983 |
| 24 | 0.0002 | 0.0003 | 0.0006 |
| 25 | 0.0009 | 0.0112 | 0.0107 |
| 26 | 0.0017 | 0.0208 | 0.0153 |
| 27 | 0.0384 | 0.0219 | 0.1480 |
| 28 | 0.0172 | 0.0291 | 0.0876 |
| 29 | 0.3900 | 1.2160 | 2.0640 |
| 30 | 0.0075 | 0.0110 | 0.0881 |
| 31 | 0.0008 | 0.0024 | 0.0041 |
| 32 | 0.0069 | 0.0383 | 0.0273 |
| 33 | 0.0227 | 0.0610 | 0.0641 |
| 34 | 0.1310 | 0.4580 | 0.7500 |
| 35 | 0.0593 | 0.0317 | 0.1500 |
| 36 | 0.0848 | 0.0675 | 0.4490 |
| 37 | 0.0288 | 0.1480 | 0.0835 |
| 38 | 0.1800 | 1.1790 | 0.9480 |
| 39 | 0.0075 | 0.0692 | 0.0486 |
| 40 | 0.0517 | 0.4990 | 0.2220 |
| 41 | 0.0112 | 0.1520 | 0.0807 |
| 42 | 0.0098 | 0.0194 | 0.0717 |
| 43 | 0.0568 | 0.2000 | 0.6740 |
| 44 | 0.5330 | 0.4580 | 1.9080 |
| 45 | 0.0005 | 0.0007 | 0.0045 |
| 46 | 0.0004 | 0.0004 | 0.0023 |

In Vivo Assay

Animal Model:

NOD scid mice, generally 5-6 weeks of age, are acquired from commercial breeders (e.g. Taconic or Jackson Laboratory). The animals are kept in isolators under sterile conditions (including litter and feed).

A defined number of cells (e.g. $5 \times 10^6$ T-cells (e.g. C8166)) are infected with HIV using a suitable MOI (e.g. 0.01 $TCID_{50}$). The infected cells are inserted into collage sponges. The sponges pretreated in this manner are then implanted beneath the dorsal skin of the mice. The mice are treated once or multiple times daily orally, intraperitoneally, subcutaneously, or intravenously; the first treatment may be administered prior to implantation. The treatment groups normally comprise 10 mice. At least one group is treated with placebo, at least one group with a known effective substance (=positive control), and generally multiple groups with the substance in accordance with the invention. The daily dose of the substance in accordance with the invention is from 0.01 mg to 100 mg per kg of body mass. The formulation of the substances is in 2% DMSO/98% tylose (0.5% solution in PBS) or another suitable mixture that enhances the solubility of the substances. The treatment period is normally four and a half days. After the final administration of the substance, the animals are euthanized and the sponges removed. The cells infected with the virus are harvested from the sponge by collagenase digestion.

The total RNA is harvested from the cells, which is then tested in the quantitative PCR for its viral RNA content. The quantity of viral RNA is normalized on the basis of the quantity of a housekeeping gene (e.g. GAPDH). The quantity of HIV RNA after treatment with the substance is determined relative to the control group treated with placebo. If an HIV carrying a luciferase was used, a luciferase measurement may be performed, whether alternatively or additionally. In this case, the quantity of HIV is determined by means of the magnitude of the luciferase signal, as it serves in such as case as a measure of the virus replication. Statistical analysis is performed using suitable computer programs, e.g. GraphPad Prism.

E. Evaluation of Pharmacokinetic Characteristics

In Vivo Studies

To determine the in vivo pharmacokinetics, the test substances are applied to mice, rats, rabbits or dogs, intravenously and orally. For intravenous administration, a dosage of 0.5-1 mg/kg is used, and for oral administration, a dosage of 1-10 mg/kg. The test substances are formulated for intravenous administration in 1% DMSO/99% plasma, and for oral administration in 2% DMSO/98% tylose (0.5% solution in PBS), Labrafil M1944 CS or PEG 400 with ethanol and water in various proportions.

The quantitative determination of the substances is performed using the animal plasma and calibration samples, which were adjusted in plasma. The plasma proteins are removed via precipitation with acetonitrile (ACN). The samples are then separated by means of HPLC using different columns and subjected to mass spectrometric analysis. The evaluation of the plasma concentration time series is performed using an internal standard and a validated kinetics evaluation program.

Plasma Stability

The plasma used from the various species (CD-1 mouse, Wistar rat, and human) is acquired through blood sampling, in lithium heparin-coated monovettes with subsequent centrifuging, taken directly from a test subject or purchased commercially. To determine the plasma stability of the test substances, a 1 µM solution of each is incubated at 37° C. At various points in time, during an interval of up to 90 minutes, samples are removed from the incubation vessel. The samples removed are precipitated with ACN in order to stop the reaction and separate the plasma proteins. The samples are analyzed in the same manner as in the in vivo studies.

Microsomal and Hepatocyte Incubations

Incubations with liver microsomes of various species (CD-1 mouse, Wistar rat, and human) are performed at 37° C. Each incubation mixture receives 1 µM of the test substance as well as 0.5 mg/ml of microsomal protein. In addition, 0.05 M of phosphate buffer (pH=7.4), 1 mM EDTA, 5 mM glucose-6 phosphate and 1.5 U/ml of glucose-6 phosphate dehydroxygenase from *Leuconostoc mesenteroides* are added. The microsomal incubation is started by addition of NADPH (final concentration: 1 mM).

To determine the metabolic stability of the test substances in CD-1 mouse hepatocytes, $3\times10^5$ cells/ml are used. To determine the metabolic stability of the test substances in hepatocytes of Wistar rats and humans, $1\times10^6$ cells/ml are used. 1 µM of test substance is added to the hepatocytes, equivalently to the microsomal assay.

At time intervals of between 0 and 90 min, 100 µl is removed each time from each incubation formulation and ACN is added in order to stop the enzymatic reactions. After centrifuging, the samples are analyzed using LC-MS/MS; $CL_{intrinsic}'$ [ml/(min·kg)] and half-life period [min] are reported.

F. Exemplary Embodiments of Pharmaceutical Compositions

Compounds in accordance with the invention can be converted as follows into pharmaceutical compositions:

Orally Administrable Solution:

Composition and Manufacture

Example 1

2% DMSO/98% Tylose (0.5% Solution in PBS)

The compound in accordance with the invention is completely dissolved in the calculated volume of DMSO and the solution then suspended in tylose. The suspension is mixed, e.g. by stirring, ultrasound bath, or ULTRA-TURRAX, until a homogeneous suspension or solution is formed.

Example 2

100% Labrafil M 1944 CS

The compound in accordance with the invention is suspended in the calculated volume of Labrafil M 1944 CS. The suspension is mixed, e.g. by stirring, ultrasound bath, or ULTRA-TURRAX, until a homogeneous suspension or solution is formed.

Intravenous Solution

Composition and Manufacture

Example 3

1% DMSO/99% Plasma

The compound in accordance with the invention is completely suspended in the calculated volume of DMSO and the solution is then suspended in plasma. The suspension is mixed until a solution is formed.

The invention claimed is:
1. A compound of the formula

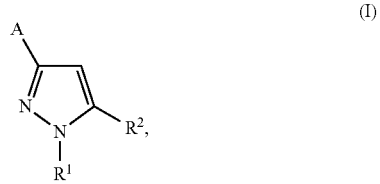

(I)

wherein
A stands for a group of the formula

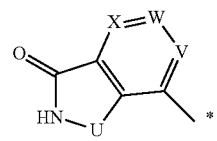

wherein
U stands for NH, $CH_2$ or C=O,
V stands for N or CH,

W stands for CH or CMe, wherein CMe stands for C—CH$_3$,

X stands for N or CH, and

* is the point of attachment to the carbon atom,

R$^1$ stands for phenyl or pyridyl, whereby phenyl is substituted with 1 to 2 substituents, the substituents being selected independently of one another from the group consisting of halogen, cyano, methyl, trifluoromethyl, methoxy and trifluoromethoxy, whereby pyridyl can be substituted with 1 or 2 substituents, the substituents being selected independently of one another from the group consisting of halogen, methyl and trifluoromethyl, and whereby the nitrogen atom of the pyridyl can form an N oxide, and R$^2$ stands for phenyl or pyridyl, whereby phenyl is substituted with 1 to 2 substituents, the substituents being selected independently of one another from the group consisting of halogen, cyano, (C$_1$-C$_4$)-alkyl and (C$_1$-C$_4$)-alkoxy, wherein alkyl and alkoxy in turn may be substituted with 1 to 3 fluorine atoms, whereby pyridyl can be substituted with 1 or 2 substituents, the substituents being selected independently of one another from the group consisting of halogen, cyano, (C$_1$-C$_4$)-alkyl, and (C$_1$-C$_4$)-alkoxy, and whereby the nitrogen atom of the pyridyl can form an N oxide, wherein alkyl and alkoxy in turn may be substituted with 1 to 3 fluorine atoms, or a salt thereof.

2. The compound in accordance with claim 1, characterized in that

A has the meaning given in claim 1, wherein

U stands for NH, CH$_2$ or C═O,

V stands for N or CH,

W stands for CH,

X stands for CH, and

* is the point of attachment to the carbon atom,

R$^1$ stands for phenyl or pyridyl, whereby phenyl is substituted with 1 or 2 substituents, where the substituents are selected independently of one another from the group consisting of halogen, cyano, methyl, trifluoromethyl, methoxy and trifluoromethoxy, whereby pyridyl can be substituted with 1 or 2 substituents, the substituents being selected independently of one another from the group consisting of halogen, methyl and trifluoromethyl, and whereby the nitrogen atom of the pyridyl can form an N-oxide, and R$^2$ stands for phenyl or pyridyl, whereby phenyl is substituted with 1 or 2 substituents, the substituents being selected independently of one another from the group consisting of halogen, cyano, (C$_1$-C$_4$)-alkyl and (C$_1$-C$_4$)-alkoxy, wherein alkyl and alkoxy on their part can be substituted with 1 to 3 fluorine atoms, whereby pyridyl can be substituted with 1 or 2 substituents, the substituents being selected independently of one another from the group consisting of halogen, cyano, (C$_1$-C$_4$)-alkyl and (C$_1$-C$_4$)-alkoxy and whereby the nitrogen atom of the pyridyl can form an N-oxide, wherein alkyl and alkoxy on their part can be substituted with 1 to 3 fluorine atoms, or a salt thereof.

3. The compound according to claim 1, characterized in that

A has the meaning given in claim 1, wherein

U stands for NH or CH$_2$,

V stands for N or CH,

W stands for CH or CMe, wherein CMe stands for C—CH$_3$,

X stands for N or CH, and

* is the point of attachment to the carbon atom,

R$^1$ stands for pyridyl, whereby pyridyl can be substituted with 1 or 2 substituents, the substituents being selected independently of one another from the group consisting of halogen, methyl and trifluoromethyl, and whereby the nitrogen atom of the pyridyl can form an N-oxide, and R$^2$ stands for phenyl, whereby phenyl is substituted with 1 or 2 substituents, the substituents being selected independently of one another from the group consisting of halogen, cyano, (C$_1$-C$_4$)-alkyl and (C$_1$-C$_4$)-alkoxy, wherein alkyl and alkoxy on their part can be substituted with 1 to 3 fluorine atoms, or a salt thereof.

4. The compound according to claim 1, characterized in that

A has the meaning given in claim 1, wherein

U stands for NH or CH$_2$, stands for N or CH,

W stands for CH,

X stands for CH, and

* is the point of attachment to the carbon atom,

R$^1$ stands for pyridyl, whereby pyridyl can be substituted with 1 or 2 substituents, the substituents being selected independently of one another from the group consisting of halogen, methyl and trifluoromethyl, and whereby the nitrogen atom of the pyridyl can form an N-oxide, and R$^2$ stands for phenyl, whereby phenyl is substituted with 1 or 2 substituents, the substituents being selected independently of one another from the group consisting of halogen, cyano, (C$_1$-C$_4$)-alkyl and (C$_1$-C$_4$)-alkoxy, wherein alkyl and alkoxy on their part can be substituted with 1 to 3 fluorine atoms, or a salt thereof.

5. The compound according to claim 1, characterized in that

A has the meaning given in claim 1, wherein

U stands for NH or CH$_2$,

V stands for N or CH,

W stands for CH or CMe, wherein CMe stands for C—CH$_3$,

X stands for N or CH, and

* is the point of attachment to the carbon atom,

R$^1$ stands for 3-pyridyl or 4-pyridyl, whereby pyridyl can be substituted with a halogen substituent, and R$^2$ stands for phenyl, whereby phenyl is substituted with 1 or 2 substituents, the substituents being selected independently of one another from the group consisting of halogen, cyano, (C$_1$-C$_4$)-alkyl, trifluoro-(C$_1$-C$_4$)-alkyl, (C$_1$-C$_4$)-alkoxy, trifluoro-(C$_1$-C$_4$)-alkoxy and difluoro-(C$_1$-C$_4$)-alkoxy, or a salt thereof.

6. The compound according to claim 1, characterized in that
A has the meaning given in claim 1, wherein
U stands for NH or $CH_2$,
V stands for N or CH,
W stands for CH,
X stands for CH, and
* is the point of attachment to the carbon atom,
$R^1$ stands for 3-pyridyl or 4-pyridyl,
whereby pyridyl can be substituted with a halogen substituent, and
$R^2$ stands for phenyl,
whereby phenyl is substituted with 1 or 2 substituents, the substituents being selected independently of one another from the group consisting of halogen, cyano, $(C_1-C_4)$-alkyl, trifluoro-$(C_1-C_4)$-alkyl, $(C_1-C_4)$-alkoxy, trifluoro-$(C_1-C_4)$-alkoxy and difluoro-$(C_1-C_4)$-alkoxy, or a salt thereof.

7. The compound in accordance with claim 1, characterized in that it corresponds to the formula

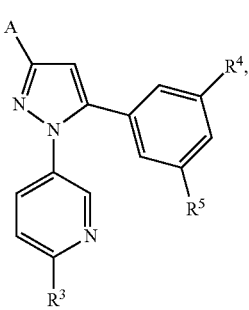

(Ia)

wherein
A, U, V, W and X have the meaning given in claim 1, and
* is the point of attachment to the carbon atom,
$R^3$ stands for hydrogen, halogen, trifluoromethyl or $(C_1-C_4)$-alkyl,
$R^4$ stands for hydrogen, halogen, $(C_1-C_4)$-alkyl or $(C_1-C_4)$-alkoxy,
wherein alkyl and alkoxy can be substituted with 1 to 3 fluorine atoms, and
$R^5$ stands for hydrogen, halogen, cyano, $(C_1-C_4)$-alkyl or $(C_1-C_4)$-alkoxy,
whereby $R^4$ and $R^5$ cannot simultaneously be hydrogen, or a salt thereof.

8. The compound in accordance with claim 7, characterized in that
A has the meaning given in claim 1, wherein
U stands for NH or $CH_2$,
V stands for N or CH,
W stands for CH or CMe, wherein CMe stands for C—$CH_3$,
X stands for N or CH, and
* is the point of attachment to the carbon atom,
$R^3$ stands for hydrogen or methyl,
$R^4$ stands for fluorine, difluoromethoxy or trifluoromethoxy, and
$R^5$ stands for fluorine, chlorine, bromine or methoxy, or a salt thereof.

9. The compound in accordance with claim 7, characterized in that
A has the meaning given in claim 1, wherein
U stands for NH or $CH_2$,
V stands for N or CH,
W stands for CH,
X stands for CH, and
* is the point of attachment to the carbon atom,
$R^3$ stands for hydrogen or methyl,
$R^4$ stands for fluorine, difluoromethoxy or trifluoromethoxy, and
$R^5$ stands for fluorine, chlorine, bromine or methoxy, or a salt thereof.

10. The compound in accordance with claim 1, characterized in that it corresponds to the formula

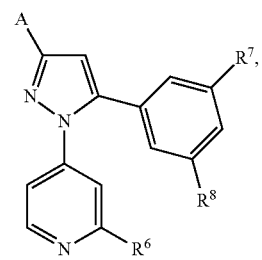

(Ib)

wherein
A, U, V, W and X have the meaning given in claim 1, and
* is the point of attachment to the carbon atom,
$R^6$ stands for hydrogen, halogen, trifluoromethyl, $(C_1-C_4)$-alkyl or $(C_1-C_4)$-alkoxy,
$R^7$ stands for hydrogen, halogen, $(C_1-C_4)$-alkyl or $(C_1-C_4)$-alkoxy,
wherein alkyl and alkoxy can be substituted with 1 to 3 fluorine atoms, and
$R^8$ stands for hydrogen, halogen, cyano, $(C_1-C_4)$-alkyl, or $(C_1-C_4)$-alkoxy,
whereby $R^7$ and $R^8$ cannot simultaneously be hydrogen, or a salt thereof.

11. The compound in accordance with claim 10, characterized in that
U stands for NH or $CH_2$,
stands for N or CH,
W stands for CH or CMe, wherein CMe stands for C—$CH_3$,
X stands for N or CH, and
* is the point of attachment to the carbon atom,
$R^6$ stands for chlorine, trifluoromethyl, methyl or methoxy,
$R^7$ stands for fluorine, methoxy, difluoromethoxy or trifluoromethoxy, and
$R^8$ stands for fluorine, chlorine, bromine or methoxy, or a salt thereof.

12. The compound in accordance with claim 11, characterized in that
U stands for NH or $CH_2$,
stands for N or CH,
W stands for CH,
X stands for CH, and
* is the point of attachment to the carbon atom,
$R^6$ stands for chlorine, trifluoromethyl, methyl or methoxy,
$R^7$ stands for fluorine, methoxy, difluoromethoxy or trifluoromethoxy, and
$R^8$ stands for fluorine, chlorine, bromine or methoxy, or a salt thereof.

13. The compound in accordance with claim 1, characterized in that it corresponds to the formula

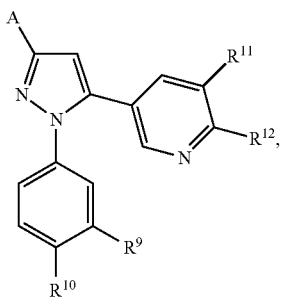

(Ic)

wherein

A, U, V, W and X have the meaning given in claim 1, $R^9$ stands for hydrogen, halogen, cyano, methyl, trifluoromethyl, methoxy or trifluoromethoxy, $R^{10}$ stands for hydrogen, halogen, trifluoromethyl, methyl, methoxy or trifluoromethoxy whereby $R^9$ and $R^{10}$ cannot simultaneously be hydrogen, $R^{11}$ stands for hydrogen, halogen, cyano, $(C_1$-$C_4)$-alkyl or $(C_1$-$C_4)$-alkoxy, wherein alkyl and alkoxy can be substituted with 1 to 3 fluorine atoms, and $R^{12}$ stands for hydrogen, $(C_1$-$C_4)$-alkyl or halogen, or a salt thereof.

14. The compound in accordance with claim 13, characterized in that it corresponds to the formula

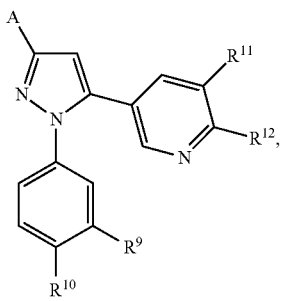

(Ic)

wherein

U stands for NH or $CH_2$,

V stands for N or CH,

W stands for CH,

X stands for CH, and

* is the point of attachment to the carbon atom, $R^9$ stands for hydrogen, halogen, cyano, methyl, trifluoromethyl, methoxy or trifluoromethoxy, $R^{10}$ stands for hydrogen, halogen, trifluoromethyl, methyl, methoxy or trifluoromethoxy, $R^{11}$ stands for hydrogen, halogen, cyano, $(C_1$-$C_4)$-alkyl or $(C_1$-$C_4)$-alkoxy, wherein alkyl and alkoxy can be substituted with 1 to 3 fluorine atoms, and $R^{12}$ stands for hydrogen, $(C_1$-$C_4)$-alkyl or halogen, or a salt thereof.

15. The compound in accordance with claim 1, characterized in that it corresponds to the formula

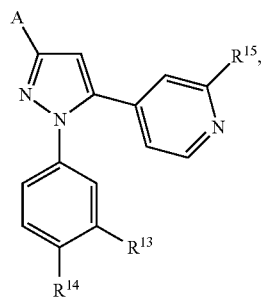

(Id)

wherein

A, U, V, W and X have the meaning given in claim 1, $R^{13}$ stands for hydrogen, halogen, cyano, methyl, trifluoromethyl, methoxy or trifluoromethoxy, $R^{14}$ stands for hydrogen, halogen, trifluoromethyl, methyl, methoxy or trifluoromethoxy, whereby $R^{13}$ and $R^{14}$ cannot simultaneously be hydrogen, and $R^{15}$ stands for hydrogen, halogen, cyano, $(C_1$-$C_4)$-alkyl or $(C_1$-$C_4)$-alkoxy, wherein alkyl and alkoxy can be substituted with 1 to 3 fluorine atoms, or a salt thereof.

16. The compound in accordance with claim 15, characterized in that it corresponds to the formula

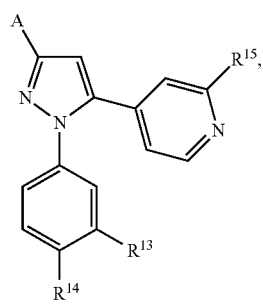

(Id)

wherein

U stands for NH or $CH_2$,

V stands for N or CH,

W stands for CH,

X stands for CH, and

* is the point of attachment to the carbon atom, $R^{13}$ stands for hydrogen, halogen, cyano, methyl, trifluoromethyl, methoxy or trifluoromethoxy, $R^{14}$ stands for hydrogen, halogen, trifluoromethyl, methyl, methoxy or trifluoromethoxy, whereby $R^{13}$ and $R^{14}$ cannot simultaneously be hydrogen, and $R^{15}$ stands for hydrogen, halogen, cyano, $(C_1$-$C_4)$-alkyl or $(C_1$-$C_4)$-alkoxy, wherein alkyl and alkoxy can be substituted with 1 to 3 fluorine atoms, or a salt thereof.

17. A method to produce a compound of formula (I) in accordance with claim 1, in which a compound of the following formula,

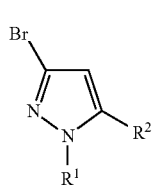
(II)

wherein $R^1$ and $R^2$ have the meaning specified in claim 1, is reacted with a compound of formula

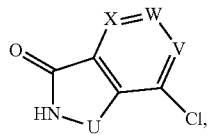
(III)

wherein U, V, W and X have the meaning specified in claim 1.

18. Pharmaceutical composition comprising at least one compound in accordance with claim 1 in combination with at least one inert, nontoxic, pharmaceutically suitable adjuvant.

19. Pharmaceutical composition in accordance with claim 18 for use in a method for the treatment of infections with retroviruses.

* * * * *